US006989028B2

(12) United States Patent
Lashinski et al.

(10) Patent No.: US 6,989,028 B2
(45) Date of Patent: Jan. 24, 2006

(54) MEDICAL SYSTEM AND METHOD FOR REMODELING AN EXTRAVASCULAR TISSUE STRUCTURE

(75) Inventors: Randall T. Lashinski, Santa Rosa, CA (US); Matthew J. Birdsall, Santa Rosa, CA (US); Michael D. Lesh, Mill Valley, CA (US)

(73) Assignee: Edwards Lifesciences AG, Saint-Prex (CH)

( * ) Notice: Subject to any disclaimer, the term of this patent is extended or adjusted under 35 U.S.C. 154(b) by 162 days.

(21) Appl. No.: 10/066,302

(22) Filed: Jan. 30, 2002

(65) Prior Publication Data

US 2002/0151961 A1    Oct. 17, 2002

Related U.S. Application Data

(63) Continuation-in-part of application No. 09/774,869, filed on Jan. 30, 2001, now Pat. No. 6,537,314, which is a continuation-in-part of application No. 09/494,233, filed on Jan. 31, 2000, now Pat. No. 6,402,781.

(60) Provisional application No. 60/265,995, filed on Feb. 1, 2001.

(51) Int. Cl.
*A61F 2/06* (2006.01)

(52) U.S. Cl. ............... 623/2.37; 623/2.36; 623/1.1; 600/37

(58) Field of Classification Search ............. 623/11.11, 623/1.1, 1.11, 1.12, 1.15, 1.16, 1.18, 1.2, 623/2.1, 2.11, 2.36, 2.37, 2.38, 1.23, 12, 66.1; 606/108, 191, 192, 194, 195, 198; 600/16, 600/37; 128/898; 604/95.01–95.05, 525, 604/528

See application file for complete search history.

(56) References Cited

U.S. PATENT DOCUMENTS

| 4,128,100 A | 12/1978 | Wendorff |
| 4,164,046 A | 8/1979 | Cooley |
| 4,655,771 A | 4/1987 | Wallsten |
| 4,917,698 A | 4/1990 | Carpentier et al. |
| 4,954,126 A | 9/1990 | Wallsten |
| 5,006,106 A | 4/1991 | Angelchik |
| 5,041,130 A | 8/1991 | Cosgrove et al. |
| 5,061,275 A | 10/1991 | Wallsten et al. |

(Continued)

FOREIGN PATENT DOCUMENTS

DE    196 05 042 A1    1/1998

(Continued)

OTHER PUBLICATIONS

Boyd et al., *Tricuspid annuloplasty*, Sep. 1974, *The Journal of Thoracic and Cardiovascular Surgery*, p. 344,351.

(Continued)

*Primary Examiner*—Urmi Chattopadhyay
(74) *Attorney, Agent, or Firm*—David L. Hauser

(57) ABSTRACT

A medical apparatus and method suitable for remodeling a mitral valve annulus adjacent to the coronary sinus. The apparatus comprises an elongate body having a proximal region and a distal region. Each of the proximal and distal regions is dimensioned to reside completely within the vascular system. The elongate body may be moved from a first configuration for transluminal delivery to at least a portion of the coronary sinus to a second configuration for remodeling the mitral valve annulus proximate the coronary sinus. A forming element may be attached to the elongate body for manipulating the elongate body from the first transluminal configuration to the second remodeling configuration. Further, the elongate body may comprise a tube having a plurality of transverse slots therein.

35 Claims, 30 Drawing Sheets

U.S. PATENT DOCUMENTS

| | | |
|---|---|---|
| 5,061,277 A | 10/1991 | Carpentier et al. |
| 5,064,431 A | 11/1991 | Gilbertson et al. |
| 5,064,435 A | 11/1991 | Porter |
| 5,099,838 A | 3/1992 | Bardy |
| 5,104,404 A | 4/1992 | Wolff |
| 5,104,407 A | 4/1992 | Lam et al. |
| 5,163,955 A | 11/1992 | Love et al. |
| 5,165,403 A | 11/1992 | Mehra |
| 5,170,802 A | 12/1992 | Mehra |
| 5,201,880 A | 4/1993 | Wright et al. |
| 5,290,300 A | 3/1994 | Cosgrove et al. |
| 5,304,131 A * | 4/1994 | Paskar ................ 604/95.04 |
| 5,350,420 A | 9/1994 | Cosgrove et al. |
| 5,383,892 A | 1/1995 | Cardon et al. |
| 5,450,860 A | 9/1995 | O'Connor |
| 5,476,471 A | 12/1995 | Shifrin et al. |
| 5,534,007 A | 7/1996 | St. Germain et al. |
| 5,545,209 A | 8/1996 | Roberts et al. |
| 5,562,619 A | 10/1996 | Mirarchi et al. |
| 5,571,135 A | 11/1996 | Fraser et al. |
| 5,584,879 A | 12/1996 | Reimold et al. |
| 5,593,424 A | 1/1997 | Northrup, III |
| 5,593,442 A | 1/1997 | Klein |
| 5,607,444 A | 3/1997 | Lam |
| 5,674,280 A | 10/1997 | Davidson et al. |
| 5,702,343 A | 12/1997 | Alferness |
| 5,713,949 A | 2/1998 | Jayaraman |
| 5,716,397 A | 2/1998 | Myers |
| 5,741,274 A | 4/1998 | Lenker et al. |
| 5,817,126 A | 10/1998 | Imran |
| 5,824,066 A | 10/1998 | Gross |
| 5,824,071 A | 10/1998 | Nelson et al. |
| 5,876,419 A | 3/1999 | Carpenter et al. |
| 5,891,108 A | 4/1999 | Leone et al. |
| 5,911,732 A | 6/1999 | Hojeibane |
| 5,919,233 A | 7/1999 | Knopf et al. |
| 5,961,440 A | 10/1999 | Schweich, Jr. et al. |
| 5,961,545 A | 10/1999 | Lentz et al. |
| 5,961,565 A | 10/1999 | Kawabe et al. |
| 5,980,552 A | 11/1999 | Pinchasik et al. |
| 6,001,127 A | 12/1999 | Schoon et al. |
| 6,027,525 A | 2/2000 | Suh et al. |
| 6,045,497 A | 4/2000 | Schweich, Jr. et al. |
| 6,050,936 A | 4/2000 | Schweich, Jr. et al. |
| 6,051,020 A | 4/2000 | Goicoechea et al. |
| 6,059,715 A | 5/2000 | Schweich, Jr. et al. |
| 6,071,292 A | 6/2000 | Makower et al. |
| 6,077,214 A | 6/2000 | Mortier et al. |
| 6,077,296 A | 6/2000 | Shokoohi et al. |
| 6,093,203 A | 7/2000 | Uflacker |
| 6,095,968 A | 8/2000 | Snyders |
| 6,110,100 A | 8/2000 | Talpade |
| 6,123,662 A | 9/2000 | Alferness et al. |
| 6,123,699 A * | 9/2000 | Webster, Jr. ................ 604/528 |
| 6,143,024 A | 11/2000 | Campbell et al. |
| 6,146,325 A | 11/2000 | Lewis et al. |
| 6,155,968 A | 12/2000 | Wilk |
| 6,155,972 A | 12/2000 | Nauertz et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,165,122 A | 12/2000 | Alferness |
| 6,171,329 B1 | 1/2001 | Shaw et al. |
| 6,174,279 B1 | 1/2001 | Girard |
| 6,183,411 B1 | 2/2001 | Mortier et al. |
| 6,183,512 B1 | 2/2001 | Howanec, Jr. et al. |
| 6,193,648 B1 | 2/2001 | Krueger |
| 6,203,556 B1 | 3/2001 | Evans et al. |
| 6,210,432 B1 | 4/2001 | Solem et al. |
| 6,217,610 B1 | 4/2001 | Carpentier et al. |
| 6,221,103 B1 | 4/2001 | Melvin |
| 6,230,714 B1 | 5/2001 | Alferness et al. |
| 6,241,654 B1 | 6/2001 | Alferness |
| 6,248,119 B1 | 6/2001 | Solem |
| 6,250,308 B1 | 6/2001 | Cox |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,264,691 B1 | 7/2001 | Gabbay |
| 6,325,826 B1 | 12/2001 | Vardi et al. |
| 6,343,605 B1 | 2/2002 | Lafontaine |
| 6,350,277 B1 | 2/2002 | Kocur |
| 6,368,343 B1 * | 4/2002 | Bonutti et al. ................ 606/232 |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,409,760 B1 | 6/2002 | Melvin |
| 6,537,314 B2 | 3/2003 | Langberg et al. |
| 6,569,198 B1 | 5/2003 | Wilson et al. |
| 6,602,288 B1 * | 8/2003 | Cosgrove et al. .......... 623/2.36 |
| 6,626,899 B2 | 9/2003 | Houser et al. |
| 6,656,221 B2 | 12/2003 | Taylor et al. |
| 6,669,687 B1 | 12/2003 | Saadat |
| 6,676,702 B2 | 1/2004 | Mathis |
| 6,706,065 B2 | 3/2004 | Langberg et al. |
| 6,709,456 B2 | 3/2004 | Langberg et al. |
| 6,764,510 B2 | 7/2004 | Vidlund et al. |
| 6,790,231 B2 | 9/2004 | Liddicoat et al. |
| 6,797,001 B2 | 9/2004 | Mathis et al. |
| 6,800,090 B2 | 10/2004 | Alferness et al. |
| 6,810,882 B2 | 11/2004 | Langberg et al. |
| 6,824,562 B2 | 11/2004 | Mathis et al. |
| 2001/0018611 A1 | 8/2001 | Solem et al. |
| 2001/0044568 A1 | 11/2001 | Langberg et al. |
| 2002/0016628 A1 | 2/2002 | Langberg et al. |
| 2002/0019660 A1 | 2/2002 | Gianotti et al. |
| 2002/0022880 A1 | 2/2002 | Melvin |
| 2002/0087173 A1 * | 7/2002 | Alferness et al. ............ 606/151 |
| 2002/0103533 A1 | 8/2002 | Langberg et al. |
| 2002/0111533 A1 | 8/2002 | Melvin |
| 2002/0124857 A1 | 9/2002 | Schroeppel |
| 2002/0151961 A1 | 10/2002 | Lashinski et al. |
| 2002/0169504 A1 * | 11/2002 | Alferness et al. .......... 623/2.36 |
| 2002/0183835 A1 | 12/2002 | Taylor et al. |
| 2002/0183836 A1 | 12/2002 | Liddicoat et al. |
| 2002/0183837 A1 | 12/2002 | Streeter et al. |
| 2002/0183838 A1 | 12/2002 | Liddicoat et al. |
| 2002/0183841 A1 | 12/2002 | Cohn et al. |
| 2003/0078465 A1 | 4/2003 | Pai et al. |
| 2003/0078654 A1 | 4/2003 | Taylor et al. |
| 2003/0083538 A1 | 5/2003 | Adams |
| 2003/0088305 A1 * | 5/2003 | Van Schie et al. .......... 623/1.12 |
| 2003/0105520 A1 | 6/2003 | Alferness et al. |
| 2003/0130730 A1 | 7/2003 | Cohn et al. |
| 2003/0130731 A1 * | 7/2003 | Vidlund et al. ............ 623/2.37 |
| 2003/0135267 A1 | 7/2003 | Solem et al. |
| 2003/0144697 A1 | 7/2003 | Mathis et al. |
| 2004/0019377 A1 | 1/2004 | Taylor et al. |
| 2004/0039443 A1 | 2/2004 | Solem et al. |
| 2004/0133192 A1 | 7/2004 | Houser et al. |
| 2004/0153146 A1 | 8/2004 | Lashinski et al. |
| 2004/0267358 A1 | 12/2004 | Reitan |

FOREIGN PATENT DOCUMENTS

| | | |
|---|---|---|
| DE | 196 11 755 A1 | 2/1998 |
| EP | 0 727 239 A2 | 8/1996 |
| EP | 0727 239 A3 | 4/1997 |
| WO | WO 91/19465 | 12/1991 |
| WO | WO 95/16407 | 6/1995 |
| WO | WO 96/34211 | 10/1996 |
| WO | WO 96/40356 | 12/1996 |
| WO | WO 98/18411 | 5/1998 |
| WO | WO 98/29041 | 7/1998 |

| | | |
|---|---|---|
| WO | WO 99/30647 | 6/1999 |
| WO | WO 99/44534 | 9/1999 |
| WO | WO 99/53977 | 10/1999 |
| WO | WO 00/06026 | 2/2000 |
| WO | WO 00/06027 | 2/2000 |
| WO | WO 00/06028 | 2/2000 |
| WO | WO 00/16700 | 3/2000 |
| WO | WO 00/18320 | 4/2000 |
| WO | WO 00/41649 | 7/2000 |
| WO | WO 00/44313 A1 | 8/2000 |
| WO | WO 01/00111 A1 | 1/2001 |
| WO | WO 01/00114 A1 | 1/2001 |
| WO | WO 01/28455 A1 | 4/2001 |
| WO | WO 01/50985 A1 | 7/2001 |
| WO | WO 01/54618 A1 | 8/2001 |
| WO | WO 01/85061 A2 | 11/2001 |
| WO | WO 01/89426 A1 | 11/2001 |
| WO | WO 02/00099 A2 | 1/2002 |
| WO | WO 02/01999 A2 | 1/2002 |
| WO | WO 02/05888 A1 | 1/2002 |
| WO | WO 02/34118 A2 | 5/2002 |
| WO | WO 02/053206 A2 | 7/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 02/076284 A2 | 10/2002 |
| WO | WO 02/078576 A2 | 10/2002 |
| WO | WO 02/096275 A2 | 12/2002 |
| WO | WO 2004/084746 A2 | 10/2004 |

OTHER PUBLICATIONS

Kurlansky et al., *Adjustable Annuloplasty for Tricuspid Insufficiency*, Oct. 1987, The Annals of Thoracic Surgery, p. 404-406.

Alonso-Lej. *Adjustable Annuloplasty for Tricuspid Insufficiency*, Sep. 1988, The Annals of Thoracic Surgery, Letter to the Editor, p. 368-369.

Chachques et al., *Latissimus Dorsi Dynamic Cardiomyoplasty*, 1989, The Society of Thoracic Surgeions, p. 600-604.

McCarthy et al., *Clinical experience with the Novacor ventricular assist system*, May 1990, J Thorac Cardiovasc Surg. p. 578-587.

Farrar et al., *A New Skeletal Muscle Linear-pull Energy Convertor as a Power Source for Prosthetic Circulatory Support Devices*, Sep. 1992, The Journal of Heart and Lung Transplantation, p. S341-S349.

Bolling et al., *Early outcome of mitral valve reconstruction in patients with end-stage cardiomyophathy*, Apr. 1995, The Journal of Thoracic and Cardiovascular Surgery, p. 676-683.

Bach et al., *Early improvement in congestive heart failure after correction of secondary mitral regurgitation in end-stage caridomyopathy* American Heart Journal, p. 1165-1170.

Bearnson et al., *Development of a Prototype Magnetically Suspended Rotar Ventricular Assist Device*, ASAIO Journal 1996, p. 275-280.

*Thoratec Ventricular Assist Device System*, 1996 Brochure.

McCarthy et al., *Early Results with Partial Left VEntriculectomy*, May 1997, Presented at the 77th Annual Meeting of the American Association of thoracic Surgeons.

Buchanan et al., *Circumferential Suture of the Mitral Annulus for Correction of Mitral Regurgitation in Dogs*, 1998, Veterinary Surgery vol. 27, p. 182-193.

Yamani et al., *Surgical Treatment of Chronic Heart Failure*, 2000, Congestive Heart Failure Second Edition, p. 767-784.

Bristow et al., *Heart Failure Management Using Implantable Devices for Ventricular Resynchronization: Comparison of Medical Therapy, Pacing, and Defibrillation in Chronic Heart Failure (COMPANION) Trial*, Sep. 2000, Journal of Cardiac Failure, vol. 6, No. 3, p. 276-285.

Smolens et al., *Mitral Valve Repair in Heart Failure*, 2000, European Journal of Heart Failure 2, p. 365-371.

U.S. Appl. No. 60/348,424, filed Jan. 2002, Taylor et al.

U.S. Appl. No. 60/279,973, filed Mar. 2001, Taylor et al.

U.S. Appl. No. 60/278,153, filed Mar. 2001, Cohn et al.

U.S. Appl. No. 60/339,481, filed Oct. 2001, Cohn et al.

U.S. Appl. No. 60/312,217, filed Aug. 2001. Taylor et al.

U.S. Appl. No. 60/283,820, filed Apr. 2001, Cohn et al.

U.S. Appl. No. 60/280,038, filed Mar. 2001, Cohn et al.

U.S. Appl. No. 60/279,974, filed Mar. 2001, Taylor et al.

U.S. Appl. No. 60/242,466, filed Oct. 2000, Streeter.

U.S. Appl. No. 60/266.766, filed Feb. 2001, Cohn et al.

U.S. Appl. No. 60/213,782, filed Jun. 2000, Cohn et al.

U.S. Appl. No. 60/273,893, filed Mar. 2001, Cohn et al.

Laaksovirta et al., *Expansion and bioabsorption of the self-reinforced lactic and glycolic acid copolymer prostatic spiral stent*, PubMed, Excerpt from J Urol Sep. 2001; 166(3):919-22, one sheet.

Liu et al., *Sutural expansion osteogenesis for management of the bony-tissue defect in cleft palate repair: experimental studies in dogs*, PubMed, Excerpt from Plast Reconstr Surg May 2000; 105(6):2012-25; discussion 2026-7, two sheets.

Yoneyama et al., *Super-elastic property of Ti-Ni alloy for use in dentistry*, PubMed, Excerpt Front Med Biol Eng 2000; 10(2):97-103, one sheet.

Kotian, *Shape memory effect and super elasticity it's dental applications*, PubMed, Excerpt from Indian J Dent Res Apr.-Jun. 2001; 12(2): 101-4, one sheet.

Kuo et al., *The use of nickel-titanium alloy in orthopedic surgery in China*, PubMed, Excerpt from Orthopedics Jan. 1989; 12(1):111-6, one sheet.

Civjan et al., *Potential applications of certain nickel-titanium (nitinol) alloys*, PubMed, Excerpt from J Dent Res Jan.-Feb. 1975;54(1):89-96, one sheet.

Brennan, *Suite of Shape-Memory Polymers*, http:///pubs.acs.org/cen/topstory/790notwl.html, News of the Week Materials, Feb. 5, 2001, vol. 79, No. 6, Cenear 79 6 pp. 5, ISSN 0009-2347, three sheets.

Stikeman, *Total Recall*, An MIT Enterprise Technology Review—Innovation, Jun. 2001, two sheets.

European Patent Office Office action dated Dec. 22, 2003 for Application No. 00 946 661.6-2310, 4 sheets.

Written Opinion dated Nov. 8, 2002 for International application No. PCT/EP01/10371, 14 sheets.

International Search Report dated Apr. 23, 2002 for International application No. PCT/EP 01/10371, 4 sheets.

International Search Report dated Mar. 15, 2000 for National application No. SE 9902455-6, 3 sheets.

International Search Report dated Oct. 9, 2002 for National application No. SE 0200073-5, 5 sheets.

International Search Report dated Jun. 5, 2003 for International application No. PCT/EP 02/14655, 7 sheets.

Buchanan JW, Sammarco CD, Circumferential Suture of the Mitral Annulus for Correction of Mitral Regurgitation in Dogs, PubMed, Excerpt from Vet Surg May-Jun. 1998; 27(3): 182-93, abstract, one sheet.

* cited by examiner

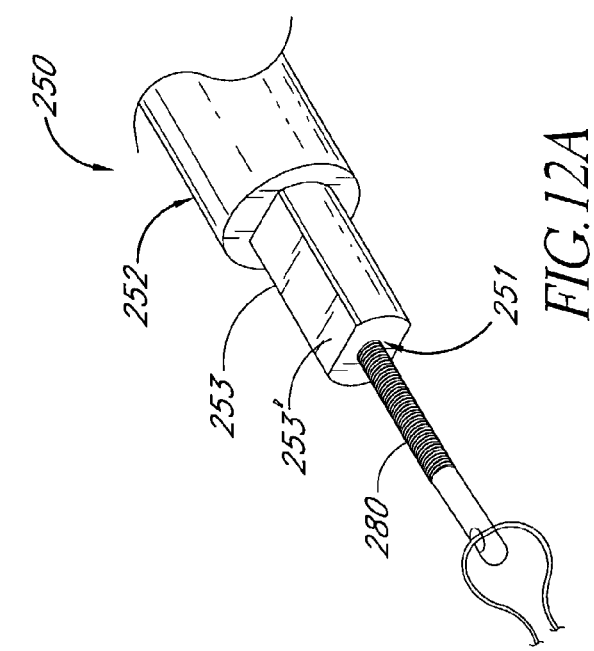
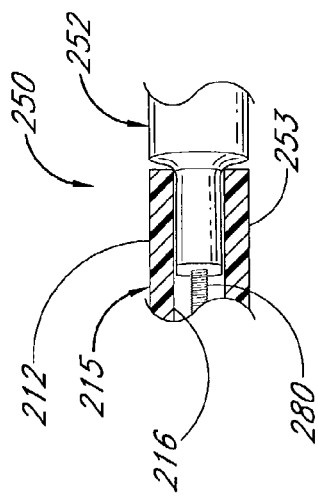
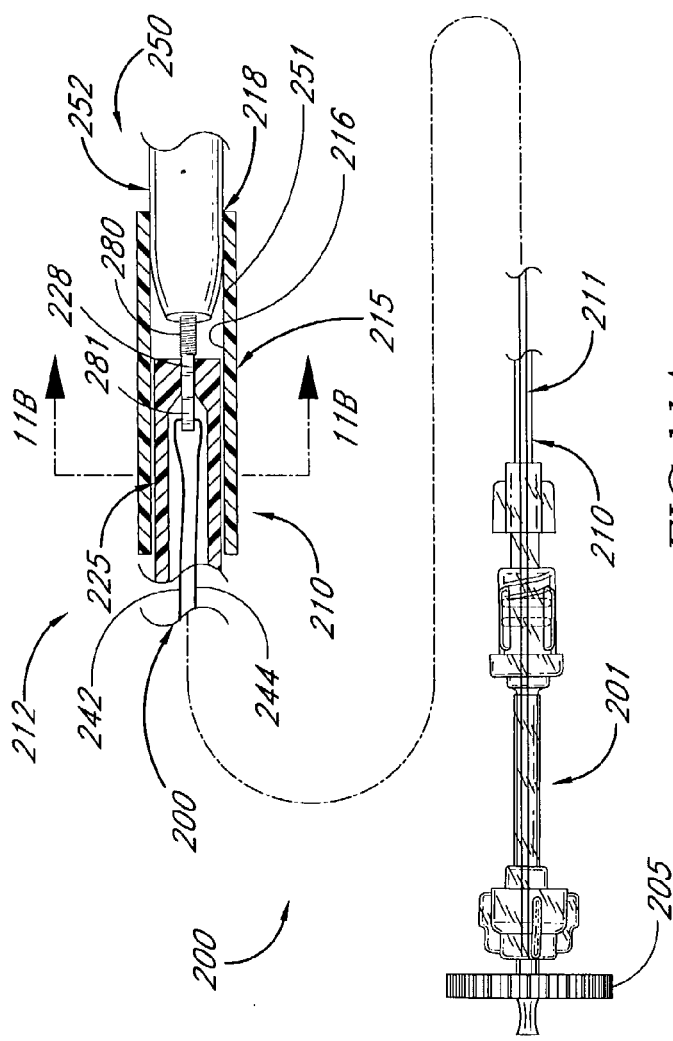
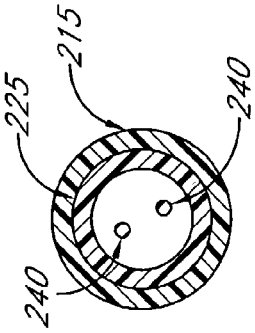

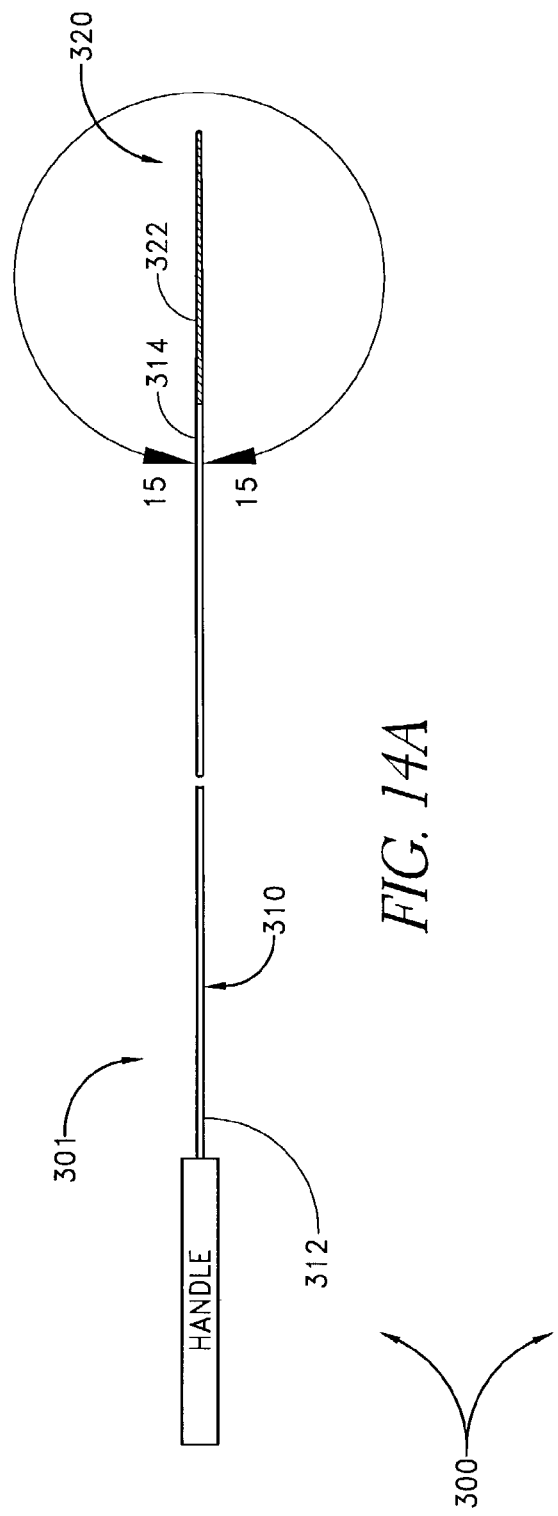
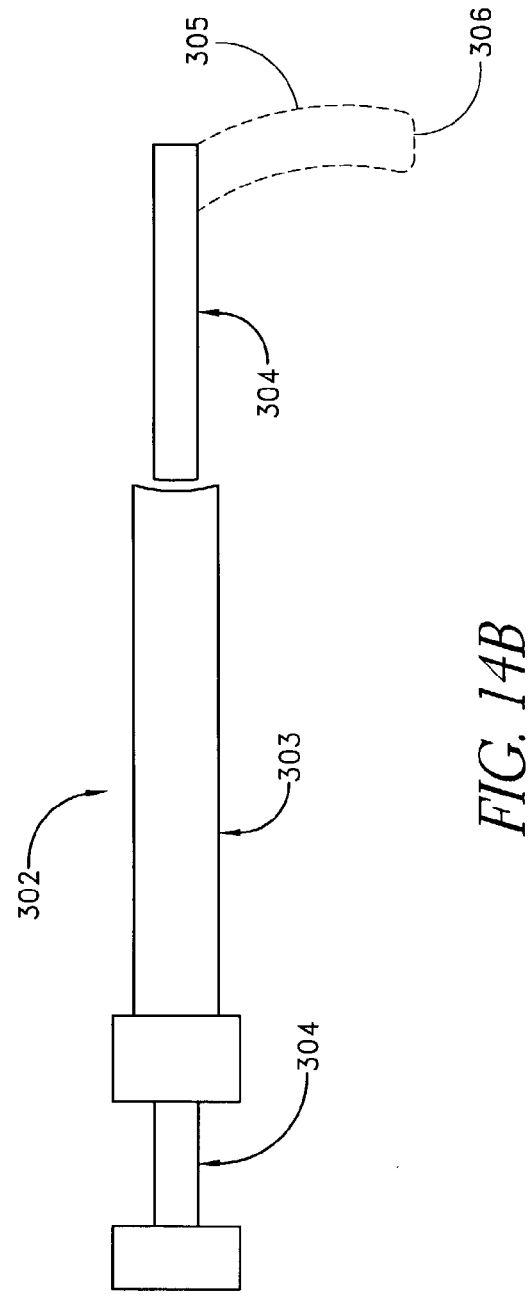
FIG. 14A
FIG. 14B

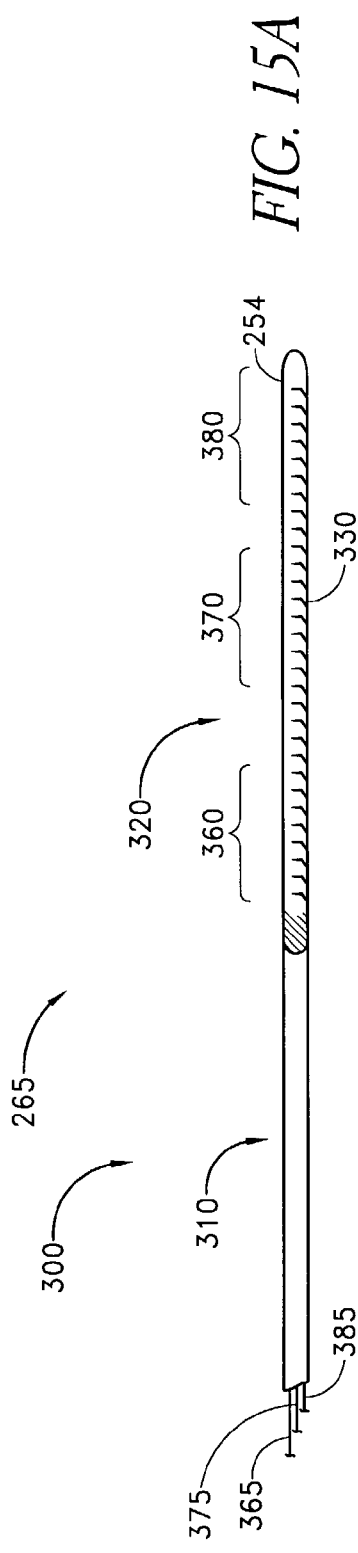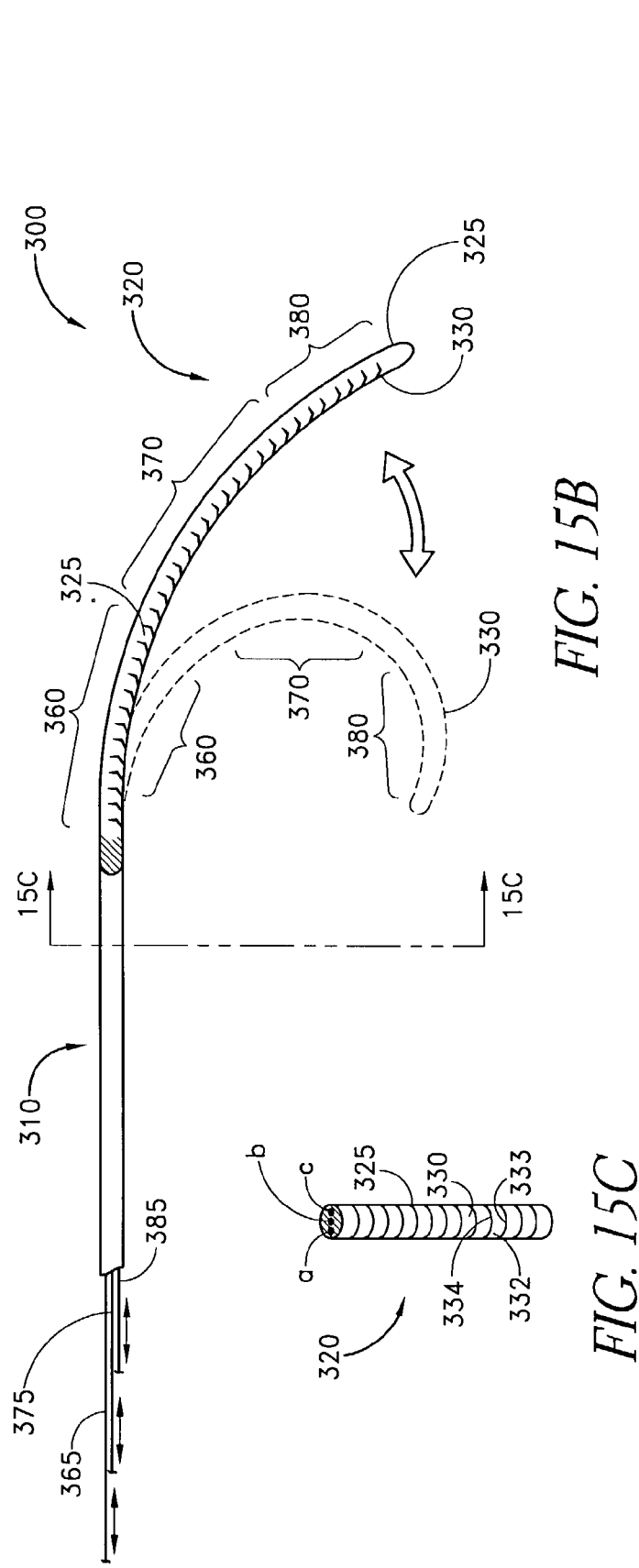

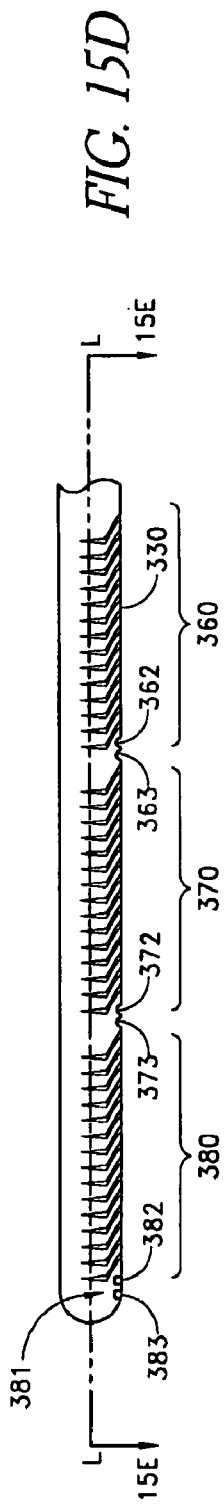
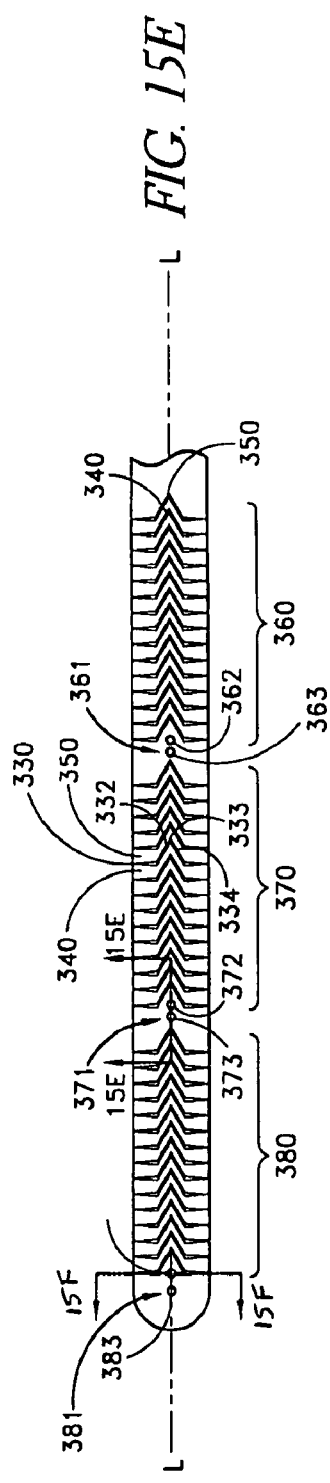
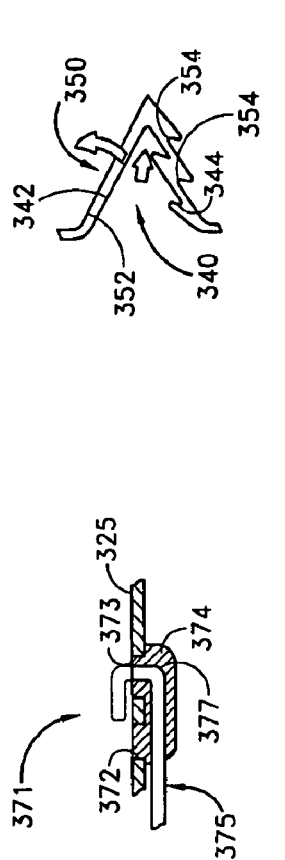
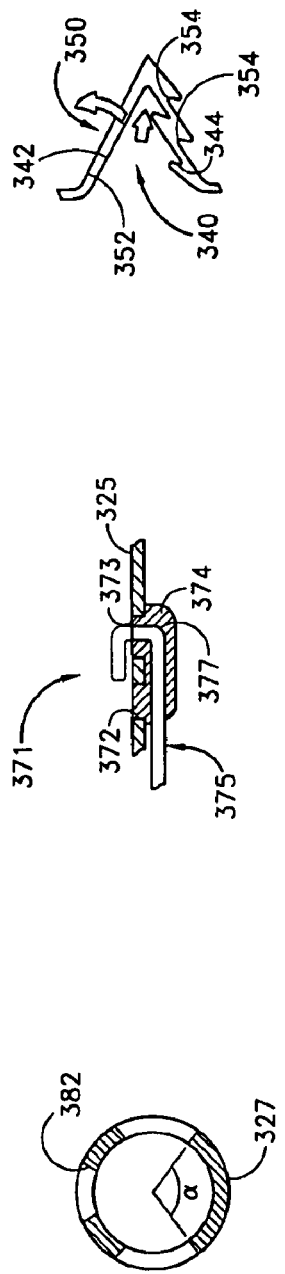
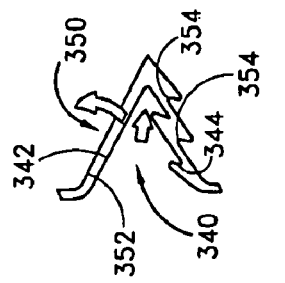

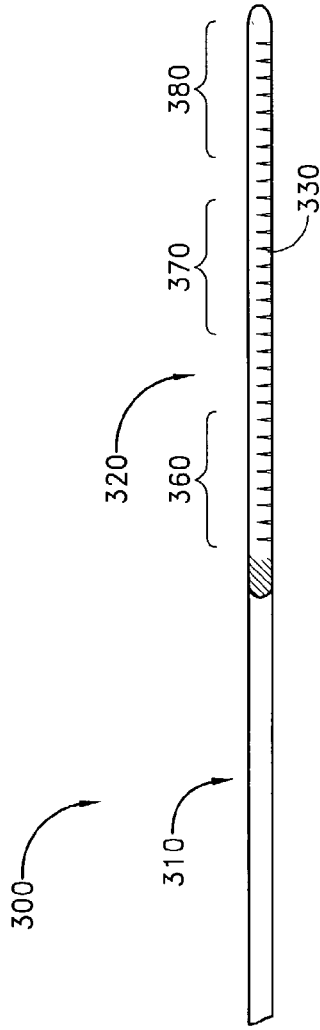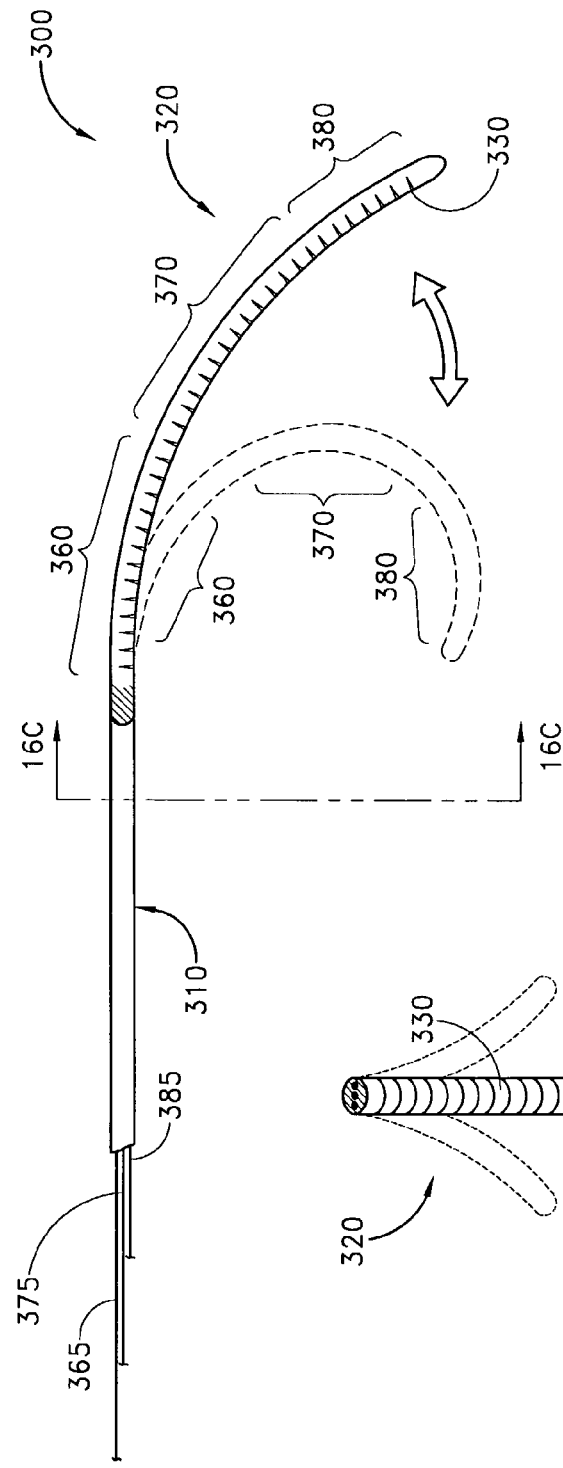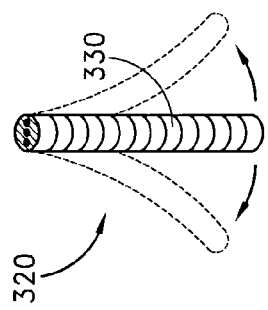

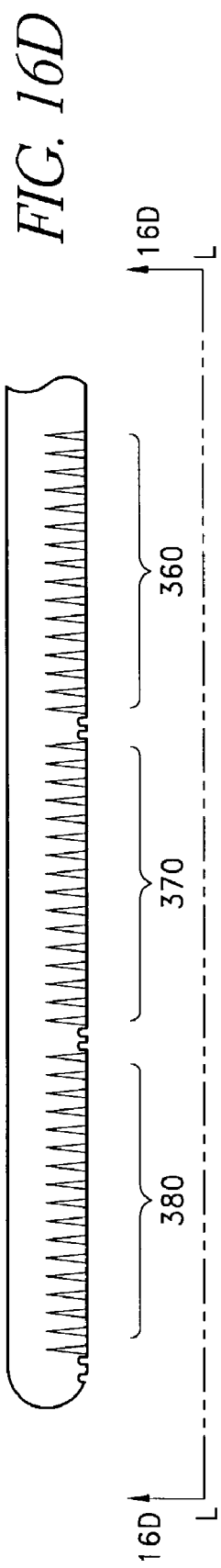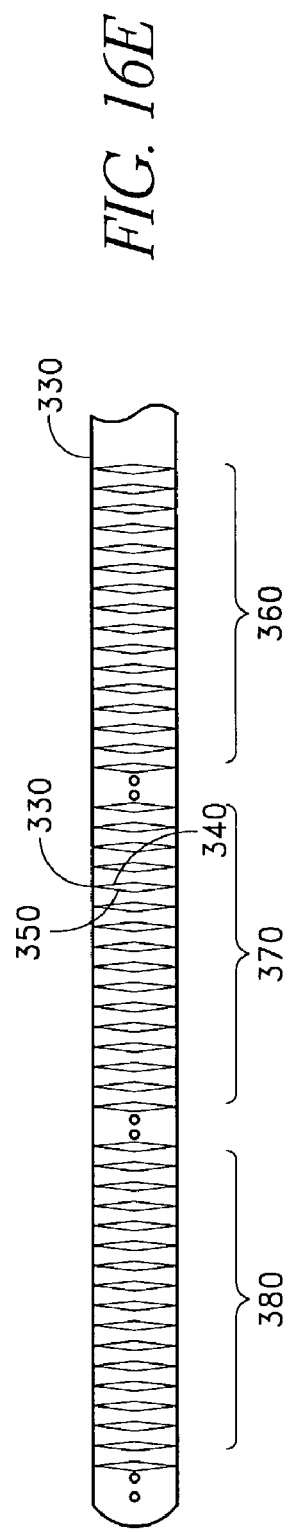

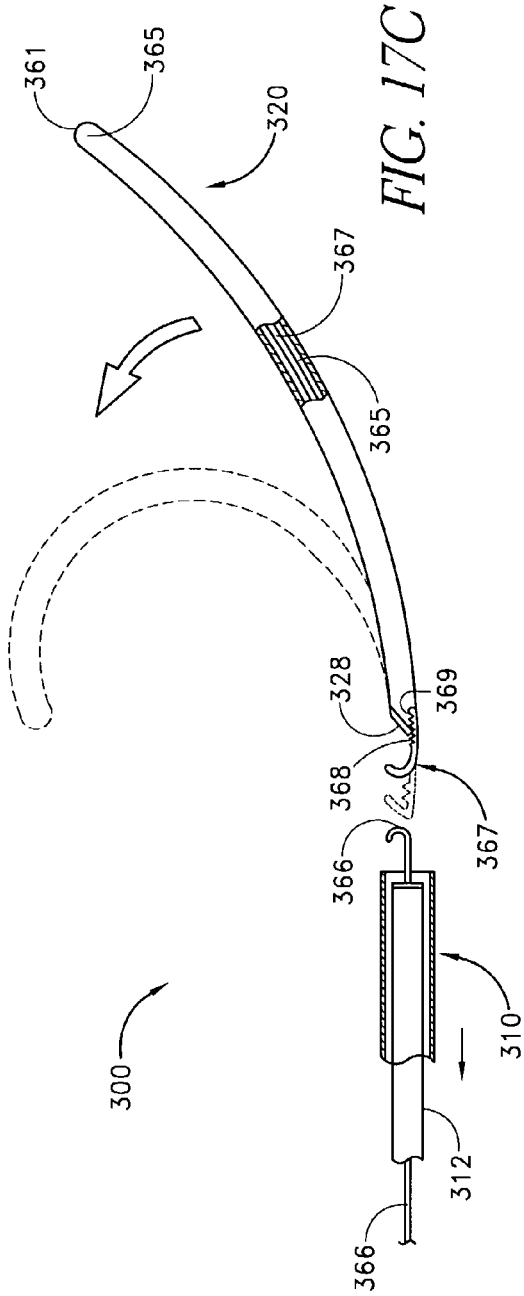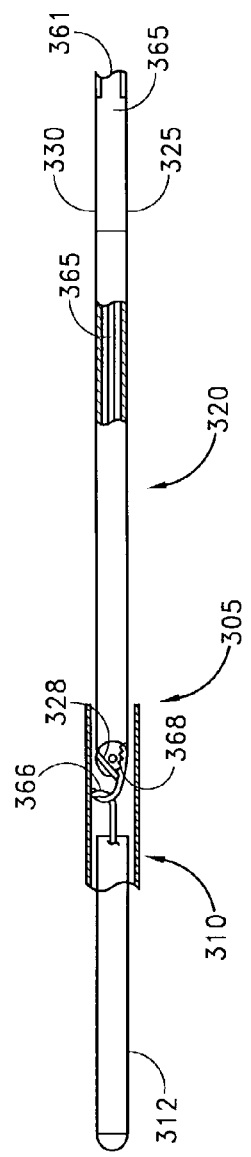
FIG. 17C
FIG. 17B

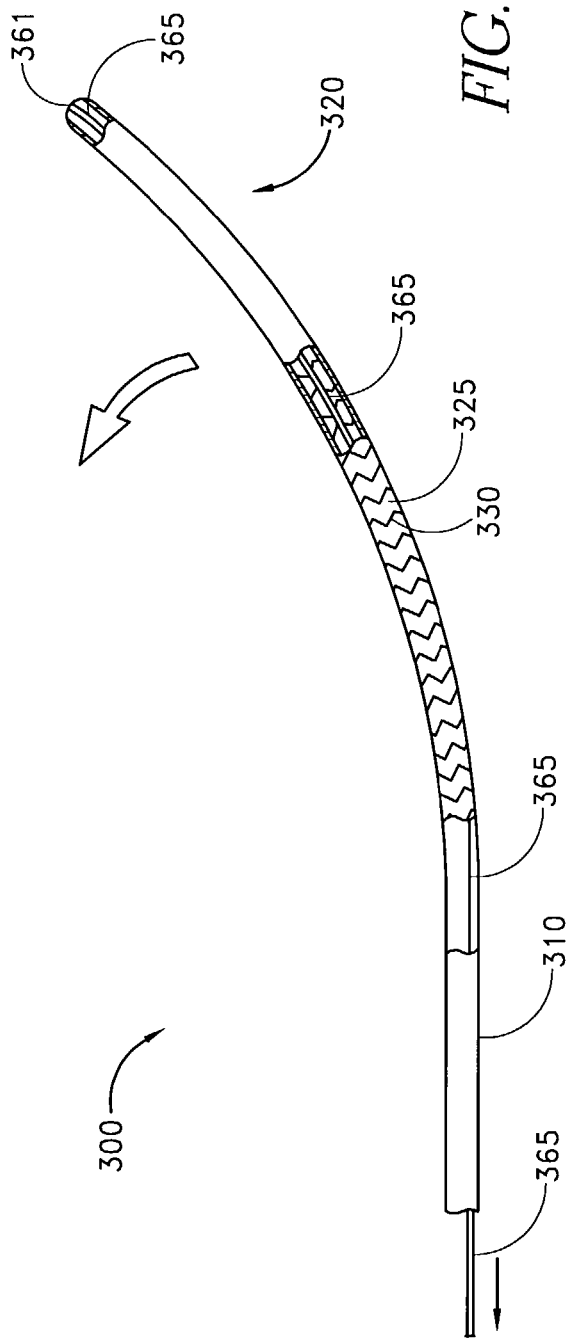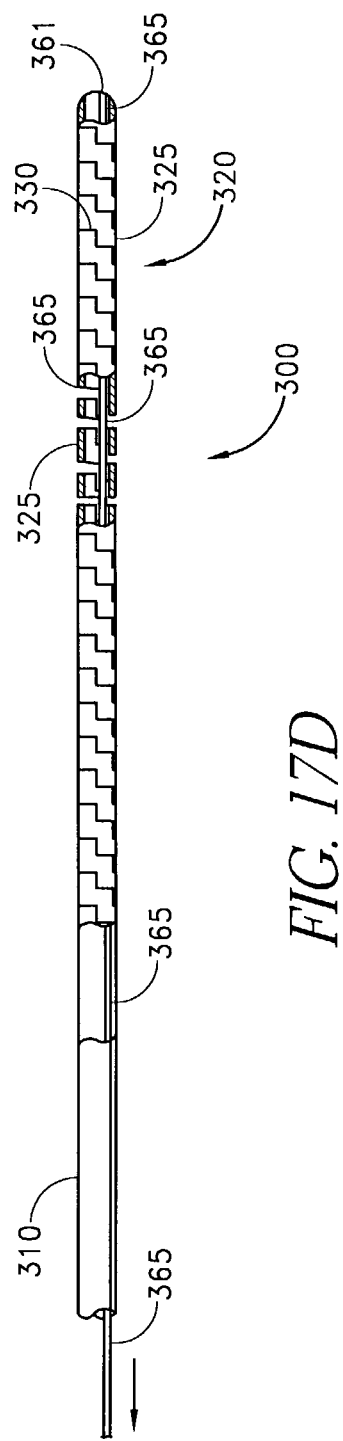

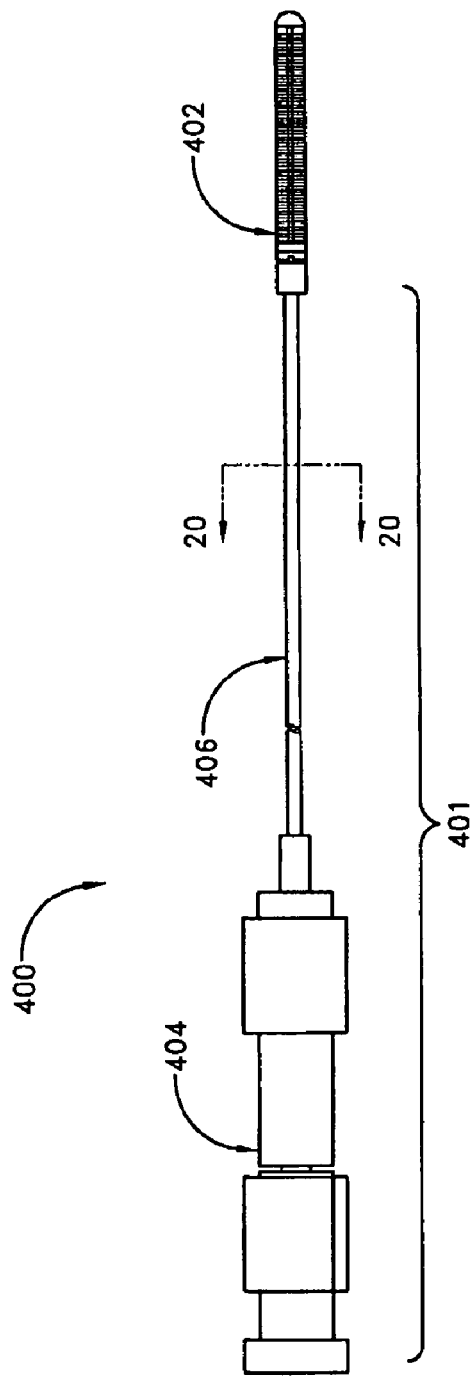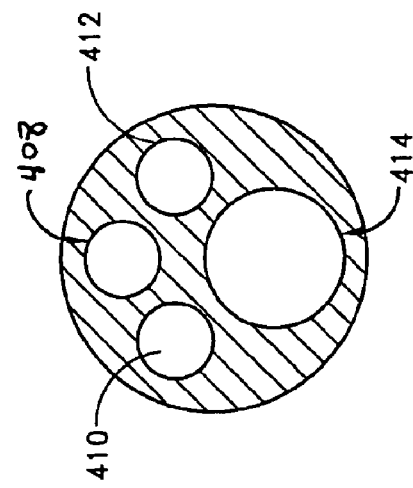
FIG. 19
FIG. 20

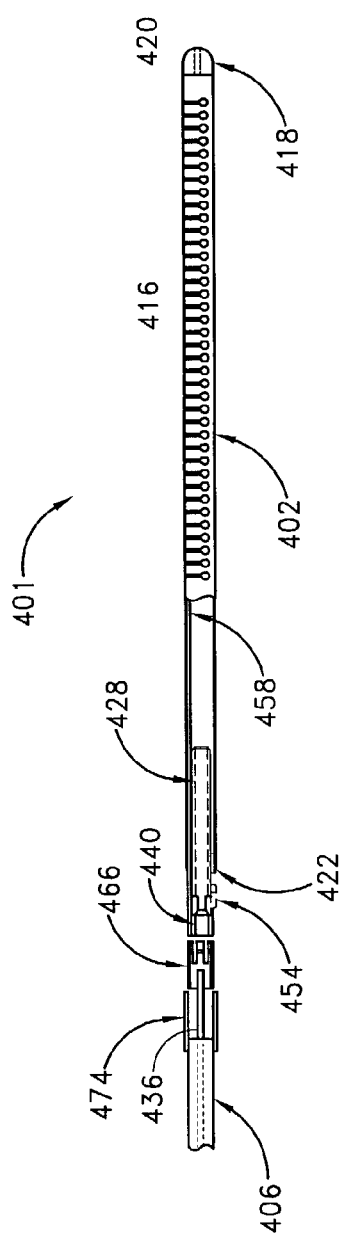
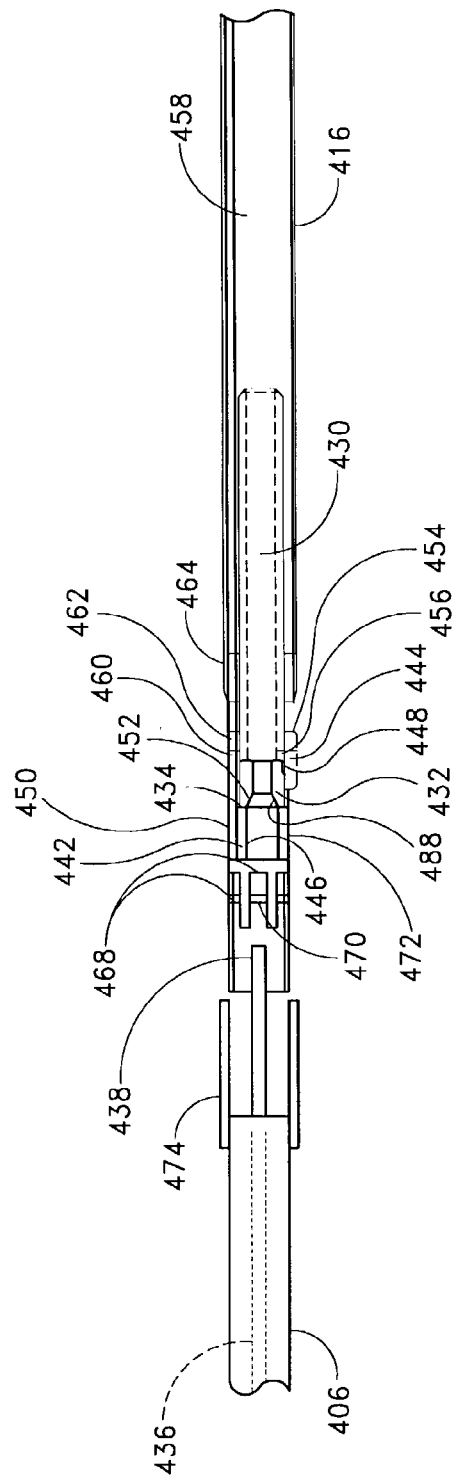
FIG. 21
FIG. 22

MEDICAL SYSTEM AND METHOD FOR REMODELING AN EXTRAVASCULAR TISSUE STRUCTURE

RELATED APPLICATIONS

This is a continuation-in-part of U.S. patent application Ser. No. 09/774,869, filed Jan. 30, 2001, now U.S. Pat. No. 6,537,314, which is a continuation-in-part of U.S. patent application Ser. No. 09/494,233, filed Jan. 31, 2000, now U.S. Pat. No. 6,402,781, and also claims priority under 35 U.S.C. § 119 to U.S. Provisional Application Ser. No. 60/265,995, filed Feb. 1, 2001, the disclosures of which are incorporated in their entireties herein by reference.

BACKGROUND OF THE INVENTION

1. Field of the Invention

The present invention relates to intravascular prostheses for remodeling an extravascular anatomical structure. In one application, the present invention relates to a mitral annuloplasty and cardiac reinforcement device which is transluminally implantable in the coronary sinus.

2. Description of the Related Art

Dilated cardiomyopathy occurs as a consequence of many different disease processes that impair myocardial function, such as coronary artery disease and hypertension. The left ventricle enlarges and the ejection fraction is reduced. The resulting increase in pulmonary venous pressure and reduction in cardiac output cause congestive heart failure. Enlargement of the mitral annulus and left ventricular cavity produce mitral valvular insufficiency. This in turn, causes volume overload that exacerbates the myopathy, leading to a vicious cycle of progressive enlargement and worsening mitral regurgitation.

According to recent estimates, more than 79,000 patients are diagnosed with aortic and mitral valve disease in U.S. hospitals each year. More than 49,000 mitral valve or aortic valve replacement procedures are performed annually in the U.S., along with a significant number of heart valve repair procedures.

Various surgical techniques have been developed to repair a diseased or damaged valve. One repair technique which has been shown to be effective in treating incompetence, particularly of the mitral and tricuspid valves, is annuloplasty, in which the effective size of the valve annulus is contracted by attaching a prosthetic annuloplasty ring to the endocardial surface of the heart around the valve annulus. The annuloplasty ring comprises an inner substrate of a metal such as stainless steel or titanium, or a flexible material such as silicone rubber or Dacron cordage, covered with a biocompatible fabric or cloth to allow the ring to be sutured to the heart tissue. The annuloplasty ring may be stiff or flexible, may be split or continuous, and may have a variety of shapes, including circular, D-shaped, C-shaped, or kidney-shaped. Examples are seen in U.S. Pat. Nos. 4,917,698, 5,061,277, 5,290,300, 5,350,420, 5,104,407, 5,064,431, 5,201,880, and 5,041,130, which are incorporated herein by reference.

Annuloplasty rings may also be utilized in combination with other repair techniques such as resection, in which a portion of a valve leaflet is excised, the remaining portions of the leaflet are sewn back together, and a prosthetic annuloplasty ring is then attached to the valve annulus to maintain the contracted size of the valve. Other valve repair techniques in current use include commissurotomy (cutting the valve commissures to separate fused valve leaflets), shortening mitral or tricuspid valve chordae tendonae, reattachment of severed mitral or tricuspid valve chordae tendonae or papillary muscle tissue, and decalcification of the valve leaflets or annulus. Annuloplasty rings may be used in conjunction with any repair procedures where contracting or stabilizing the valve annulus might be desirable.

Although mitral valve repair and replacement can successfully treat many patients with mitral valvular insufficiency, techniques currently in use are attended by significant morbidity and mortality. Most valve repair and replacement procedures require a thoracotomy, usually in the form of a median sternotomy, to gain access into the patient's thoracic cavity. A saw or other cutting instrument is used to cut the sternum longitudinally, allowing the two opposing halves of the anterior or ventral portion of the rib cage to be spread apart. A large opening into the thoracic cavity is thus created, through which the surgical team may directly visualize and operate upon the heart and other thoracic contents. Alternatively, a thoracotomy may be performed on a lateral side of the chest, wherein a large incision is made generally parallel to the ribs, and the ribs are spread apart and/or removed in the region of the incision to create a large enough opening to facilitate the surgery.

Surgical intervention within the heart generally requires isolation of the heart and coronary blood vessels from the remainder of the arterial system, and arrest of cardiac function. Usually, the heart is isolated from the arterial system by introducing an external aortic cross-clamp through a sternotomy and applying it to the aorta to occlude the aortic lumen between the brachiocephalic artery and the coronary ostia. Cardioplegic fluid is then injected into the coronary arteries, either directly into the coronary ostia or through a puncture in the ascending aorta, to arrest cardiac function. The patient is placed on extracorporeal cardiopulmonary bypass to maintain peripheral circulation of oxygenated blood.

Of particular interest in the present application are techniques for the repair and replacement of the mitral valve. The mitral valve, located between the left atrium and left ventricle of the heart, is most easily reached through the wall of the left atrium, which normally resides on the posterior side of the heart, opposite the side of the heart that is exposed by a median sternotomy. Therefore, to access the mitral valve via a sternotomy, the heart is rotated to bring the left atrium into an anterior position. An opening, or atriotomy, is then made in the right side of the left atrium, anterior to the right pulmonary veins. The atriotomy is retracted by means of sutures or a retraction device, exposing the mitral valve adjacent to the atriotomy. One of the previously identified techniques may then be used to repair or replace the valve.

An alternative technique for mitral valve access has been used when a median sternotomy and/or rotational manipulation of the heart are inappropriate. In this technique, a thoracotomy is made in the right lateral side of the chest, usually in the region of the fourth or fifth intercoastal space. One or more ribs may be removed from the patient, and other ribs near the incision are retracted outward to create a large opening into the thoracic cavity. The left atrium is then exposed on the posterior side of the heart, and an atriotomy is formed in the wall of the left atrium, through which the mitral valve may be accessed for repair or replacement.

Using such open-chest techniques, the large opening provided by a median sternotomy or right thoracotomy enables the surgeon to see the mitral valve directly through the left atriotomy, and to position his or her hands within the thoracic cavity in close proximity to the exterior of the heart for cannulation of the aorta and/or coronary arteries to induce cardioplegia, manipulation of surgical instruments, removal of excised tissue, and introduction of an annuloplasty ring or a replacement valve through atriotomy for attachment within the heart.

Mitral valve surgery, including mitral annuloplasty, is usually applied to patients with intrinsic disease of the mitral apparatus. As described, above, these patients may have scarring, retraction, tears or fusion of valve leaflets as well as disorders of the subvalvular apparatus. Definitive repair requires direct visualization of the valve.

Patients who develop mitral regurgitation as a result of dilated cardiomyopathy do not have intrinsic mitral valve disease. Regurgitation occurs as the result of the leaflets being moved back from each other by the dilated annulus. The ventricle enlarges and becomes spherical, pulling the papillary muscles and chordae away from the plane of the valve and further enlarging the regurgitant orifice. In these patients, correction of the regurgitation does not require repair of the valve leaflets themselves, but simply a reduction in the size of the annulus and the sphericity of the left ventricle.

Mitral annuloplasty without repair of the leaflets or chordae has been shown to be effective in patients with dilated cardiomyopathy who are refractory to conventional medical therapy. Bolling and coworkers have operated on a cohort of such patients with New York Heart Association Class III and IV symptoms. Average symptom severity decreased from 3.9 preoperatively to 2.0 after surgery. Hemodynamics and ejection fraction improved significantly. Other investigators have achieved similar results as well. However, the morbidity, risks and expense of surgical annuloplasty are very high in patients with cardiomyopathy and congestive heart failure. Thus, a variety of new techniques for the treatment of congestive heart failure are being explored as adjuncts to drug therapy.

Several cardiac restraint devices have been described. U.S. Pat. No. 5,702,343 to Alferness discloses a cardiac reinforcement device that is applied as a jacket over the epicardium in order to limit diastolic expansion. However, this requires an open chest operation to implant and does not directly affect the diameter of the mitral annulus. Another approach is disclosed in U.S. Pat. No. 5,961,440 to Schweich, et al., in which tension members are placed through opposite walls of the heart such that they span the ventricle. Less invasive and "minimally" invasive techniques for valve repair and replacement continue to evolve, both on a stopped heart and on a beating heart. These techniques may provide some benefits over open chest procedures, but they are still attended by significant morbidity and mortality risks.

A need therefore remains for methods and devices for treating mitral valvular insufficiency, which are attended by significantly lower morbidity and mortality rates than are the current techniques, and therefore would be well suited to treat patients with dilated cardiomyopathy. Optimally, the procedure can be accomplished through a percutaneous, transluminal approach, using simple, implantable devices which do not depend upon prosthetic valve leaflets or other moving parts.

SUMMARY OF THE INVENTION

In accordance with one aspect of the present invention, there is provided a medical apparatus for remodeling a mitral valve annulus adjacent to the coronary sinus. The medical apparatus desirably includes an elongate body, having a proximal end region and a distal end region, each of the proximal and distal end regions dimensioned to reside completely within the vascular system. The elongate body is movable from a first configuration for transluminal delivery to at least a portion of the coronary sinus to a second configuration for remodeling the mitral valve annulus proximate the coronary sinus. Additionally, the medical apparatus includes a forming element attached to the elongate body for manipulating the elongate body from the first transluminal configuration to the second remodeling configuration. Preferably, the elongate body comprises a tube having a plurality of transverse slots therein.

In accordance with another aspect of the present invention, there is provided an implant for positioning within a patient. The implant comprises an elongate flexible body, having a proximal end and a distal end, and a longitudinal axis extending therebetween. A first and a second opposing sides extend along the implant body, at least part way between the proximal end and the distal end. The first side has a fixed axial length, and the second side has an adjustable axial length.

At least a first forming element extends through the body to a distal point of attachment to the body. A detachable coupling is provided on the proximal portion of the body, for removably attaching the body to a deployment catheter. Manipulation of the first forming element deflects at least a first portion of the body away from the longitudinal axis.

In one implementation, the body comprises a tubular wall. The tubular wall may be substantially noncompressible along the first side, and provided with a plurality of voids in the wall along the second side. At least some of the voids may comprise slots through the wall, extending generally transverse to the longitudinal axis. Generally, at least about 10, and often at least 20 or more transverse slots are provided. In an alternate embodiment, at least a portion of the tubular body comprises a spring coil.

The forming element may comprise an axially moveable element such as a pull wire. Proximal displacement of the pull wire causes a lateral deflection of the elongate flexible body.

In one implementation, the implant additionally comprises at least a second forming element. Manipulation of the first forming element introduces a first curve in the body, and manipulation of the second forming element introduces a second curve in the body. This allows compound curves to be formed in the implant. Structures are provided for locking the implant in the curved configuration after detachment from the deployment catheter.

In one implementation, distal movement of the forming element causes axial elongation of the second side, thereby bending the implant. In an alternate configuration, proximal movement of the forming element causes axial compression of the second side, thereby bending the implant.

In accordance with another aspect of the present invention, there is provided a multi-zone vascular implant. The implant comprises a tubular body, having a plurality of transverse voids thereon to permit flexing in at least one plane. At least a first, proximal zone and a second, distal zone are provided on the body. A first control element is provided for imparting curvature in the first zone, and a second control element is provided for imparting curvature in the second zone. In one embodiment, a third control element is provided for imparting curvature in a third zone. The control elements may be pull or push wires or rotatable rods or tubes depending upon the flexing or locking mechanism. Retention structures are provided on the implant, for restraining the implant in the curved configuration, within the body of a patient.

In accordance with a further aspect of the present invention, there is provided a deflectable implant. The implant comprises an elongate flexible housing having proximal and distal ends and a central lumen extending therebetween. The housing is flexible in a lateral direction. An axially extending column strength support is provided in the implant. At least a first deflection wire having proximal and distal ends extends along the housing, said wire being secured at a first point of attachment with respect to distal portion of the column strength support. A lock is provided at the proximal end of the housing, for engaging the deflection wire or other component of the device to retain a curve in the housing. The axis of at least a portion of the housing is displaced laterally in response to axial displacement of the deflection wire, thereby causing the distal end of the housing to bend out of the line of the housing longitudinal axis to form a curve in the housing.

In one implementation, the support extends distally to a point within about 2 cm of the distal end of the housing. In one embodiment, the support comprises a portion of the wall of the housing. In an alternate embodiment, the support is distinct from the wall of the housing, and may comprise any of a variety of axially extending column strength supports such as a deflectable metal or polymeric rod or ribbon.

In one embodiment, the deflectable implant comprises a second deflection wire, secured at a second point of attachment in-between the first point of attachment and the proximal end.

Further features and advantages of the present invention will become apparent to those of ordinary skill in the art in view of the detailed description of preferred embodiments which follows, when considered together with the attached drawings and claims.

BRIEF DESCRIPTION OF THE DRAWINGS

FIG. 11A is a segmented view of the device assembly shown in FIG. 10, and shows a partially exploded view of a region of the assembly.

FIG. 11B shows a transverse cross-sectional view taken along 11B—11B in FIG. 11A.

FIG. 12A shows an exploded perspective view of one region of another device assembly according to the invention.

FIG. 12B shows a partially cross-sectioned side view of a region of a device assembly similar to that shown in FIG. 12.

FIGS. 14A–B show a schematic side elevational view of a delivery catheter and implant assembly, respectively, according to the invention.

FIGS. 15A–B show fragmentary side elevational views of a distal end portion of a delivery assembly coupled to an elongate body which is adapted for use according to the device assembly shown in FIG. 14, and show the elongate body during two modes of operation, respectively.

FIG. 15C shows a cross sectional view taken along the line 15C—15C of the elongate body in the mode shown in FIG. 15B.

FIG. 15D shows a side elevational view of the elongate body shown in FIG. 15A.

FIG. 15E shows a cross sectional view taken along line 15E—15E in FIG. 15D, showing a transverse slot pattern.

FIG. 15F shows a cross-sectional view through the line 15F—15F of FIG. 15E of a point of attachment between a deflection element and an elongate body.

FIG. 15G is a fragmentary cross sectional view of a connection between a forming or deflection element and an elongate body.

FIG. 15H shows a fragmentary schematic view of two interlocking segments according to one specific mode for the elongate body shown in FIGS. 15A–F.

FIGS. 16A–B show side elevational views of a distal end portion of a delivery assembly detachably coupled to another elongate body that is also adapted for use according to the device assembly shown in FIG. 1, and show the elongate body during two modes of operation, respectively.

FIG. 16C shows a rear partially cross-sectioned view taken along lines 16C—16C shown in FIG. 16B, and shows in shadow two alternative configurations for the elongate body during the mode of use shown in FIG. 16B.

FIG. 16D shows a side elevational view of the elongate body in the mode shown in FIG. 16A.

FIG. 16E shows a bottom plan view of the device shown in FIG. 16D.

FIGS. 17B–C show side views of the elongate body shown in FIG. 17A, and shows the elongate body during two modes of use, respectively.

FIGS. 17D and 17E show side elevational views of an alternate construction for the implant of the present invention, in a first configuration and a second configuration, respectively.

FIG. 19 is a bottom plan view of an alternative medical device including a delivery assembly, comprising a handle assembly and a shaft, and an implant configured for remodeling a mitral valve.

FIG. 20 is a cross section of the shaft of the medical device of FIG. 19 taken along the view line 20—20 of FIG. 19.

FIG. 21 is an enlarged view of a portion of the medical device of FIG. 19, including the implant and a connection assembly for removably connecting the implant to the delivery assembly.

FIG. 22 is an enlarged view of the connection assembly of the medical device of FIG. 21.

DETAILED DESCRIPTION OF THE PREFERRED EMBODIMENT

Preferred embodiments of the present invention include a method and apparatus for performing mitral annuloplasty and remodeling of the left ventricle using a device that may be introduced percutaneously, and placed within the coronary venous system of the heart. The device exerts compressive force on the mitral annulus and left ventricle, reducing the severity of mitral regurgitation and the size of the left ventricular cavity. The device thus enables reduction of the mitral annulus and constraint of the diastolic expansion of the left ventricle yet without the morbidity and other risks associated with open chest surgery.

The present inventors have determined that the coronary sinus and venis provide an ideal conduit for the positioning of an intravascular prosthesis, or implant, for remodeling the mitral annulus, since they are positioned adjacent the mitral annulus and interventricular septum. The coronary sinus is contained within the atrioventricular groove, and is in close proximity to the posterior, lateral and anterior aspects of the mitral annulus. The coronary sinus and coronary veins are cannulated currently during any of a variety of percutaneous transvenous diagnostic and therapeutic procedures. Permanent placement of pacemaker and defibrillator leads within the coronary sinus and veins is both safe and well tolerated.

The annuloplasty system consists of several components. Desirably, there is a delivery system intended to be introduced percutaneously into a central vein such as the internal jugular, subclavian or femoral veins and to cannulate the coronary sinus. The implant of the present invention is deployed from the delivery system, preferably a delivery catheter, into the coronary venous system. Additional tools may be placed through or along the delivery catheter to position the device, apply elements in place, and to control and/or cut tensioning elements (if provided) from the delivery system, as will be discussed in detail below.

Figure 1:
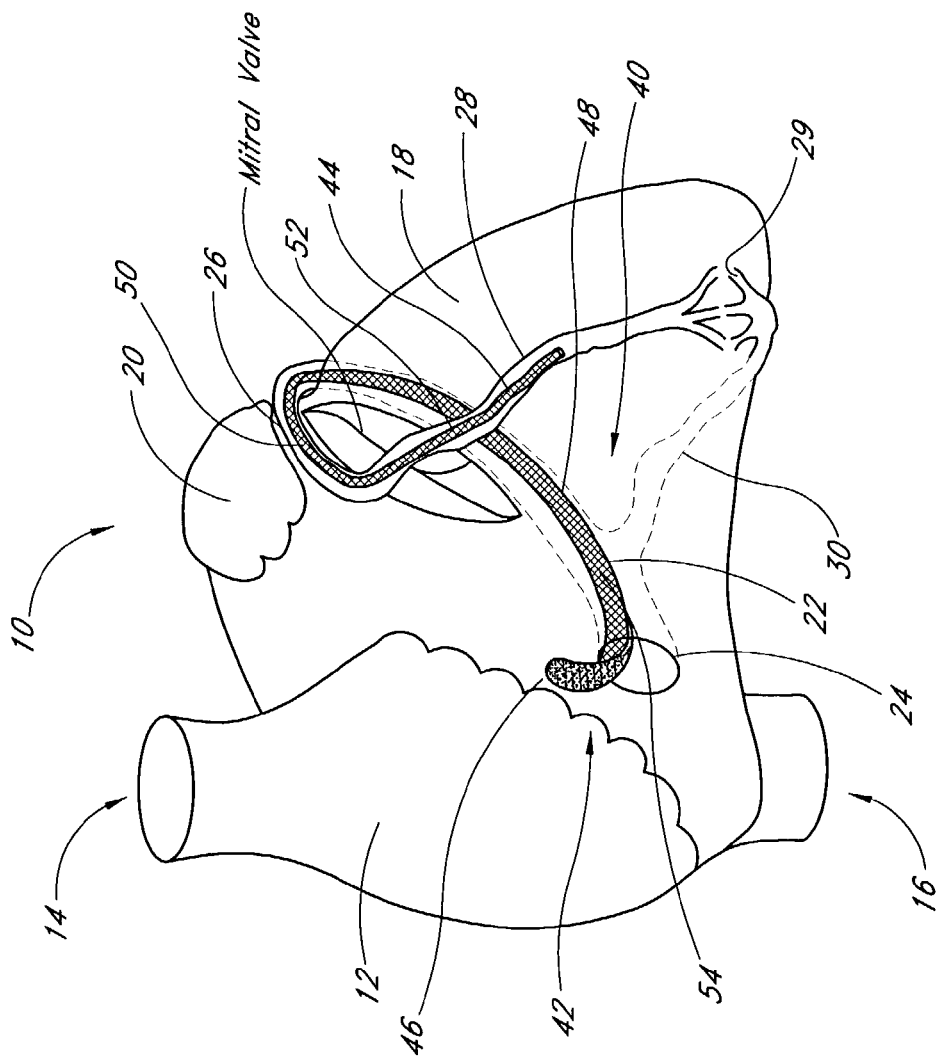
FIG. 1 is a schematic illustration of the heart, showing one embodiment of the mitral annuloplasty device of the present invention deployed within the coronary venous system.

Referring to FIG. 1, there is illustrated a schematic view of the heart 10, having a preferred embodiment of a mitral annuloplasty and cardiac reinforcement device 40 positioned therein. The heart 10 generally comprises a right atrium 12, in communication with the superior vena cava 14 and inferior vena cava 16. The left ventricle 18 is positioned below the left atrial appendage 20. Relevant portions of the coronary vasculature include the coronary sinus 22, which extends from the ostium 24 to the junction 26 of the coronary sinus and the great cardiac vein 28. There may be anastomotic connections 29 between the great cardiac vein 28 and the middle cardiac vein 30, as is well understood in the art.

One embodiment of a mitral annuloplasty and cardiac reinforcement device 40 is illustrated generally in the coronary sinus 22. In particular, the device 40 extends from a proximal end 42 to a distal end 44. The proximal end 42 lies against the posterior aspect of the interatrial septum 46. The midportion 48 of the device 40 is positioned within the coronary sinus 22. The transitional section 50 of the device 40 lies at the junction 26 of the coronary sinus 22 and the great cardiac vein 28. The distal end 44 of the device 40 is lodged in the great cardiac vein 28.

The transitional region 50 is designed to reside in the proximal portion of the great cardiac vein 28. By deflecting out of a plane defined by the coronary sinus 22, it serves as an anchor 52 and prevents the device 40 from slipping out of the coronary sinus 22 when tension is applied. This embodiment of an anchor 52 is, preferably, very flaccid and flexible, thereby minimizing the risk of erosion of the device 40 through the wall of the great cardiac vein or other aspect of the coronary venous system. The proximal end 42 of the device 40 lies outside the ostium 24 of the coronary sinus 22 and is desirably curved upward so as to anchor against the posterior aspect of the interatrial septum 46. Advantageously, the proximal end 42 of the illustrated device 40 is semicircular in shape and elliptical in profile so that no edges will promote erosion of adjacent tissue.

As an alternative anchor 52 to the distal extension of the device 40, any of a variety of structures may be provided. In general, the deployed device 40 will contact the wall of the coronary sinus 22 along the inside radius of its arcuate path. Thus, a tissue contacting surface 54 on the concave side of the deployed device 40 may be provided with any of a variety of friction enhancing surface structures, such as a plurality of transverse ridges, teeth or other projections, or modified surface textures to enhance friction. Alternatively, tissue engaging or piercing structures such as barbs may be provided on the surface 54 to engage the wall of the coronary sinus 22 to resist movement of the device 40.

While use of such structures as anchors may provide some benefit in certain applications, embodiments herein shown and described are believed to be particularly useful in one aspect specifically because they operate without the need for such aggressive tissue engagement. It will be apparent to one of ordinary skill based upon this disclosure that the presently preferred embodiments provide independent device manipulation and shape control that allow for sufficient forces to be applied to the mitral valve without requiring the possibly harmful effects of puncturing and grabbing tissue within the sinus for the remodeling process. In one regard, the independent action of a barbless design allows for adjustment in both the tightening and loosening directions with reduced risk of significant tissue damage or erosion. In another regard, preferred devices 40 according to at least certain embodiments beneficially maintains its length throughout its modified range of shapes while the sinus and adjacent valve annulus reduce their dimensions under the force of remodeling. In still a further regard, the independent action and lack of tissue piercing and grabbing anchors allow for the device to be removed from the patient after initial implantation within the sinus, such as for example in the event of complications or in applications intended to be temporary remedial measures, such as for bridging a patient. Further to this regard, various shapes and sizes of devices may be required in a given patient before the appropriate one is found according to the observed in vivo response to implantation.

The specific dimensions, construction details and materials for the mitral annuloplasty and cardiac reinforcement device 40 can be varied widely, as will be appreciated by those of skill in the art in view of the disclosure herein. For example, dimensional adjustments may be made to accommodate different anatomical sizes and configurations. Materials and construction details can be varied to accommodate different tensioning mechanisms and other considerations.

In general, the device 40 defines an overall length from proximal end 42 to distal end 44. Preferably, the axial length is no more than about 10 cm, and preferably within the range of from about 2 cm to about 10 cm in an embodiment such as that illustrated in FIG. 2 in which the anchor 52 comprises a distal extension of the body 66 for lodging within the great cardiac vein 28. One embodiment of the device 40 includes an elongate flexible body 66 about eight centimeters in length. In such an embodiment, the body 66 is preferably elliptical in cross section so that it will bend in the plane of the coronary sinus 22 and mitral annulus when force is applied to the tensioning element within it, as will be discussed below. Distally the device 40 tapers and transitions to a round cross-section.

Figure 2:
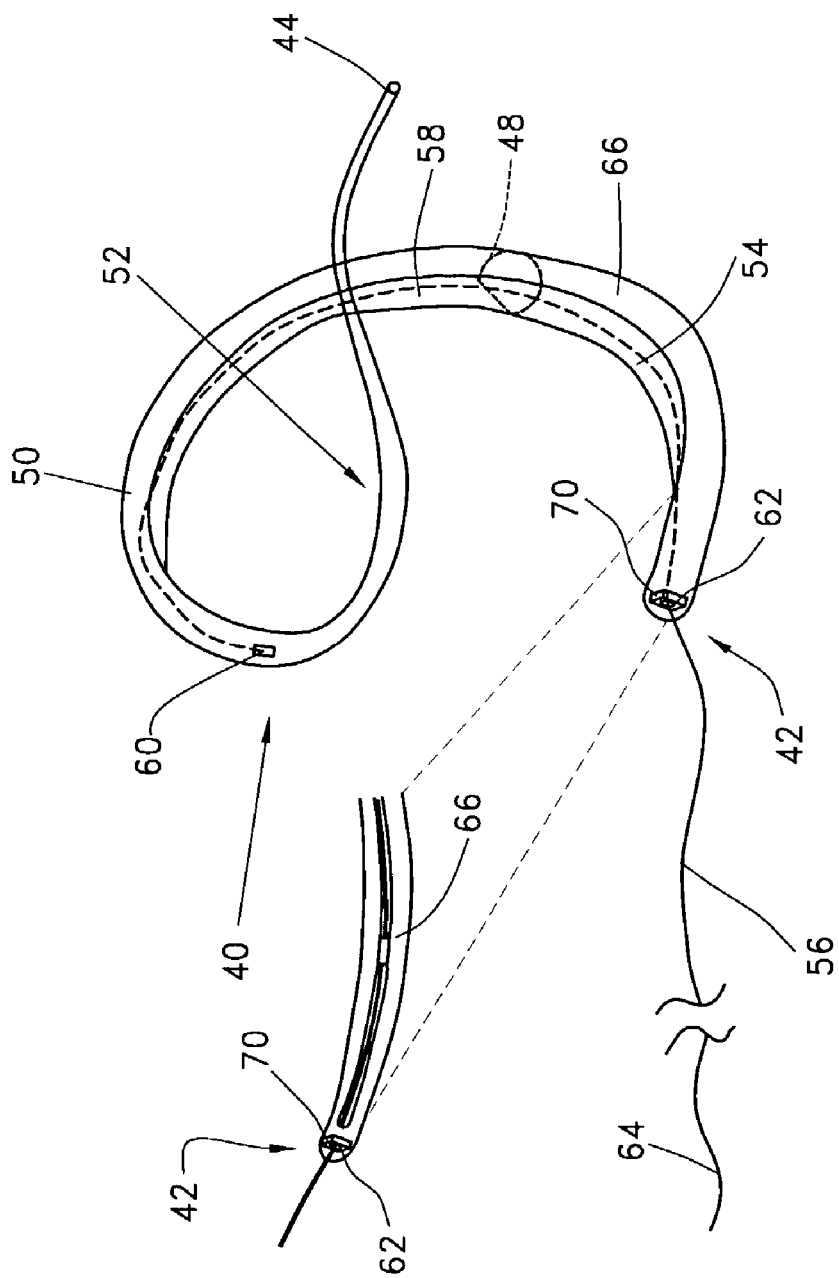
FIGS. 2 and 2A are schematic illustrations of the mitral annuloplasty device shown in FIG. 1.
Figure 2A:
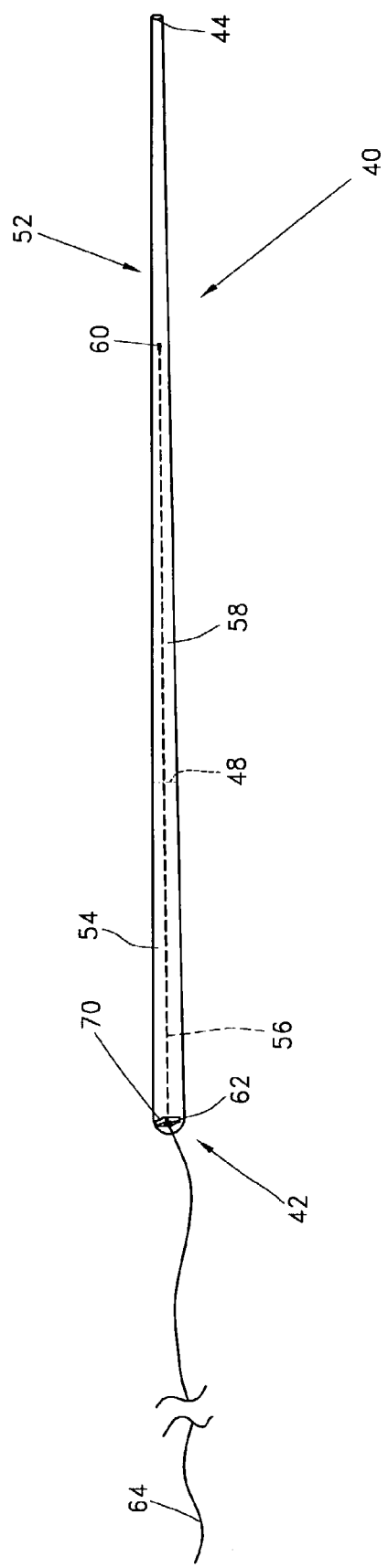

Referring to FIG. 2, there is illustrated an embodiment of the device 40 having a forming element 56, such as a wire, therein. Manipulation of the forming element 56 allows the device to be moved from a flexible orientation to enable percutaneous insertion into the vascular system and navigation into the coronary sinus, to an arcuate configuration for compressing at least a portion of the mitral annulus. The device 40 may be advanced from the first, flexible configuration to the second, arcuate configuration by either axial proximal retraction or distal advancement of the forming element 56 with respect to the body 66, depending upon the particular design.

In general, the device 40 comprises an elongate flexible support 58, extending from a proximal end 42 at least as far as a point of attachment 60. The support 58 may be a portion of the body 66 or may be a distinct component as will be discussed. The support 58 has a fixed length, and is substantially axially non-compressible and non-expandable. Thus, proximal axial retraction of the forming element 56 relative to the proximal end of the support 58 will desirably cause the support 58 to deflect in a first direction, tending to bend the body 66 about an axis transverse to the longitudinal axis of the body 66. Distal axial advancement of the forming element 56 with respect to the support 58 will cause lateral deflection of the support 58 in a second direction, tending to permit the body 66 to straighten due to the inherent resiliency of the support 58. This basic steering configuration can be embodied in many forms, which can be optimized by those of skill in the art to suit a particular construction for the body 66 depending upon the desired dimensions and clinical performance.

The forming element 56 extends from the proximal end 42 through the device 40 to the point of attachment 60. At the point of attachment 60, the forming element 56 is mechanically coupled, and preferably, directly coupled to the support 58. Alternatively, other suitable methods of attachment may be used. A proximal extension 64 of the forming element 56 extends from the proximal end 42 of the device 40, such as through an aperture 62. Proximal retraction of the forming element 56 through the aperture 62 causes the device 40 to bend from an implantation, or delivery orientation, for navigating the coronary vasculature during implantation, to a formed, or remodeling orientation for compression and constraint of the coronary sinus 22 and adjacent structures.

In the formed, remodeling orientation, the device 40 preferably provides a compressive force against the mitral annulus as has been discussed. This is desirably accomplished by forming the device into an arcuate configuration. Generally, the best fit curve of constant radius to which the formed device conforms has a radius within the range of from about 1.0 cm to about 2.0 cm. The forming element may comprise any of a variety of materials and constructions, such as a polymeric or metal wire or strand, a multi-filament braided or woven line, a metal or polymeric ribbon, or other structure capable of retaining the device 40 under tension in the coronary sinus 22.

The device 40 further comprises a support 58, which may be the body 66 of the device 40 or a separate element positioned therein. In an embodiment in which the support 58 is a separate element contained within the device 40, support 58 may comprise any of a variety of generally axially non-compressible elements such as a metal or polymeric wire or column, ribbon, or "bottomed out" (i.e., fully compressed) spring which facilitates lateral bending but inhibits axial compression upon proximal retraction of forming element 56. A metal ribbon comprising stainless steel, nitinol, or other known materials may be desired in certain embodiments, due to its ability to influence the plane of curvature of the device 40 when in the formed orientation.

In the presently illustrated embodiment, the proximal extension 64 of the forming element 56 extends proximally throughout the length of a deployment catheter, to a control or free end which remains outside of the patient during the deployment procedure. Following placement of the device 40 in the coronary sinus, proximal traction on the proximal extension 64 will reconfigure the device 40 into the formed orientation within the coronary sinus, as will be discussed in connection with the method of use of preferred embodiments. After a sufficient tension has been placed on the coronary sinus 22, the forming element 56 is preferably locked in a fixed axial position with respect to the device 40, to resist distal movement of the forming element 56 through aperture 62. Any of a variety of suitable lock arrangements may be provided. Preferably, the lock 70 is provided on or near the proximal end 42, and, in particular, at or about the aperture 62. The lock may comprise any of a variety of structures, such as a suture knot, locking clamp or ring, an interference fit, ratchet and pall structures, an adhesive bond, or a compression fit, as will be apparent to those of skill in the art in view of the disclosure herein.

The lock 70 (on any of the embodiments herein) may be initially disengaged, so that the forming element 56 may be retracted or advanced freely through the aperture 62 while the physician adjusts the tension on the device 40. After the desired tension is achieved, the lock 70 is activated to engage the forming element in a manner which will depend upon the lock design. Alternatively, the lock 70 may be biased into an engaged configuration, such as with ratchet or cam structures, so that the forming element can only be retracted proximally. Preferably, however, the lock will allow the forming element to be released so that the physician can release tension on the device 40 in the event of momentary over tightening.

Figure 7:
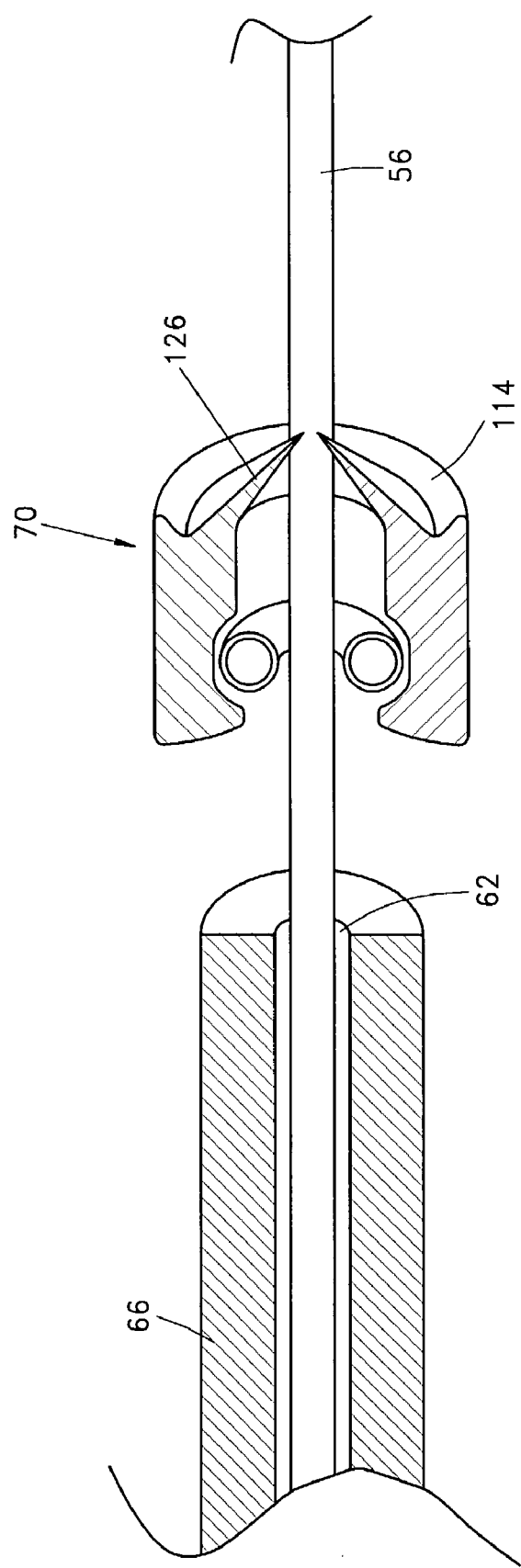
FIG. 7 is a schematic cross-sectional view of one embodiment of a locking device in accordance with the present invention.
Figure 8:
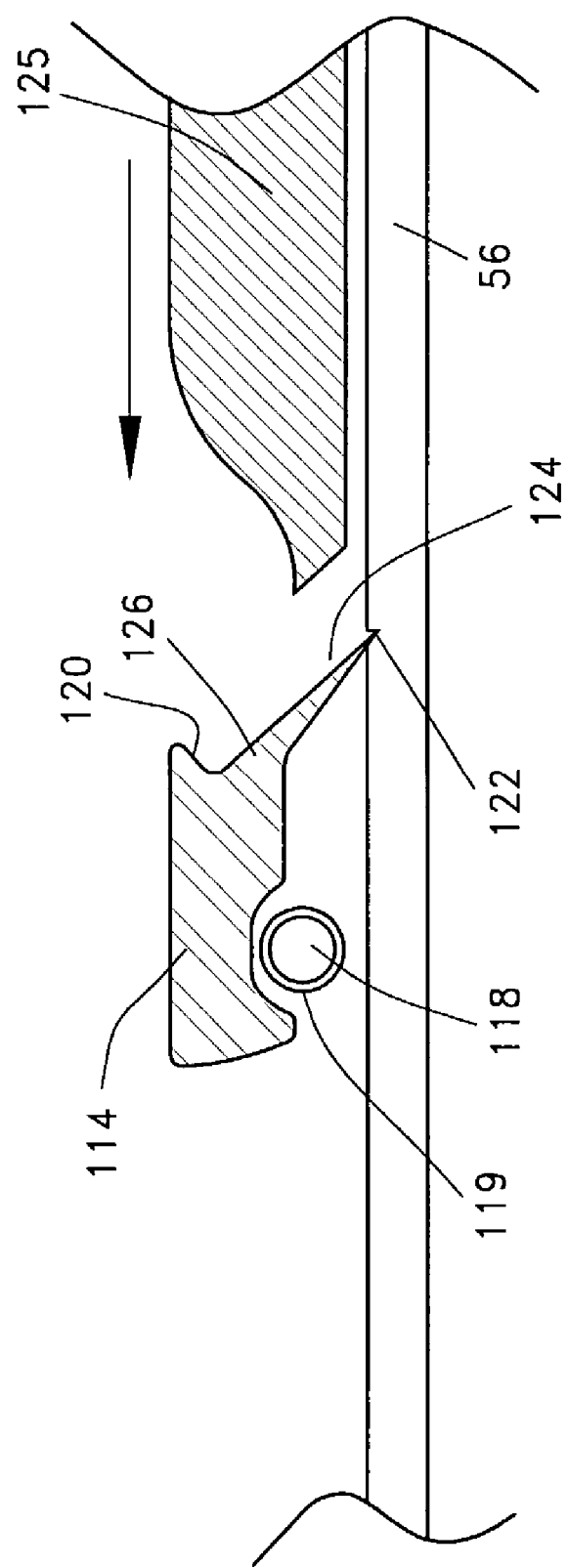
FIG. 8 is a fragmentary view of a portion of the lock illustrated in FIG. 7, with a locking tool.
Figure 9:
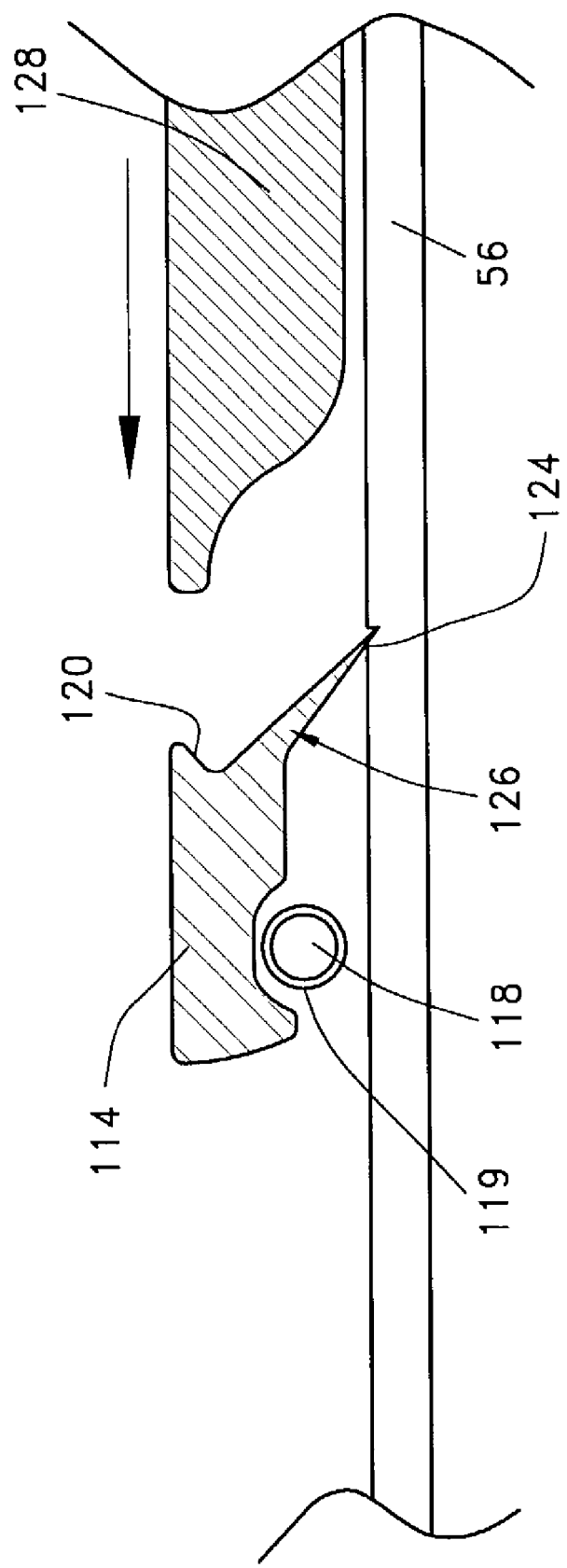
FIG. 9 is a fragmentary view as in FIG. 8, showing an unlocking tool.

Referring to FIGS. 7–9, there is illustrated one preferred embodiment of a releasable lock 70. Although the lock 70 is illustrated as a discrete component of the system, it can alternatively be formed integrally with or attached to the proximal end of the body 66. The lock 70 comprises a body 114, which may be in the form of an annular collar with a central aperture for axial movement over the forming element 56. The body 114 is provided with one or two or three or more releasable locking elements 126, which incline radially inwardly in the proximal direction.

Each locking element 126 is provided with at least one engagement surface 122 for engaging the forming element 56. The forming element 56 may be provided with any of a variety of friction enhancing surface textures or structures to enhance the locking function. Thus, a locking zone along the forming element may be provided with an etched surface or friction enhancing coating. Alternatively, structures such as a plurality of beads or teeth can be provided to permit an interference fit with the engagement surface 122.

The engagement surface 122 is movable between a first, disengaged configuration and a second, engaged configuration. This may be accomplished by pivoting the locking element 126 about a fulcrum 118. In the illustrated embodiment, fulcrum 118 is formed by an annular ring 119. Alternatively, the fulcrum 118 can be formed by plastic deformation of an integral structure, such as a living hinge formed by one or more annular grooves in the body 114, for example.

The locking elements 126 may be biased in the locked direction, unlocked direction, or neutrally. Locking may be accomplished by pressing distally on a locking surface 124, such as with a locking tool 125 (FIG. 8) which applies distal pressure on the ramped locking element 126 at a point displaced radially inwardly from the fulcrum 118. Unlocking may be accomplished by distally advancing an unlocking tool 128 against a release surface 120 displaced radially outwardly from the fulcrum 118. In one embodiment, the locking tool 125 and unlocking tool 128 are conveniently formed from concentric tubular elements as will be apparent to those of skill in the art. The tubular elements, or proximally extending control wires, extend proximally to controls outside of the patient. Alternatively, any of a variety of ramped engagement surfaces and tools can be readily configured to accomplish the lock and/or release functions in view of the disclosure herein.

The length of the device 40 from proximal end 42 through the point of attachment 60 is generally no more than about 10 cm, preferably within the range of from about 2 cm to about 10 cm, and, in one embodiment is preferably within the range of from about 6 cm to about 8 cm. The shape of the device 40 is preferably designed to minimize trauma to the vascular intima, both during implantation and following placement. This may be accomplished by rounding all edges which may come into contact with the vessel wall. Thus, the cross-section through the mid-portion 48 of the device, for example, may be elliptical, semicircular or otherwise rounded, or rectangular with rounded corners. In general, the maximum area of a cross-section of the device 40 will, desirably, be no more than about 15 mm$^2$, and preferably no more than about 10 mm$^2$, for an embodiment desired for implantation within a human adult. In some embodiments, the maximum cross sectional dimension through the apparatus is no more than about 10 mm.

The device 40 may be manufactured in accordance with any of a variety of techniques, which will be apparent to those of skill in the art in view of the disclosure herein. For example, the body 66 may be formed by extrusion, injection molding, or other techniques. In one embodiment, the forming element 56 is secured at point of attachment 60 to an elongate flexible support 58 and co-extruded within a polymeric body 66. Alternatively, a forming element 56 and support 58 subassembly may be positioned within a mold cavity, and injection molded to produce the final device 40. The body 66 may comprise any of a variety of suitable, biocompatible materials such as various densities of polyethylenes, nylon, polyethylene terephthalate, pebax, and others apparent to those of skill in the art.

Alternatively, the forming element 56 and support 58 may be surrounded by a tubular jacket of ePTFE or a polyester fabric such as DACRON, or other material which is wrapped or stitched onto the forming element 56 to produce the final device 40. As a further alternative, the subassembly which includes the forming element 56, and, if present, support 58 may be positioned within a suitable length of tubing formed such as by extrusion. The tubing may be drawn down to a reduced diameter at the distal end 44. Additional post extrusion steps may be used to produce the desired cross-sectional configuration. Manufacturing techniques for the present invention will be apparent to those of skill in the art in view of the disclosure herein.

Any of a variety of additional features may be added to the device 40, depending upon the desired clinical performance. For example, the outside surface of the body 66 may be provided with any of a variety of coatings, such as poly-paraxylene, sold under the trademark PARALENE, PTFE or others to improve lubricity; heparin or other antithrombogenic agents; elastomers such as silicone, neoprene, latex or others to soften the surface and reduce the risk of trauma to the vascular intima, and the like. Adhesion enhancing surfaces may be provided, such as ePTFE patches or jackets, to promote cellular ingrowth for long term anchoring. In addition, depending upon the deployment system design, the body 66 may be provided with a guidewire lumen extending axially therethrough, to allow the body 66 to be advanced distally over a guidewire during placement at the treatment site.

The device 40 may be implanted within the coronary sinus 22 either through direct surgical (e.g. thoracotomy, with or without sternotomy) access, such as in combination with another surgical procedure, via port access, or remotely by way of a percutaneous or surgical cut down access to the venous system. Preferably, the device 40 is implanted in a transluminal procedure, such as by way of a percutaneous access at one of the internal jugular, subclavian, or femoral veins.

Figure 3:
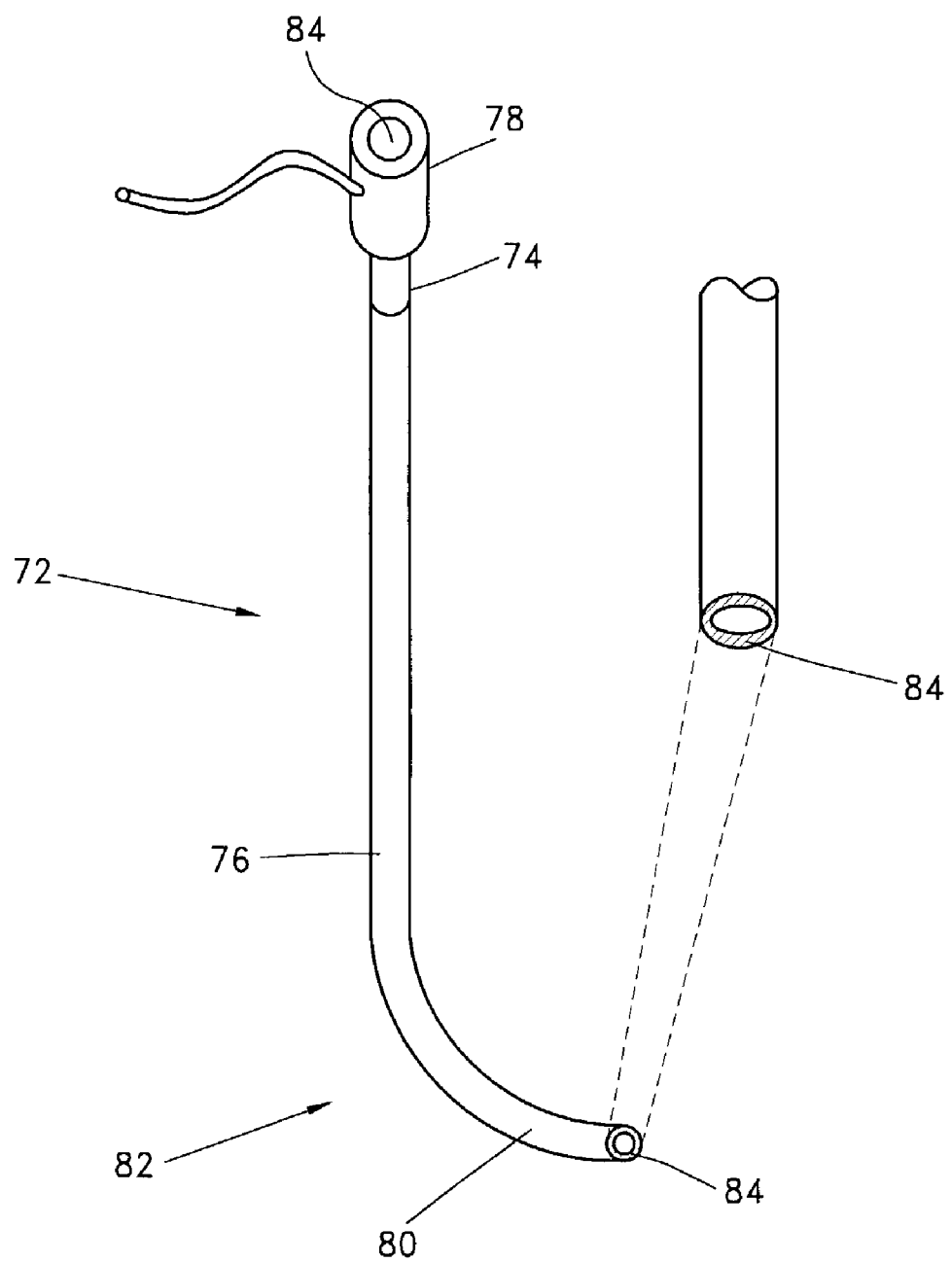
FIG. 3 is an overall view and cross-sectional view through a transvenous delivery sheath.

Referring to FIG. 3, there is disclosed a deployment, or delivery system 72 for deploying the device 40 of the present invention. The deployment system 72 desirably comprises an introducer sheath or catheter 74 for percutaneous venous access procedures. In some circumstances, however, the system 72 includes a first introducer sheath 74 for simply gaining percutaneous access into the vasculature at a remote location from the heart, and a slideably engageable second introducer sheath or guiding catheter is deliverable through such a percutaneous introducer sheath. Introducer sheath 74 has an elongate flexible tubular body 76 extending from a proximal end 78 to a distal end 80. A preset curve 82 is provided near the distal end 80 of the tubular body 76, as is known in the cardiac access catheter arts. At least one lumen 84 extends through the tubular body 76. In one embodiment, the lumen 84 has a noncircular cross section, such as an ellipse having the major axis perpendicular to the plane of curvature of the introducer sheath 74.

Introducer sheaths are well known in the art, and may be manufactured by extrusion, for example, with or without a braided reinforcement structure in the wall. The length and diameter of the introducer sheath 74 may vary considerably, depending upon the dimensions of the device 40 as well as the access point for percutaneous access into the vascular system. For a femoral vein access, for example, the introducer sheath may have a length within the range of from about 80 cm to about 120 cm. Preferably, the outside diameter of the introducer sheath 74 is no more than about 10 French (approximately 3.3 mm).

Figure 4:
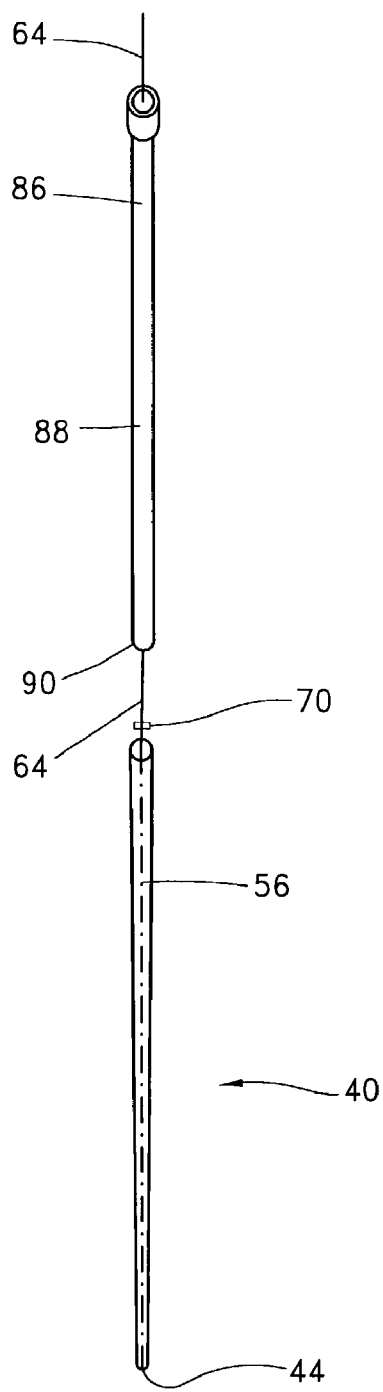
FIG. 4 is a schematic illustration of the delivery sheath and two different embodiments of the implant for extravascular remodeling, one with a forming element and one without.

With reference to FIG. 4, a pusher or dilator 86 as shown provides specific embodiments for a broader aspect that is a delivery member used in an overall assembly for delivering, i.e. advancing or pushing, the device prosthesis into the coronary sinus in a translumenal procedure, as is apparent to one of the ordinary skill based upon the figures and accompanying disclosure herein. Delivery member or dilator 86 has an axial length of from about 10 cm to about 20 cm greater than the axial length of the introducer sheath 74. Dilator 86 has an outside diameter which is less than the inside diameter of the lumen 84, so that the dilator 86 may be freely axially advanced through the lumen 84. The dilator 86 is provided with a central lumen 88, for axially moveably receiving the proximal extension 64 of forming element 56.

When assembled for deployment of a device 40 within the coronary vasculature, a device 40 is positioned within a distal portion of the lumen 84. The dilator 86 is positioned proximal to the device 40 within the lumen 84, and the proximal extension 64 of forming element 56 extends proximally through central lumen 88 of dilator 86. During proximal movement of the introducer sheath 74 with respect to the dilator 86, a distal surface 90 of the dilator 86 resists proximal movement of the device 40. Thus, the device 40 may be deployed from the distal end 80 of introducer sheath 74. In addition, proximal retraction of the proximal extension 64, while proximal movement of the device 40 is prevented by surface 90, causes the device 40 to advance from its deployment configuration to its implanted configuration.

Once the coronary sinus 22 has been cannulated by the introducer sheath 74, the dilator 86 that is loaded over the forming element 56 is advanced through the sheath 74. This is used to push the device 40 to the proper location with the distal tip 44 in the distal portion of the great cardiac vein 28. Using counter traction of the forming element 56 and the dilator 86, the device 40 is curved until the appropriate degree of annular remodeling has been achieved. A locking ring 70 on the forming element 56 that is desirably interposed between the dilator 86 and the device 40 prevents the forming element 56 from slipping distally once the device 40 has been curved. A locking ring 70 that can be released by using a dilator 86 with a different tip geometry may also be employed. After satisfactory deployment and deflection of the device 40, the forming element 56 is cut with a cutting tool (not illustrated) that is desirably placed through the introducer sheath 74.

A second preferred embodiment of the device 40 does not contain an axially moveable forming element. Instead, a core of springy memory material such as nitinol (NiTi) or other suitable materials. The NiTi alloy is pre-formed to have the required configuration. When the device 40 is pushed out of the delivery catheter 74 and into the coronary venous system, the inherent spring force of the preformed core applies the requisite force to remodel the annulus. This embodiment does not require a forming element 56 or a tool to disconnect it from the delivery system. However, the magnitude of force applied to the annulus cannot be adjusted.

Figure 5:
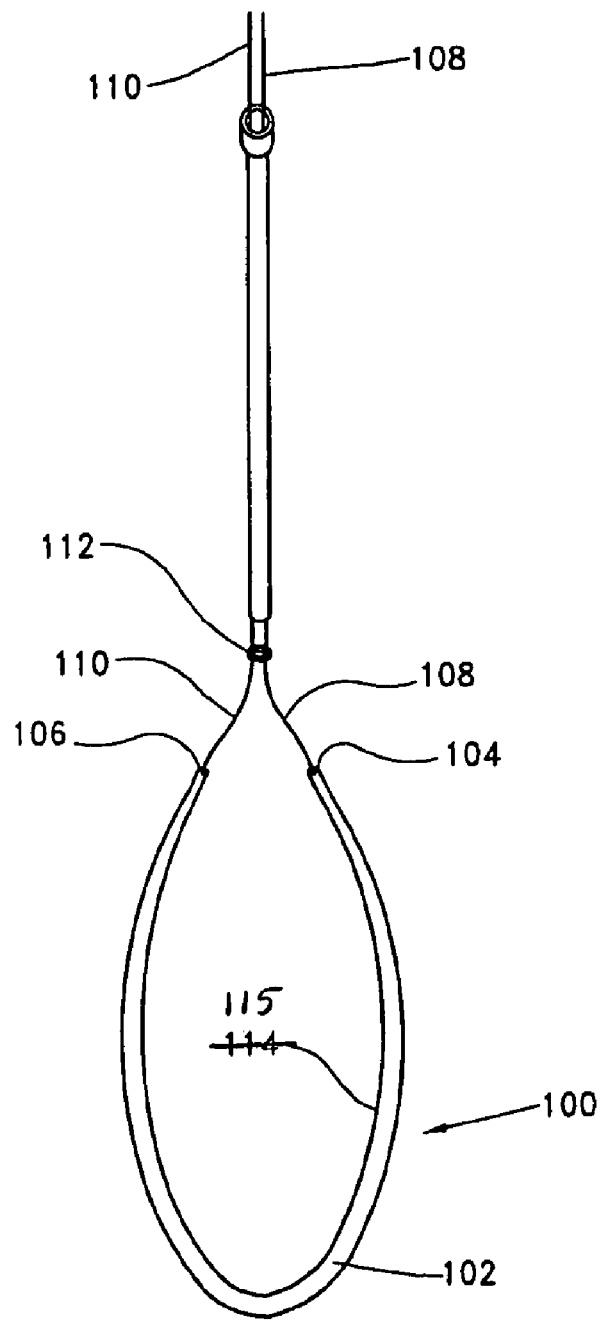
FIG. 5 is a schematic illustration of an alternative embodiment of the present invention positioned in an open-loop configuration through the delivery sheath.
Figure 6:
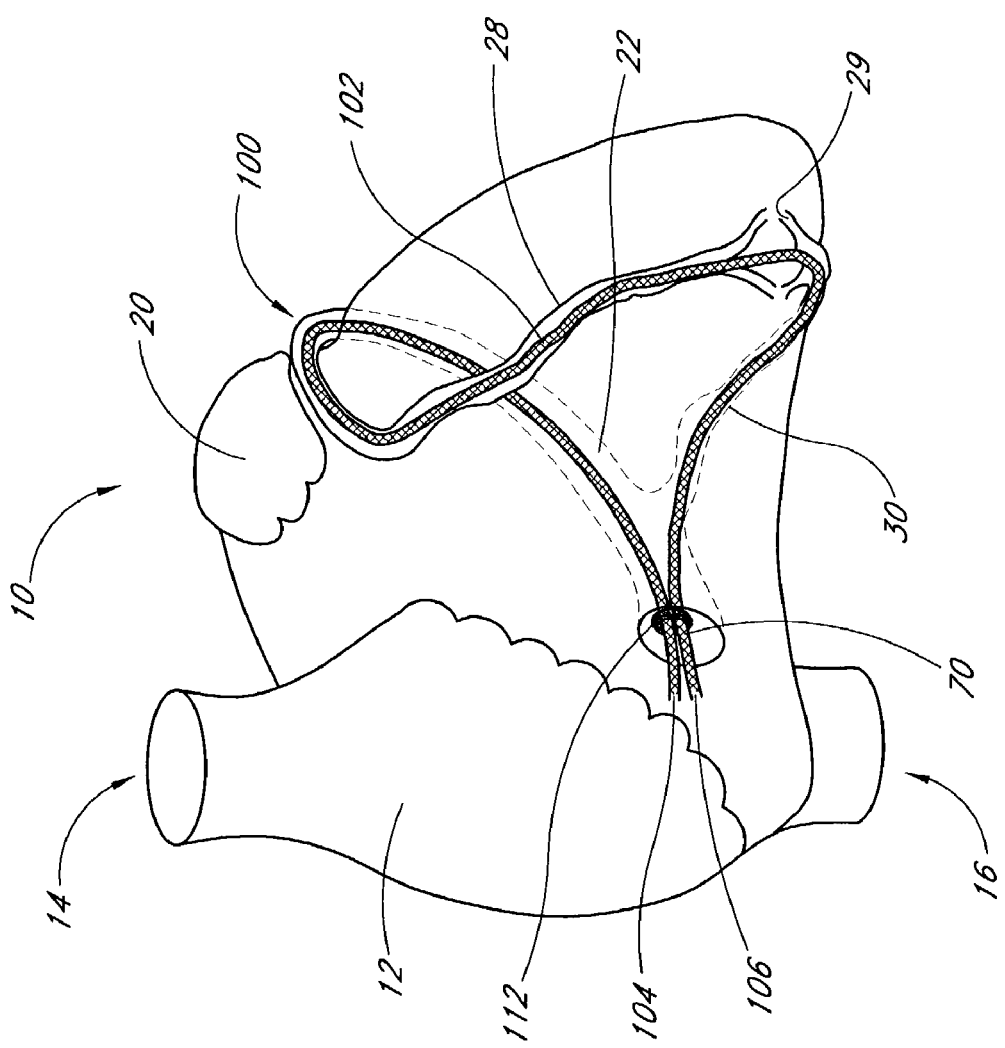
FIG. 6 is a schematic illustration of a heart, having an alternate embodiment of the mitral annuloplasty and cardiac reinforcement device of the present invention positioned within the coronary sinus and contiguous venous system.

With reference to FIGS. 5–6, a third preferred embodiment is deployed as a loop through the coronary venous system, to form a left ventricular girdle 100. The ventricular girdle 100 comprises an elongate flexible body 102 having a proximal end 104 and a distal end 106. A first control line 108 extends proximally from the proximal end 104, and a second control line 100 extends distally from distal end 106. The first and second control lines 108 and 110 may be different portions of the same wire, which extends continuously throughout the length of the body 102. The wire may be a single strand or multi strand component, a length of hypodermic needle tubing, a spring coil, or other structure known in the medical guidewire arts. Preferably, the first and second control lines have a diameter within the range of from about 0.009 inches to about 0.018 inches, although larger diameters may also be used, particularly for the first control line 108.

The distal control line 110 is advanced through an introducer sheath into the great cardiac vein 28 and then through anastomotic connections 29 into the middle cardiac vein 30. Continued advancement results in the tip of the distal control line 110 emerging from the ostium 24 of the coronary sinus 22. The control line 110 is then harnessed with a snare and pulled retrogradially through the delivery catheter as illustrated in FIG. 5. The body 102 is then pulled into the coronary venous system. The body is preferably larger in diameter than the first and second control lines 108 and 100, and preferably elliptical or otherwise noncircular in cross section. This shape enlarges the transverse tissue contact surface area and reduces the risk of erosion when tension is applied to the loop. Both the proximal and distal ends of the loop are threaded through a locking clip 112. A dilator is used to push the clip 112 through the delivery catheter to the level of the coronary sinus ostium 24. Using counter traction on the dilator and the first and second control lines 108 and 110, the clip 112 is cinched on the loop until the requisite degree of tension is produced. Finally, the device is separated from the delivery system using a cutting tool to cut the first and second control lines 108 and 110, and possibly proximal and distal ends 104 and 106 to the extent they extend proximally from clip 112.

The overall length of the embodiment illustrated in FIG. 5 is desirably sufficient so that both of the first control line 108 and second control line 110 can extend outside of the patient, while the body 102 extends throughout the pathway of the ventricular girdle 100, substantially as illustrated in FIG. 6. For a percutaneous femoral vein access, the overall length of the device is preferably at least about 200 cm, and generally within the range of from about 220 cm to about 260 cm. The length of the body 102 from proximal end 104 to distal end 106 is preferably sufficient to form a closed loop as illustrated in FIG. 6. Although both heart size and the shape of the vascular pathway will vary from individual to individual, the length of the body 102 is generally within the range of from about 6 cm to about 12 cm. The body 102 may be injection molded, extruded as a tube, or coextruded over the wire that forms first and second control lines 108 and 110. Preferably, the body 102 either comprises, or is coated with, a material sufficiently compliant to minimize trauma to the vascular intima. In addition, the transverse width of a tissue contacting surface 115 on body 102 is preferably sufficient to distribute compressive force to minimize the risks of localized pressure necrosis within the coronary veins.

Figure 10:
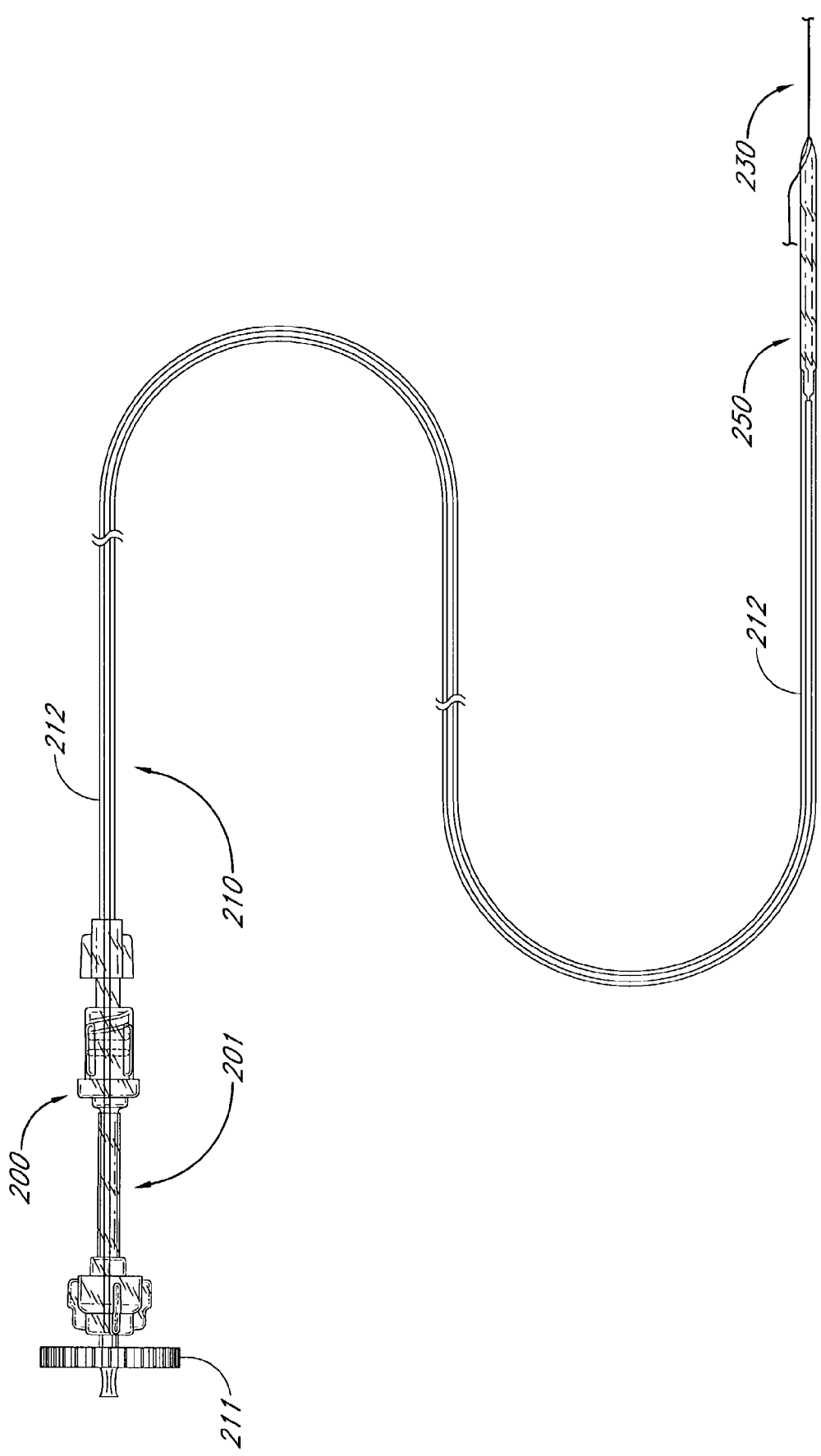
FIG. 10 is a perspective view of another device assembly according to the invention.

FIGS. 10–13B illustrate another particular device assembly 200 that includes various aspects readily adapted for use according to various of the embodiments discussed above. In general, FIG. 10 is an overall view of assembly 200 that includes a delivery assembly 210 engaged to a prosthesis, or implant 250. According to similar overall delivery systems and methods elsewhere herein described, prosthesis 250 is adapted to be delivered in a first condition and shape into a vessel at least in part by manipulation of delivery assembly 210. Once in the desired region of the target vessel, prosthesis 250 is adapted to be adjusted to a second condition and shape within the vessel in order to influence an adjacent tissue structure. As also elsewhere herein described, a particularly beneficial mode of such operation places the prosthesis 250 within a coronary sinus for the purpose of influencing a mitral valve annulus, more specifically in order to influence the shape of the annulus in order to reduce mitral valve regurgitation.

FIGS. 11A–B show the proximal aspects of device assembly 200, and in particular various details for delivery assembly 210 that includes an outer member 215 that is preferably tubular with an inner lumen 216 that is preferably sized to house an inner member 225. Inner member 225 in the variation shown is generally tubular and is substantially free to rotate within lumen 216, preferably by providing rotational force to inner member 225 proximally outside of the patient's body. According to the example shown, this rotational force is applied to inner member 225 via a thumbwheel 205 that is provided on proximal hub assembly 201 coupled to proximal end portion 211 of delivery assembly 210. Thumbwheel 205 is rotationally coupled to inner member 25 within hub assembly 201, which rotational coupling may be achieved according to a number of adaptions as would be apparent to one of ordinary skill.

Rotation of inner member 225 is transmitted into rotation of a rotational coupler 280 that is engaged within a proximal end portion 252 of prosthesis 250 as follows. Inner member 225 has an aperture 228 on its distal end portion that provides a female counterpart of a mated key interface between the inner member 225 and a male counterpart, desirably provided by a shaped proximal end 281 of a rotational coupler 280 that is also rotationally engaged within a proximal end portion 252 of prosthesis 250. The keyed fitting between inner member 225 and rotational coupler 280 allows for transmission of rotational forces to rotational coupler 280. In order to maintain releasable axial engagement of this keyed coupling, a flexible member such as a filament 240 is looped through an aperture 283 through proximal end 281 of rotational coupler 280 with both filament ends 242 and 244 extending proximally through inner member 225 to a location in proximal coupler. The filament 240 is generally held in sufficient tension to keep the distal keyed fitting engaged, though it is further contemplated that the mere presence of the filament may provide an interference against uncoupling if there is a sufficiently tight tolerance in the male/female interface of the keyed fitting.

Rotational coupler 280 is rotationally engaged within proximal end portion 252 of prosthesis 250 through a proximal port, or aperture 251, such that the rotational coupler 280 is adapted to rotate within and relative to the prosthesis 250. This relative rotation is converted to force a deflection of prosthesis 250 into the desired shape of the second configuration in situ as follows.

According to one aspect of the rotational coupling, the prosthesis 250 is preferably held to resist rotation while rotational coupler 280 is rotated within the prosthesis 250. This may be achieved simply by frictional forces of surrounding tissue as prosthesis 250 is delivered into the desired vessel such as the coronary sinus. According to another example, this may be achieved by providing a releasable interface such as a friction fit 218 between outer member 215 and proximal end portion 252 of prosthesis 250 wherein the frictional engagement of outer member 215 and prosthesis 250 are held in a relatively fixed position while inner member 225 and rotational coupler 280 are rotated. This embodiment is shown in FIG. 11A. In addition, or in the alternative to the friction fit interface, a keyed interface may be employed as shown in FIGS. 12A–B. According to this mode, a shaped proximal fitting 253 on the proximal end 252 of prosthesis 250 is adapted to mate as a male counterpart into a shaped aperture or fitting on the distal end 212 of outer member 215. This keyed interface allows for rotational coupling between the members in a similar manner as just described for the inner member 225 and rotational coupler 280, and may allow for a more releasable coupling with reduced friction upon axial detachment of the members.

Figure 13A:
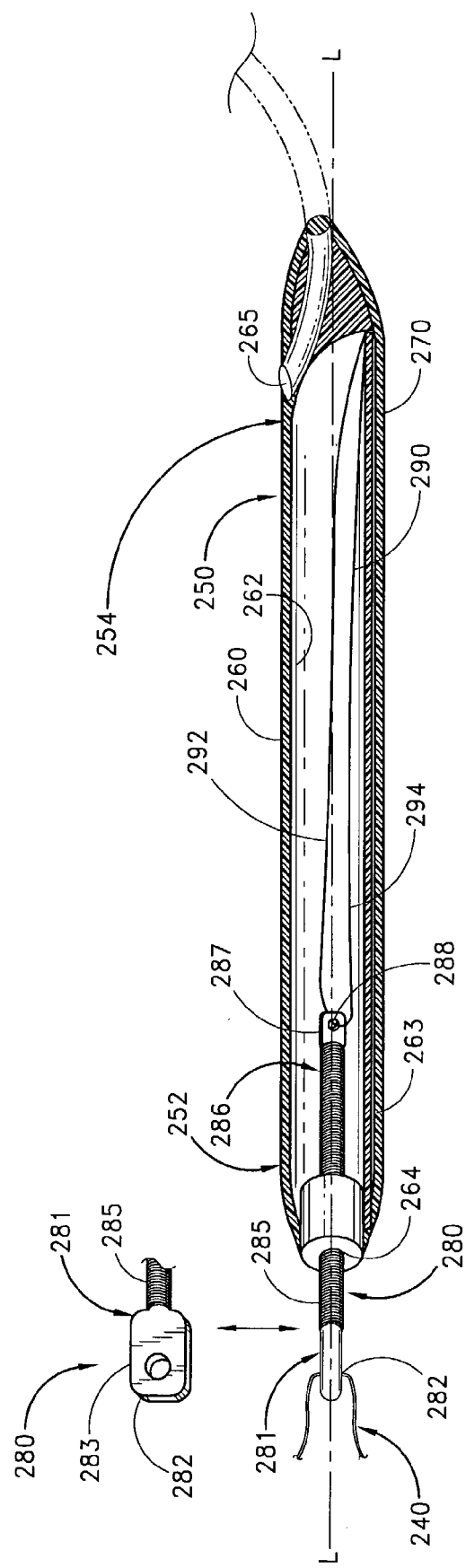
FIG. 13A shows a partially cross-sectioned exploded side view of a distal prosthetic implant region of a device assembly similar to that shown in FIG. 10, and shows the distal prosthetic implant region in a first configuration during a first mode of use.
Figure 13B:
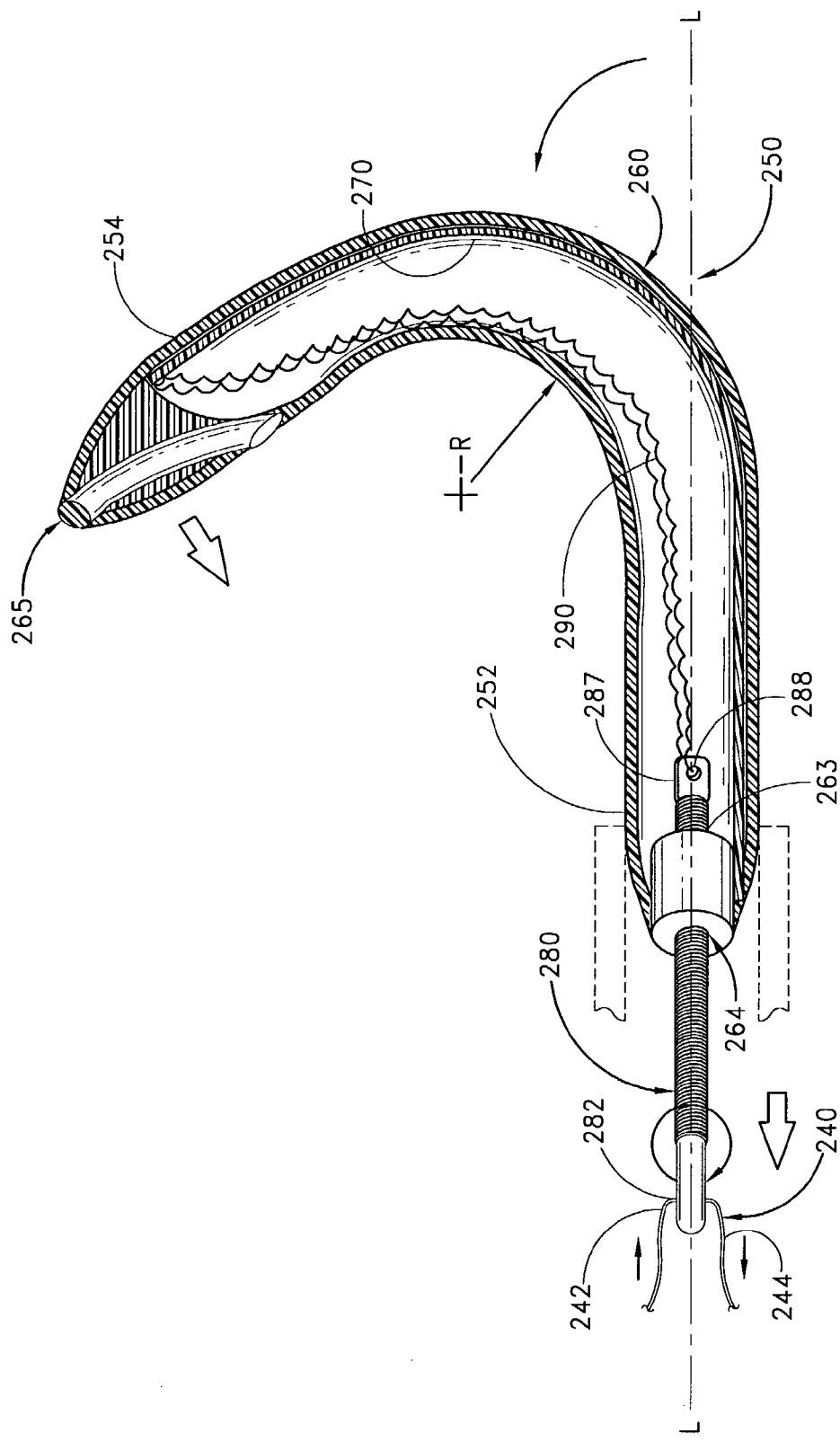
FIG. 13B shows a similar view as that shown in FIG. 13A, and shows the distal prosthetic implant region in a second configuration during a second mode of use.

According to another aspect, the rotational forces from rotational coupler may be converted to deflection forces on the prosthesis 250 according to one example as illustrated in the specific illustrative embodiment of FIGS. 10–13B, and in particular detail in FIGS. 13A–B. Prosthesis 250 includes a generally tubular wall or body 260 that has an inner lumen 262 and extends from the proximal end portion 252 to the distal end portion 254 of prosthesis 250. Secured along proximal end portion 252 is a nut fitting 263 that has a grooved inner bore 264 which communicates with inner lumen 262. Further to this specific embodiment, rotational coupler 280 is a screw member with outer helical threads 285 engaged within the mating threads of an inner surface (not shown) of a bore lumen such that a distal end of screw member 285 extends distally within lumen 262 and terminates at a second key fitting 287 similar to the shaped proximal end portion 282 and also having an aperture 288. Similar to the proximal end of rotational coupler 280, another flexible member or filament 290 is looped through aperture 288 such that two arms 292,294 extend distally therefrom to an attachment point along distal end portion 254 of prosthesis 250. Because nut fitting 263 is fixed in relation to outer tubular body 260, and because that tubular body is held relatively fixed position as provided above, rotation of rotational coupler 280 moves coupler 280 proximally relative to body 260. This proximal axial translation of rotational coupler 280 puts tension on filament 290, which puts tension on the body 260 due to the distal attachment. This tension on outer body 260 forces a deflection of the body 260. Therefore, rotational force is converted into a tensile force which, in turn, causes radial deflection of the body 260 relative to the longitudinal axis L of the device 250. In other words, the body 260 is deflected about an axis that is transverse to the longitudinal axis L.

The forced deflection described immediately above may be controlled in a particular plane by providing a composite structure within prosthesis 250 that is engineered to respond, i.e. yield, to these forces in a prescribed way. In the specific desirable embodiment shown, a relatively rigid spine member 270 is provided within lumen 262 of outer tubular body 260. This spine member 270 is more rigid and more resistant to axial forces, especially tensile forces, than the material of outer tubular body 260 alone. Therefore, providing spine member 270 along only one radial position along the circumference of the prosthesis 250 creates a bias on the device 250 to deflect away from the spine 270 toward a more compressive region of the device 250. Such composite design may further include a laminate structure, a composite structure—such as an imbedded wire reinforced wall structure, or may be achieved by engineering material variations in the device, such as for example by thinning, thickening, hardening, or softening the material at one location along the outer tubular body 260 relative to another region to urge the body 260 to deflect at a desired location.

As may be achieved by other controllable embodiments elsewhere herein described, deflection according to the present embodiment may be adjusted according to a healthcare provider's desires, and is adjustable in either direction—by either tightening the radius of curvature R or opening it. According to this specific embodiment however, the adjustability of and choice between tightening and loosening of the deflection depends upon the direction and extent of rotation placed upon the rotational force transmission system.

In any event, once the desired deflection is achieved and desired therapeutic results are observed, the prosthesis 250 may be detached from the delivery assembly 210 by severing the torque or rotational force transmission system at the keyed fitting between the inner member 225 and the rotational coupler 280. This is accomplished by first releasing at least one arm 242, 244 of the proximal filament 240 while withdrawing the other arm, thereby threading the filament 240 through aperture 283 (as shown in bold arrows in FIG. 13B) until it is unthreaded completely from the aperture 283. This allows inner member 225 to be withdrawn proximally from rotational coupler 280 to detach and thereby implant the prosthesis 250.

Alternatively, as with other adjustable deflection systems herein described, the prosthesis may be held in its therapeutic condition for a temporary period of time (which may nevertheless be prolonged during a hospital stay), during which time mitral valve regurgitation may be minimized, such as for example for the purpose of bridging the patient in a temporarily improved condition until other treatments may be performed, e.g. annuloplasty, valve surgery, heart transplant, etc. In this alternative temporary setting, at the appropriate time the deflected, contracted prosthesis may be adjusted back open from its cinched position around the valve, and then withdrawn without implantation by withdrawing the entire system, delivery assembly still engaged to the prosthesis. Moreover, it is further contemplated that such a temporary prosthesis may be modified to remove the detachment mechanisms herein described, which may provide for a simpler and lower cost device.

Device assembly 200 is also shown in various of the FIGS. 10–13B to include a distal guidewire tracking member with a guidewire lumen 265 which is adapted to slideably engage a guidewire 230 in order to be placed in a percutaneous translumenal procedure into the desired vessel location, such as within the coronary sinus 22. The particular guidewire lumen shown is integral within the distal aspects of prosthesis 250 as a "rapid exchange" or "monorail" design that allows for relatively independent movement of the guidewire and catheter in vivo. Moreover, this design removes the need for the guidewire to ride coaxial through the entire device assembly 200, as would be the case for example in an "over the wire" type system. The type shown beneficially allows for detachable engagement of prosthesis 250, which is preferably achieved after withdrawing the guidewire 230 from the distal lumen 265.

In each of the foregoing implantation methods, the physician preferably monitors the degree of regurgitation during the step of tightening the implant. Although any reduction in mitral regurgitation may be desirable, regurgitation is preferably reduced to something less than moderate (less than 2+). In any event, at least a one grade reduction is preferably achieved. On the other hand, reconfiguration of the implant 250 is desirably not accomplished to an extent sufficient to produce mitral stenosis, or any flow limitation of hemodynamic significance.

Thus, the method of implantation preferably further comprises the steps of monitoring the degree of mitral regurgitation during, and preferably also before and following the implantation and/or reconfiguration steps. The degree of mitral regurgitation may be monitored such as by transesophageal echo cardiography, intracardiac echo cardiography, fluoroscopy using radiocontrast in the left ventricle (LVgram), or left atrial or pulmonary capillary wedge pressure tracings, as are understood in the art, during the incremental restriction of the mitral annulus and/or left ventricle step. Once a sufficient reduction in regurgitation has been achieved for a particular patient in the physician's judgement, the device 250 may be locked and the delivery assembly 210 detached from the device 250 and removed from the patient.

The method may additionally comprise the step of measuring the coronary sinus 22 and/or other coronary vein, and selecting an appropriately sized implant 250 from an array of implants of varying sizes. Such parameters may include diameter, length, or radius of curvature of the arc of the sinus. The appropriately sized implant 250 is thereafter positioned within the target vein. The implant 250 is thus preferably provided in a graduated array of sizes, so that the optimal size can be selected for each patient. The size of the coronary sinus 22 or other vein can be measured using any of a variety of techniques, such as echo cardiogram, MRI, CT Scan, or angiography as is understood in the art. Moreover, as is apparent to one of ordinary skill, measuring a parameter of the coronary sinus 22 generally provides indicia of certain parameters of the mitral valve and its annulus, such as for example mitral valve diameter, in which case either the coronary sinus parameter or the mitral valve parameter may provide the requisite information for choosing an appropriately dimensioned device 250 from the kit.

It follows that such mitral valve parameters may further be measured directly, such as by various of the methods just described, in order to generate the values used for choosing the appropriate device 250. Once a parameter for an anatomical feature is measured as herein described, its value is generally estimated according to the accuracy of the respective measuring tool—it is contemplated that persons without specialized medical skills or training can choose the appropriate medical device 250 from the kit once armed with this estimated value. For example, packaging for each device 250 of the kit may indicate the respective dimensions that are unique to that device 250 with respect to other devices of the kit, and the estimated value of the measured anatomical parameter may simply be compared.

It is contemplated and apparent that various of the embodiments herein described are adapted to accomplish manipulation of the coronary sinus 22 for mitral annulus reduction without substantially altering the length of the device 250 within the sinus 22. This may provide a benefit by increasing the useful purchase of the device 250 along the coronary sinus 22 and circumferentially around the mitral annulus as the sinus length and/or annulus diameter may be reduced during remodeling from the radial deflection of the prosthetic device 250. This may also mean that the dimension of the device 250 in a kit of devices may not directly correspond to the estimated value of the anatomical parameter that is measured. For example, the compared value of the measured device parameter may be shorter than an estimated coronary sinus 22 length due to a possible shortening of the sinus 22 during device 250 treatment. Or, the anatomical parameter may be estimated from an initial value based upon an anticipated or desired final result from treatment and such procedurally related value be used for choosing the appropriate device (e.g. comparing an estimated final length of the sinus or mitral valve diameter with a known dimension of the device in the remodeling configuration when used in situ).

As a further aspect to the present invention, the implant 250 is preferably combined with an appropriate drug therapy for treating congestive heart failure. Residual regurgitation and other hemodynamic functions are preferably measured following implantation of the implant of the present invention. Heart medications are preferably adjusted to take into account the reduction in regurgitation and/or reduction in left ventricle volume in formulating an ongoing drug therapy for the patient.

Still further, the present invention contemplates temporary use in the sinus 22 for mitral valve remodeling as a bridging regime in combination with other permanent treatments such as more conventional annuloplasty or valve replacement via surgery. Such combined systems of devices 250 and respective methods of use, which may further be combined with the pharmaceutical drug regimes, provide an overall treatment regime that provides a highly beneficial result for management of patients with harmful mitral valve regurgitation.

In accordance with a further aspect of the present invention, there is provided a method of constricting the left ventricle. Left ventricular constriction may be desirable in patients without mitral regurgitation. One implementation of this method comprises implementing the ventricular girdle 100 as illustrated, for example, in FIGS. 5–6 and previously discussed herein.

Any of the embodiments discussed herein may additionally be provided with one or more externally facing electrically conductive axially extending strips or annular bands, to enable the device 40 to function additionally as a cardiac pacing or other diagnostic or therapeutic cardiac electrode. The electrically conductive band or bands are placed in electrical communication with a pacing source or diagnostic instrument by way of one or more electrical conductors extending away from the device 40. The conductors may be electrically connected to any of a wide variety of electronic cardiac rhythm management devices, which are well known in the art.

In accordance with another aspect of the invention, a medical device system 300 having a medical device 301 with a delivery assembly 310 with a proximal end portion 312 and a distal end portion 314 that is releasably coupled to a proximal end portion 322 of an implantable prosthesis, shown in FIG. 14A as an elongate body 320. Delivery assembly 310 (FIG. 14A) is adapted to at least in part deliver elongate body 320 into the coronary sinus while elongate body 320 is in a first configuration, such as is shown in the embodiment of FIG. 15A. In particular, delivery assembly 310 is adapted to position elongate body 320 into the sinus in a percutaneous, translumenal procedure by manipulating proximal end portion 312 externally of the patient's body.

More specifically, system 300 further includes a delivery system 302 with a delivery catheter 304 that provides percutaneous translumenal access from an introduction site into the peripheral vasculature of the patient (not shown) into the coronary sinus, and preferably has a shaped distal end portion 305. Delivery catheter 304 includes a distal port 306 through which an internal passageway (not shown) within the delivery catheter 304 is adapted to deliver device 301 into the coronary sinus. An additional introducer sheath 303 may also be provided in order to allow for percutaneous access into the vasculature at the introduction site.

As shown in one embodiment in FIG. 15B, once in the coronary sinus the elongate body 320 is adapted to be adjusted from the first implantation (flexible) configuration to a second (relatively rigid) remodeling configuration that has a shape that is adapted to remodel the mitral valve annulus. According to the embodiment shown in FIG. 15B, this shape is generally adapted to provide an external force onto the annulus in order to reduce its diameter along at least one transverse axis, such as according to the arcuate shape shown that at least in part grips down onto a portion of the circumference of the valve to provide a diameter reducing force. As is also shown in phantom, the arcuate shape may take different forms in terms of degree, and in a further highly beneficial application is controllable and selectable between various or through a continuous range of degrees. Such controllability according to the embodiment shown is also selective between intermediate deflectable portions 360, 370, 380, as is shown in FIG. 15B and will be further developed below.

FIG. 15C illustrates a feature related to the deflection mode of operation for the embodiment shown in FIGS. 15A–B and with further reference to the increased detail shown in FIGS. 15D–H. More specifically, elongate body 320 is constructed in a manner that is shown to substantially isolate deflection in the second configuration along one reference plane while substantially preventing deflection or bending out of that plane. This is accomplished according to the embodiment shown as follows.

Elongate body 320 is constructed from tubular wall 325 that extends continuously along the length of the deflectable portions 360, 370, 380 of the elongate body 320. An array or plurality of distinct, discontinuous slots or voids 330 are formed within the wall 325, each void 330 having an elongated shape that is transverse to the longitudinal axis.

By further reference to the specific embodiment of FIGS. 15A–G, transverse voids 330 have a central groove-shaped region with two adjoining portions 332, 334 that converge at an apex 333 along the longitudinal axis. Such a shaped void 330 is defined at least in part by two opposing shaped surfaces of two adjacent, longitudinally opposing portions 340, 350 of the wall of the elongate body 320. One of these portions 340 desirably assumes a convex shape and the other portion 350 is desirably concave around the apex 333. These shaped surfaces 340, 350 are preferably in a nested configuration with the convex portion 340 positioned within the concave portion 350. In this arrangement, lateral movement of one of the adjacent wall portions 340, 350 relative to the other portion 340, 350 is substantially prevented by a mechanical interference. This is illustrated in FIG. 15E wherein the relative nesting of adjacent portions 340, 350 of the elongate body 320 provides a mechanical interference to radial deflection along a first plane (in the plane of the page) and substantially isolates deflection of the elongate body 320 along a second plane (perpendicular to the plane of the page) upon application of axial bending forces. In FIG. 15C, bending is restrained in the plane of the page. This is in contrast to the embodiment depicted in FIG. 16C, described below.

FIG. 15E shows grooved voids 330 in their entirety for the purpose of simplifying the illustration for better understanding. However, as depicted in FIG. 15D and by reference to FIG. 15F, these transverse voids 330 (and generally the entire V-shaped portion herein described in detail) span across at least about 180 degrees of the circumference of the elongate body 320. Preferably, the transverse voids 330 span across more than about 300 degrees of the circumference of the elongate body 320, and still more preferably the voids span across between about 300 degrees and about 315 degrees of the circumference. By arranging such grooved voids in a similar alignment around the circumference of the tubular wall 325, an integral and continuous backbone or spine 327 (FIG. 15F) is formed along wall 325 that runs axially along the length of the elongate body 320. This overall arrangement of voids 330 and spine 327 has been observed to provide a desirable combination of bendability, due to the voided pattern, and axial integrity, due to the remaining wall structure.

The elongate body 320 shown in FIGS. 15A–G generally has three deflectable portions 360, 370, 380 along the longitudinal axis. Each deflectable portion 360, 370, 380 has a group of voids 330 as just described in order to be individually deflectable between the first and second configurations with an applied force from outside of the patient's body while the elongate body 320 is positioned within the coronary sinus. More specifically, three forming elements 365, 375, 385 are coupled to the three deflectable portions 360, 370, 380 in order to apply a deflection force to that portion to reshape that portion between the first and second configurations. Each forming element 365, 375, 385 is preferably adapted to extend externally from the patient's body when the elongate body 320 is positioned within the coronary sinus in order to be manually manipulated to apply the deflection force to the respectively coupled deflectable portion 360, 370, 380. Deflection of each of these portions combined provides for the overall shape for the elongate body 320 in the second configuration.

Forming elements 365, 375, 385 are attached to elongate body 320 at unique, longitudinally spaced points of attachment 361, 371, 381, respectively, that are each at or distal to the distal end of each respectively coupled deflectable portion 360, 370, 380 (see FIG. 15E). One beneficial application is shown for the attachment of the forming members 365, 375, 385 to the body 320, wherein each point of attachment 361, 371, 381 has two axially spaced apertures, which are shown as proximal and distal apertures 362, 363 for point of attachment 361, proximal and distal apertures 372, 373 for attachment point 371, and proximal and distal apertures 382, 383 for point of attachment 381. As illustrated for point of attachment 371 in FIG. 15G. a shaped distal end 377 for forming element 375 is sized to be seated within distal aperture 373 where it is secured by a securing agent 374 which may be an adhesive, melt bond, or solder, for example. Any or all of the respective forming elements 365, 375, 385 may also be welded through the apertures to the wall. Forming element 375 extends proximally from distal aperture 373 and is further secured to wall 325 by additional securing agent 374 introduced through proximal aperture 372. The securing agent 374 may be applied in one operation from outside in through both apertures 372, 373. In addition, distal end 377 may also be shaped to provide a mechanical securement means for attachment during proximal axial forces, such as is shown in phantom in FIG. 15G.

According to one specific embodiment that has been observed to be useful, the apertures for this attachment embodiment are generally between about 0.020 inches and about 0.022 inches in diameter with similar longitudinal spacing, and the distal end for the seated forming elements is between about 0.012 and about 0.014 inches in diameter. Further to that embodiment, wall 325 is generally constructed from a tubular, stainless steel wall or hypotube with a plurality of grooved voids 330 formed therein according to a pattern similar to that shown and described by reference to FIGS. 15D–F. The respective forming elements are soldered to the respective attachment points using gold/tin solder. Further to this useful embodiment, grooves such as shown and described by reference to FIGS. 15A–G were formed in the underlying stainless tube by laser cutting, though other well known techniques such as hand grinding, mechanical cutting, photo-lithography, etc. may alternatively be used.

As previously described herein, the applied force from the forming elements 365, 375, 385 is generally an axial force between the attachment points 361, 371, 381 to the elongate body 320 and a proximal location (not shown) along the elongate body 320 that is proximal to that deflectable portion. According to the specific embodiments shown this force is generally between the attachment points 361, 371, 381 and the proximal end portion of the elongate body 320. The elongate body 320 may generally be held during forced deflection by means of a holding device (not shown) in order to substantially fix the proximal end portion of the elongate body 320 relative to the deflectable portion so that the axial force may be applied between those portions in situ. While the proximal manipulation of the forming elements 365, 375, 385 in order to apply the deflection force to the deflectable portions 360, 370, 380 may be axial as just described, it may in another regard be rotational.

Each deflectable portion 360, 370, 380 is substantially axially rigid and non-compressible relative to the longitudinal axis L, and therefore the overall axial length of elongate body 320 remains substantially constant between the first and second configurations. However, each deflectable portion is relatively flexible along a radial axis transverse to the longitudinal axis such that the deflectable portion is adapted to bend radially upon application of an axial force between a distal location on the elongate body at or distal to a distal end of the deflectable portion and a proximal location along the elongate body 320 proximal to that deflectable portion. In one regard, the elongate body 320 may be generally axially non-compressible or non-expandable between each deflectable portion 360, 370, 380 and the proximal end portion of the elongate body 320, such that each deflectable portion 360, 370, 380 is adapted to bend radially upon application of a compressive or tensile axial force, respectively, on the elongate body 320 between the distal location and a proximal location that is at the proximal end portion of the elongate body 320.

In still a further regard, other constructions for elongate body 320 may also provide for the combination of an integral and continuous wall 325 from the proximal end portion to the distal end portion of the body and a controlled radial bending response to axially compressive or tensile forces. In addition or in the alternative to the continuous integral wall incorporating the formed voids 330, the wall 325 may also include an engineered composite support structure with engineered support elements that are arranged to control the spacial strain response to the stress of the applied forces. Other suitable shapes for voids 330 may also be acceptable.

One particular variation of the patterned voids according to the nested V-pattern embodiment shown in FIGS. 15A–G is shown in FIG. 15H, wherein the nested adjoining portions 340, 350 include interfacing surfaces 342, 352 that have interlocking teeth 344, 354 which are adapted to be locked in a radially deflected pattern in the second configuration. More specifically, the interfacing pattern of teeth 344, 354 is adapted to perform like a ratchet mechanism. By positioning this region along an inner radius of curvature during the bending of forced deflection, compressive forces bring the convexly shaped tooth region 340 deeper into the fitted well formed by the concave receiving region 350. This motion provides an interference between teeth 344, 354 that deflects portion 340 until further motion toward portion 350 clears tooth 354 and recovery locks tooth 344 behind 354. This interactive motion of adjacent portions in voided regions is further represented by bold arrows in FIG. 15H.

Another example of modified void patterns, and therefore differentiated functionality, is provided by reference to FIGS. 16A–E. These figures illustrate a similar assembly 300 to that previously described in terms of general parts, though some such parts differ in structure and functionality, and therefore where appropriate similar reference numerals will be used for the purpose of describing the features of this embodiment notwithstanding certain differences.

More specifically, the FIGS. 16A–E embodiment illustrates that a simple transverse cut or diamond pattern cut may be suitable for use of a prosthetic elongate body according to the systems and methods herein contemplated. With respect to such a modified pattern, adjacent portions 340, 350 of the wall 325 bordering the grooved void 330 are less nested and fitted than the previous embodiment where the voids converged at an apex along the longitudinal axis. As a result of the present embodiment, mechanical interference to transverse motion under stress force is minimized. This allows for a bending response in more than one plane. In other words, the shape for each of the voids 330 is such that the elongate body 320 is adapted to experience at least a controlled amount of bending in more than one plane in the second configuration, as illustrated by means of bolded arrows in FIG. 16C.

Figure 17A:
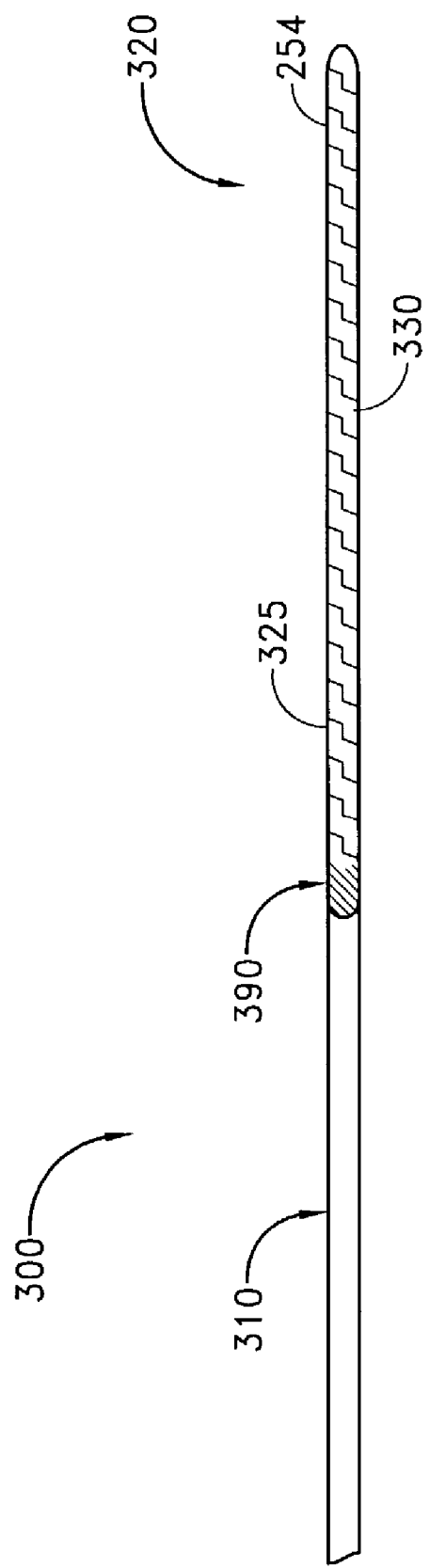
FIG. 17A shows a side elevational view of a distal end portion of a delivery assembly coupled to another elongate body which is adapted for use according to the device assembly shown in FIG. 14 during one mode of use.

Another example of a similar overall assembly but incorporating a different overall void pattern and therefore functionality is illustrated in FIG. 17A. Here, a single continuous void 330 is provided that runs in a helical pattern down the length of elongate body 320 from one end to the other. Such a pattern leaves a structure for wall 325 that forms a tightly wound helix that is integral and continuous from one end portion to the other of the elongate body 320. This helical wall provides a support having radial flexibility, though the adjacent turns of the helix are observed to stack upon each under axial compressive forces—the result is a preferentially rigid body 320 under axial tension but preferentially flexible in radial bending. Such helical void 330 may also be shaped to provide for a ratcheting of adjacent winds of the helical wall 325 in a similar manner provided above by reference to a ratcheting interface between confronting regions of the void of FIG. 15H. This is shown for example by the stepped pattern provided in FIG. 17A.

For the purpose of illustration, FIGS. 17A–E show variations and modes of operation for the assembly of FIG. 17A according to an embodiment using only one forming element 365 for deflecting the respectively coupled elongate body 320. However, the specific structure for elongate body 320 as just described for FIG. 17A may also have multiple deflectable regions with multiple interfacing forming elements, as previously described above for the other embodiments. However, FIGS. 17B–C and FIGS. 17D–E in the single forming element form provide a simplified illustration for a detachable, permanent implant embodiment of the device of FIG. 17A and of a non-detachable, temporary implant embodiment, respectively.

More specifically, FIGS. 17B–C show forming element 365 that includes a proximal tension member 366 and a distal tension member 367 with interlocking hooks. Distal tension member 367 includes a ratchet assembly 368 with teeth 369 that interact with a pawl 328 that is secured to the proximal end portion of elongate body 320. Distal tension member 367 is drawn proximally relative to elongate body 320 by means of proximal pulling on proximal tension member 366 via their interlocking hook coupling. Elongate body 320 is held substantially stationary by advancing inner member 312 distally to house the interlocked hooks 366, 367 and distally abut the proximal end portion of elongate body 320. Accordingly, ratchet 368 is drawn proximally across pawl 328 which responds by deflecting over the teeth 369 and locking back down between the teeth 369. Additional proximal movement of member 367 continues to tension elongate body 320 that responds by deflecting as shown in FIG. 17C and as otherwise herein described. However, by releasing the interlocking hooks distally from inner and outer delivery members 312, 310, respectively, the configuration for pawl 328 desirably operates as a lock against any distal motion of member 367 in response to the tension. Therefore, the elongate body 320 is left implanted in the coronary sinus locked in the contracted configuration shown.

It is important to appreciate that the prosthetic elongate body embodiments herein shown and described may be used in an overall permanent implant assembly and procedure, or may be incorporated into a temporary implant design. The embodiment of FIGS. 17D–E show a similar embodiment as that shown in FIGS. 17B–C, except with the significant distinction that the elongate body 320 is preferably not arranged for permanent implantation. Proximal delivery member 310 is secured to elongate body 320 and remains extending outside of the patient's body while elongate body 320 is deployed within the coronary sinus for temporary reconfiguration and remodeling of the mitral valve. As one benefit of such design, a lock is unnecessary in the distal coupling assembly between delivery member 310 and elongate body 320. Though a lock may nevertheless be incorporated into such a design, such lock should preferentially be disengageable in order to allow for in situ adjustment between the differing shapes of the first and second configurations. In addition, the structural elements of the present design are not required to sever or otherwise detach or uncouple the forming member 365 where it extends from the delivery member 310 to the elongate body 320.

Figure 18A:
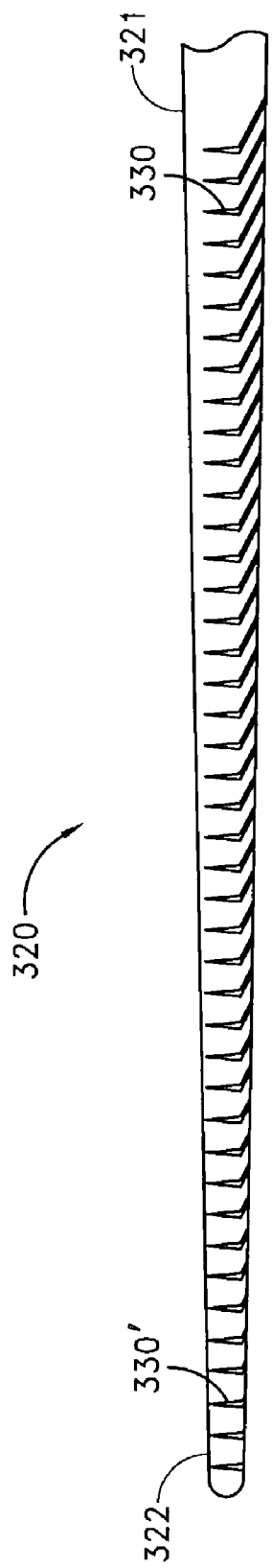
FIGS. 18A–B show side elevational views of two implants, showing alternative slot patterns.
Figure 18B:
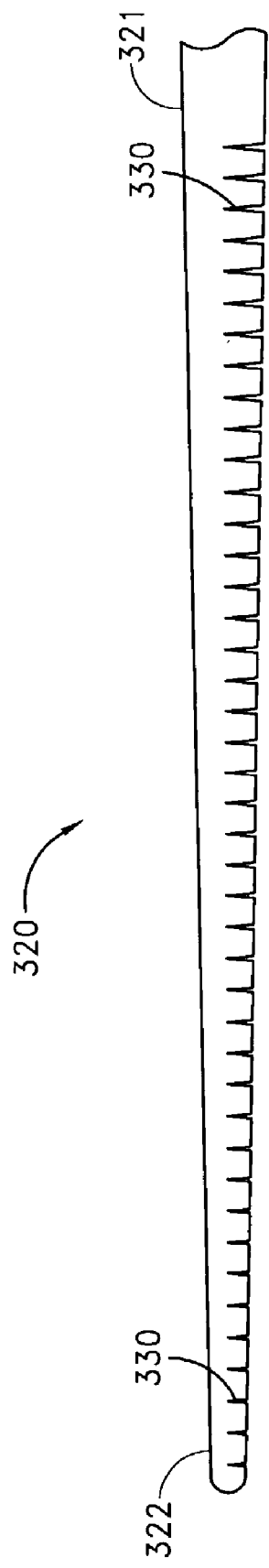

Additional variations are further contemplated for achieving controlled, desired flexion of the elongate body 320 according to the present embodiments, as is further illustrated by the tapering body design in FIGS. 18A–B. More specifically, FIG. 18A shows a tapering body 320 having a wall 325 with a distally reducing outer diameter between a proximal end portion 321 and a distal end portion 322. As shown, this particular embodiment incorporates the tapered design in combination with the V-shaped grooved void array of FIGS. 15A–H. However, other void patterns such as a simple transverse groove pattern also previously described may also be suitable with a tapering design, as shown in FIG. 18B. The distally tapering wall 325 provides for an increasingly more flexible structure along the distal aspects of body 320. In addition, by maintaining a constant pattern for the grooved voids 330 along the tapering wall, the span of the groove across the circumference of the body 320 increases and percent cross-section of the spine decreases, further contributing to increased distal flexibility. It should be further appreciated that while a continuous taper may be desirable as shown in FIGS. 18A–B, other tapers including stepped tapers may also be appropriate and are also herein contemplated.

It will also be appreciated that the wall 325 according to the various embodiments of the invention may be constructed from a variety of suitable materials, such as for example other metals than stainless steel, such as nickel-titanium alloy, titanium, platinum, iridium, alloys thereof, or the like. Alternatively, the wall 325 may be constructed from another material though, generally, the grooved void aspect of the embodiments is particularly useful for increasing the controlled, radial deflection of a generally stiff material, such as the metals described, or high density or high modulus polymers such as polyimide, high density polyethylene, and others.

Furthermore, the general patterns of voids herein described also provide similar controllability in the bending response of elongate body walls that utilize material elasticity or shape memory (e.g. superelastic or shape memory alloys such as nickel-titanium allow) for adjusting from the first to the second configurations in situ. In other words, control of in-plane vs. out-of-plane bending may also be desired for applications using material memory recovery forces instead of applied forces for reconfiguring shape. Still further, it is believed that many simple shape memory-based designs may not be adequate in all situations to achieve the desired degree of force necessary for achieving the most beneficial results in percutaneous mitral valve remodeling from the coronary sinus. By providing a superelastic or shape memory alloy in the tubular configurations herein described, a substantial wall structure (e.g. wall thickness and diameter) may be used to provide significant recovery force with grooved patterns as herein described providing the ability for bending. This combination of substantial material thickness with appreciable capacity for deflection is achieved with the patterned voided wall structures herein described, and allows for mitral valve remodeling without requiring applied forces from outside the body. However, the strength of such an overall structure in its recovered second configuration and shape for mitral valve remodeling also would provide significant problems for delivery "distal end first" through the coronary sinus.

Such a device may therefore incorporate a tensioning element that deflects the body from the recovered shape for the second configuration into a more straight or gradually curved shape for delivery in the second configuration. Such tensioning element may be a rod or wire that is detachably engaged within a lumen or passageway of the prosthesis body, which tensioning rod or wire may be disengaged once placement is achieved for the prosthesis in the sinus, and then removed to allow the body to recover to the clamped, second configuration for valve remodeling.

One aspect of the invention provides a tissue remodeling device having a prosthesis that is adapted to be positioned within a body space in order to remodel a tissue structure adjacent to that body space. Another aspect provides an extravascular tissue remodeling device for positioning within a vessel in order to remodel an extravascular tissue structure adjacent to that vessel.

Still another aspect provides a mitral valve remodeling device with a prosthesis that is adapted to be delivered in a first configuration with a first shape into a coronary sinus and to be adjusted within the coronary sinus to a second configuration with a second shape that is adapted to remodel a mitral valve adjacent to that coronary sinus. According to one mode of this aspect, the prosthesis includes an elongate body that is a generally tubular member. The tubular member has an integral wall that forms a passageway extending along a longitudinal axis between a proximal end portion and a distal end portion. The integral wall also has at least one void formed within the wall that substantially influences the second shape in the second configuration for the elongate body. In one beneficial application of this mode, the integral wall has an array of such voids that are distinct, discontinuous and spaced along the longitudinal axis. In a further beneficial application, each of the array of voids has an elongate shape that is transverse to the longitudinal axis. In one variation, at least one of these transverse voids spans across at least about 180 degrees of the circumference of the elongate body. In a further variation, at least one of the transverse voids spans across more than about 300 degrees of the circumference of the elongate body, and in still a further variation at least one void spans across between about 300 degrees and about 315 degrees of the circumference.

A further variation of the voided, integral wall application allows for a bending response in more than one plane. The shape for each of the voids is such that the elongate body in the second configuration is adapted to experience at least a controlled amount of bending in more than one plane.

In another variation, at least one of the transverse voids has a groove-shaped region with two adjoining portions that converge at an apex along the longitudinal axis. Such a shaped void is defined at least in part by two opposing shaped surfaces of two adjacent portions of the wall of the elongate body: one that is convex and one that is concave around the apex. These shaped surfaces are in a nested configuration with the convex positioned within the concave, such that lateral movement of one of the adjacent wall portions relative to the other is substantially prevented by a mechanical interference with the other adjacent portion. This relative nesting of adjacent portions of the elongate body provides a mechanical interference to radial deflection along a first plane and substantially isolates deflection of the elongate body along a second plane upon application of axial bending forces. In one more detailed variation of these nested, shaped voids, the adjacent wall portions converge distally to the apex of the respective void. In another detailed variation, the adjacent wall portions converge proximally along the elongate body to the apex. Still a further variation includes discrete voids that converge distally to the apex, and also includes other voids converging proximally.

According to another mode of the mitral valve remodeling assembly aspect of the invention, the prosthesis includes an elongate body that extends along a longitudinal axis between a proximal end portion and a distal end portion. The elongate body has more than one region along the longitudinal axis that is at least partially independently deflectable between the first and second configurations with an applied force from outside of the patient's body while the elongate body is positioned within the coronary sinus.

In one highly beneficial application of this multi-deflection mode, a plurality of forming elements are coupled to the elongate body, each being coupled to a distinct one of the deflectable portions in order to apply a deflection force to that portion to reshape that portion between the first and second configurations. In one beneficial variation, each forming element is adapted to extend externally from the patient's body when the elongate body is positioned within the coronary sinus in order to be manually manipulated to apply the deflection force to the respectively coupled deflectable portion. In a further beneficial variation, the applied force is an axial force between a distal location where the forming element is attached to the elongate body at or distal to the distal end of the respective deflectable portion and a proximal location along the elongate body that is proximal to that deflectable portion. In one regard, this axial force is between the attachment point and the proximal end portion of the elongate body. In another further more detailed variation, the elongate body is engaged by a holding device in order to substantially fix the proximal end portion of the elongate body relative to the deflectable portion so that the axial force may be applied between those portions in situ. The proximal manipulation of the forming elements in order to apply the deflection force to the deflectable portions may in one regard be axial, or may in another regard be rotational.

In still a further variation applying multiple forming elements to the multideflection mode, each deflectable portion is substantially axially rigid and non-compressible relative to the longitudinal axis. However, each deflectable portion is relatively flexible along a radial axis transverse to the longitudinal axis such that the deflectable portion is adapted to bend radially upon application of an axial force between a distal location on the elongate body at or distal to a distal end of the deflectable portion and a proximal location along the elongate body proximal to that deflectable portion. In one regard, the elongate body may be generally axially non-compressible or non-expandable between each deflectable portion and the proximal end portion of the elongate body, such that each deflectable portion is adapted to bend radially upon application of a compressive or tensile axial force, respectively, on the elongate body between the distal location and a proximal location that is at the proximal end portion of the elongate body.

In still a further regard to these multiple forming element/ multiple deflectable portion variations, the elongate body may include a wall that is substantially integral and continuous from the proximal end portion to the distal end portion and that is constructed in a manner that provides the radial bending response to axially compressive or tensile forces. In one further variation, such wall may include an array of formed voids. In still a more detailed embodiment of this arrayed void variation, the array may include a plurality of groups of voids, each group being associated with one of the deflectable portions and having a plurality of the voids arranged in a pattern for providing a desired bending response along that deflectable portion. The forming element that operates the respective deflectable portion may be attached to the elongate body at a location at or distal to the most distal void of the respective group. In addition or in the alternative to the continuous integral wall incorporating the formed voids, the wall may also include an engineered composite support structure with engineered support elements that are arranged to control the spacial strain response to the stress of the applied forces.

In yet a further variation, the deflectable portions bend radially as the elongate body is adjusted with force from the first to the second configuration in a manner such that the overall axial length of the elongate body along at least the deflectable portions does not substantially change during such adjustment.

Another aspect of the invention is a prosthesis that is implantable within a vessel of a patient and that includes an elongate body having a substantially tubular member with an integral, continuous wall extending along a longitudinal axis between a proximal end portion and a distal end portion. An array of distinct, discontinuous voids are formed within the tubular member and are spaced along the longitudinal axis. Each void of the array has an elongated shape transverse to the longitudinal axis. In one mode of this aspect, the array of voids are arranged in a manner such that a substantially linear portion of the wall remains as a spine that is uninterrupted by the voids and extends along a spine axis that is substantially aligned with the longitudinal axis between the proximal end portion and the distal end portion.

FIG. 19 illustrates an additional construction of a medical device 400 adapted to position an implant 402, or prosthesis, into the coronary sinus or other treatment site. Similar to the embodiments described above, medial device 400 includes a handle assembly 404 at a proximal end, while the implant 402 is located at a distal end. The handle assembly 404 and implant 402 are connected by an elongate, flexible catheter body 406. Desirably, the body 406 is or includes an extrusion of a material having sufficient column strength, that is, it resists compression in an axial direction, while permitting the body 406 to bend in a radial direction. Any of a variety of polymers well known in the transluminal catheter arts, such as HDPE or PEBAX, is used to form the body 406. However, other suitable materials may also be used. In one embodiment, the body 406 has an outside diameter of approximately 0.094 inches.

With reference to FIG. 20, a plurality of lumens or passages extend in an axial direction along the length of the catheter body 406. The illustrated extrusion includes three small lumen 408, 410, 412 and one larger lumen 414. The small lumen 408, 410, 412 may be disposed substantially within one half of the circular cross section of the body 406 and each has an inside diameter of approximately 0.024 inches. The larger lumen 414 is desirably positioned substantially within a half of the circular cross section of the body 406 opposite the small lumen 408, 410, 412 and may have a diameter of approximately 0.044 inches. Collectively, the lumen 408, 410 and 412 allow control components 400 (e.g., forming elements 365, 375, 385 of FIGS. 15 and 16) of the medical device 400 to extend from the handle assembly 404 to the implant 402 while being protected within the shaft 406. As will be described in detailed below, the control components convert operational movements of the handle assembly 404 into desired resultant movement of the implant 402. The larger lumen 414 may be used to rotatably receive a driver 436 as will be discussed. Additionally, one or more of the lumen may be used to permit irrigation to the coronary sinus, or other desired purposes.

With reference to FIGS. 21 and 22, the implant 402 is shown in greater detail. FIG. 22 is an enlarged view of a portion of FIG. 21 illustrating the releasable connection between the delivery assembly 401 in the implant 402. As described above, the implant 402 is removably connected to the delivery assembly 401 such that the delivery assembly 401 and implant 402 may be disconnected once the implant 402 has been properly positioned and tensioned within the coronary sinus or other body lumen or hollow organ.

The implant 402 defines a body portion 416, which is preferably tubular in shape with at least one central lumen extending therethrough. The overall length of the implant 402 can be varied, depending upon the intended treatment site and desired clinical performance. In one application, in which the device is intended to be positioned within the coronary sinus to reduce the diameter of the mitral valve annulus across a predetermined plane, the implant 402 is generally within the range of from about 5 cm to about 15 cm in length. For those adult patients, axial lengths within the range of from about 6 cm to about 12 cm may be used. In one embodiment, the implant 402 is approximately 9 centimeters long and, may have a cross-sectional area of no more than approximately 15 mm$^2$. Preferably, the implant 402 has a cross-sectional area of no more than 10 mm$^2$.

The implant may be constructed from a similar material as those embodiments described above, such as a variety of stainless steels, Nitinol or other known materials suitable for implantation. An atraumatic distal tip 418 is provided on the distal end of the body portion 416. A leading end of the tip 418 may be rounded such that the tip 418 will not cause significant tissue damage as it is advanced through the vasculature of the patient. An aperture 420 extends axially through the tip 418 and is in communication with the guidewire lumen as is known in the art.

A nut 422 or other structure having a threaded aperture therein is provided at the proximal end of the body portion 416. Desirably, the nut 422 is rotationally fixed relative to the body portion 416. For example, in the illustrated embodiment the outer edge of the nut 422 is circular and is sized to fit within the body portion 416. The body portion 416 may includes a notch or other interlocking surface structure that fits within a groove of the nut 422. Thus, the nut 422 is prevented from rotating relative to the body portion 416 by the interference between the notch and the groove. Similarly, other suitable arrangements for preventing relative rotation between the nut 422 and body 416 may be used, such as other mechanical interference arrangements, fasteners, or adhesives, for example The implant 402 additionally includes a screw 428 having a shaft portion 430 and a head portion 432. The shaft portion 430 includes external threads which mate with internal threads on the nut 422. Thus, rotation of the screw 428 relative to the body portion 416 results in the screw 428 translating axially with respect the body portion 416. This relative movement may be utilized to move the body portion 416 of the implant 402 from an implantation configuration to a remodeling configuration through any suitable construction, such as through the use of a pull wire or other forming element as is described above, for example.

Figure 24:
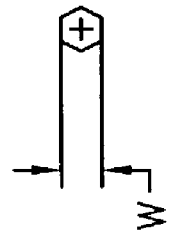
FIG. 24 is an end elevational view of a hex-shaped distal end of the driver of FIG. 23, taken along the view line 24—24 of FIG. 23.

The head portion 432 of the screw 428 includes a rotational coupling such as a cavity 434 extending axially from a proximal end of head portion 432. Desirably, the cavity 434 is shaped to receive a control component of the medical device 400 such a driver 436. In the illustrated embodiment, the cavity 434 is hex shaped and sized to receive a hex-shaped distal end portion 438 of the driver 436 (FIG. 24).

A male connector 440 is connected to the head portion 432 of the screw 428. The male connector 440 includes a shaft portion 442 and a head portion 444. The head portion 444 of the male connector 440 has a larger diameter in that of the shaft portion 442. A passage 446 desirably extends axially through the male connector 440 and defines a first portion 448 and a second portion 450. The first portion 448 of the passage 446 is located proximate the head portion 444 of the male connector 440 and has a larger diameter than that of the second portion 450, which is located proximate the shaft portion 442 of the male connector 440. A transition between the first portion 448 and the second portion 450 defines a shoulder surface 452 which extends generally transverse to the longitudinal access of the male connector 440. The first portion 448 of the passage 446 is preferably sized and shaped to receive the head portion 432 of the screw 428. Desirably, the head portion 432 of the screw 428 abuts the shoulder 452 of the passage 446.

An annular collar 454 secures the head portion 432 of the screw 428 within the passage 446. Desirably, the outer diameter of the collar 454 is approximately the same as the outer diameter of the head portion 444 of the male connector 440. The collar 454 includes an inner flange portion 456 which is sized and shaped to fit within the first portion 448 of the passage 446 of the male connector 440 in a press fit configuration.

In a similar manner to the embodiments described above, the implant 402 desirably includes a wire 458 which is operational for moving the implant 402 from a first, delivery configuration to a second, remodeling configuration. The wire 458 is desirably anchored to a distal end of the implant 402 by soldering or any of the methods described above, or any other suitable method as may be determined by one of skill in the art. Preferably, a proximal end of the wire 458 is anchored to one of the male connector 440 and the collar 454. Alternatively, the proximal of the wire 458 may be attached to another portion of the screw 428, as described in relation to the embodiments above. Desirably, the proximal end of the wire 458 is anchored to the male connector 440 and, preferably, is thermally welded or otherwise bonded to the male connector 440. However, other suitable methods of attachment may also be used, such as an adhesive or mechanical fastener, for instance. Preferably, the male connector 440, the collar 454 and the nut 422 include corresponding slots 460, 462, 464, respectively, which are sized and shaped to permit clearance for the wire to pass therethrough.

As described above, the delivery assembly 401 is preferably capable of being releasably coupled to the implant 402. For this purpose, a female connector 466 is desirably coupled to the distal end of the shaft 406. The female connector 466 is preferably hollow and substantially cylindrical in shape. The distal end of the female connector 466 includes a plurality of prongs, or finger portions 468, which are able to flex radially outward to permit the female connector 466 to engage the shaft portion 442 of the male connector 440. Desirably, the resiliency of the material from which the female connector 466 is constructed enables the female connector 466 to firmly grip the male connector 440. Desirably, an inner surface of the finger portions 468 defines an annular projection 470 which corresponds with an annular groove 472 of the male connector 440. When the female connector 466 is engaged with the male connector 440, the annular projection 470 desirably rests in the annular groove 472 to assist and inhibiting undesired relative axial movement between the delivery assembly 401 and the implant 402.

The delivery assembly 401 additionally includes a cover 474 positioned at the distal end of the shaft 406. The cover 474 is axially movable from a first position in which the finger portions 468 of the female connector 466 are uncovered to a second position where the cover 474 overlaps at least a substantial portion of the finger portions 468. In its second position, the cover 474 inhibits undesired flexing of the finger portions 468 to assist in maintaining a connection between the female connector 466 and the male connector 440.

Figure 23:
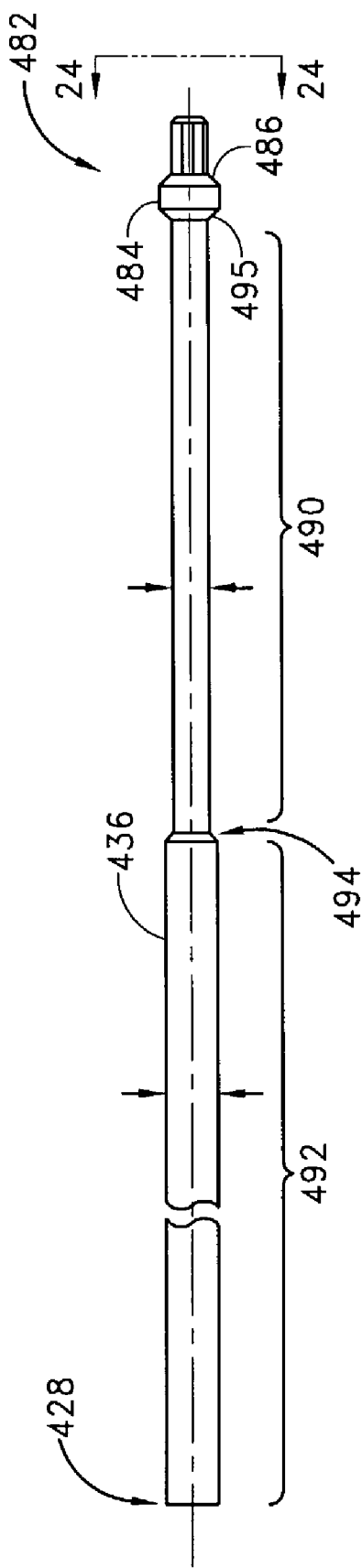
FIG. 23 is a plan view of a driver of the delivery assembly of the medical device of FIG. 19, viewed apart from the medical device.

FIG. 23 is an enlarged view of the driver 436 apart from the medical device 400. The driver 436 is desirably an elongate shaft and extends from a proximal end 480 to a distal end 482. The driver 436 may be constructed from a NiTi material, however, other suitable materials may also be used. The proximal end 480 of the driver 436 is desirably coupled for rotation with respect to the handle assembly 404, which will be described in greater detail below. The distal end 482 is preferably hex-shaped in crosssection and is sized to engage the hex-shaped cavity 434 of the screw 428. Thus, rotation of the driver 436 results in corresponding rotation of the screw 428. Other suitable arrangements to permit rotational coupling of the driver 436 and screw 428 may also be used, such as using a non-circular cross-sectional shape for the mating components, for example.

The driver 436 may include a shoulder 484 disposed on a proximal side of the hex-shaped distal end 482. Preferably, the diameter of the shoulder 484 is larger than a width W (FIG. 24) of the hex-shaped distal end 482. Preferably, the diameter of the shoulder 484 is approximately 0.032–0.040 inches and the width W is approximately 0.027 inches. Thus, the shoulder 484 effectively functions as a stop when the hex-shaped distal end 482 of the driver is inserted into the cavity 434 of the screw 428. As illustrated, the shoulder 484 and the cavity 434 desirably include complementary chamfers 486, 488, respectively, to permit easier entry of the hex-shaped distal end 482 into the cavity 434.

The illustrated driver 436 may include a reduced-diameter portion 490 on a proximal side of the shoulder 484. The diameter of portion 490 may be smaller than both the width W of the shoulder 484 and a diameter of a main portion 492 of the driver 436, which desirably extends from proximal the portion 490 to the proximal end 480. Preferably, the main portion 492 of the driver 436 has a diameter of approximately 0.04 inches. The reduced-diameter portion 490 may have a length of approximately 0.5 inches and a diameter of approximately 0.027 inches. However, other suitable dimensions may also be employed. Desirably, each of the transition between the reduced-diameter portion 490 and the main portion 492 of the driver 436 and the transition between the reduced-diameter portion 490 and the shoulder 484 define a chamfer 494, 495, respectively to advantageously reduce stress concentrations.

Figure 25:
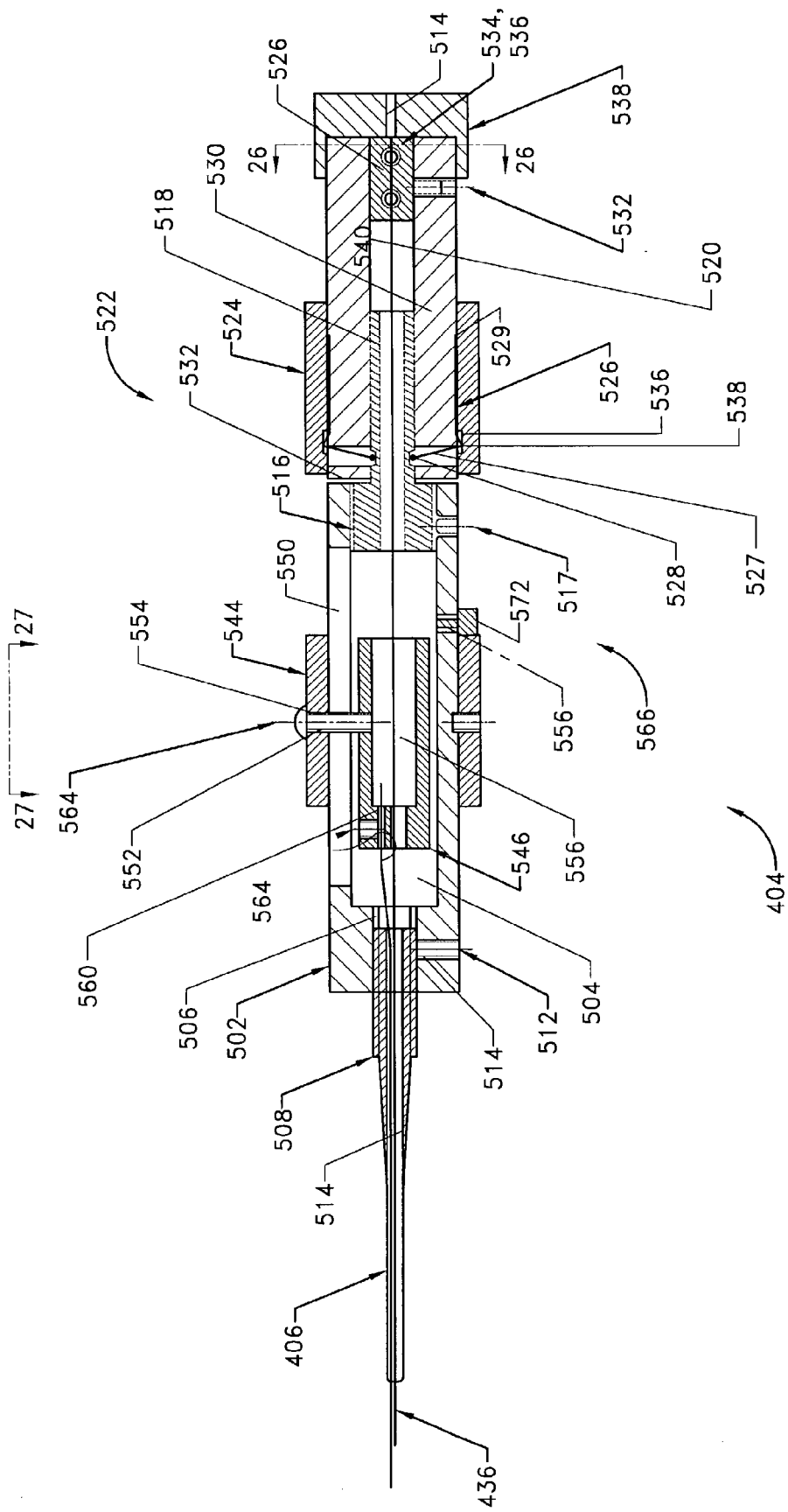
FIG. 25 is a cross section view of the handle assembly of the medical device of FIG. 19.

FIG. 25 is an enlarged cross-section of the handle assembly 404, which is primarily comprised of a proximal handle 500 and a distal handle 502. Desirably, the driver 436 is coupled for rotation with the proximal handle 500. Preferably, the distal handle 502 is configured to be held stationary during use of the medical device 400 and the proximal handle 500 is configured to be rotatable with respect to the distal handle 502, thus rotating the driver 436 to selectively move the implant 402 between a delivery position and a remodeling position.

The distal handle 502 is generally cylindrical in shape and defines an internal cavity 504. A threaded aperture 506 extends from the cavity 504 through the distal end of the distal handle 502 and is substantially concentric with a longitudinal axis of the handle assembly 404. A proximal connector 508 is desirably retained by a threaded connection with the threaded aperture 506 and extends axially from a distal end of the distal handle 502. Desirably, the distal handle 502 additionally includes a threaded aperture 510 situated substantially transverse to the longitudinal axis and intersecting the threaded aperture 506. A set screw 512 is advantageously in threaded connection with the threaded aperture 506 and may be tightened against the proximal connector 508 to inhibit undesired axial movement of the proximal connector 508 with respect to the distal handle 502.

The proximal connector 508 includes a central aperture 514 passing axially therethrough. The central aperture 514 is desirably substantially concentric with the longitudinal axis of the handle assembly 404 and receives the shaft 406 in a fixed axial position with respect to the distal handle 502. The shaft 406 may be fixed to the proximal connector 508 in any suitable manner, such as by adhesives or thermal welding, for example.

In the illustrated embodiment, the cavity 504 opens through the proximal end of the distal handle 502 to receive a handle connector 516, preferably through a threaded connection therebetween. In addition, a set screw arrangement 517, similar to that describe above in relation to the proximal connector 514, is desirably provided to inhibit undesired movement of the handle connector 516. The handle connector 516 is configured to connect the proximal handle 500 and the distal handle 502, while allowing relative rotation therebetween. The handle connector 516 desirably includes a shaft portion 518 extending proximally away from the distal handle 502. A cylindrical passage 520 extends axially through the proximal handle 500 and is sized to be rotatably mounted on the shaft portion 518 of the handle connector 516.

Preferably, the proximal handle 500 includes a handle release assembly 522 that permits releasable engagement to the distal handle 502. The release assembly desirably comprises an annular release collar 524 surrounding the proximal handle 500. The release collar 524 is sized to allow axial movement with respect to the proximal handle 500. A plurality of wire retainers 526 (two shown) releasably engage the shaft portion 518 of the handle connector 516 to selectively secure the proximal handle 500 in a fixed axial position with respect to the distal handle 502. Each of the wire retainers 526 include a short leg 527, which is circular in cross-section and terminates in a ball end 528, and a long leg 529, which is preferably rectangular in cross-section. Desirably, the short leg 527 and the long leg 529 define an angle of approximately 75° between them when the wire retainer 526 is in a relaxed position. Preferably, each wire retainer 524 is constructed from a variety of stainless steel and a total of four wire retainers 526 are employed.

In the illustrated embodiment, the long leg 529 of the retainer 524 is held between an outer surface of the proximal handle 500 and an inner surface of the release collar 524 and, preferably, within a groove 530 defined by the proximal handle 500. A plurality of apertures 532 extend radially through the proximal handle 500 near its distal end. Each aperture 532 is axially aligned with one of the grooves 530 and is spaced slightly from a distal end of the associated groove 530. The outer surface of the proximal handle 500 defines a shoulder 534 between the grooves 530 and the apertures 532. The shoulder 534 mechanically deflects the wire retainer 526, when secured by the release collar 524, such the angle between the short leg 527 and long leg 529 is increased from the relaxed position of the wire retainer 526. The inner surface of the release collar 524 defines an annular groove 536, which desirably straddles the shoulder 534, at least when the release collar 524 is in a relaxed position. The short leg 527 of the wire retainer 526 extends through the aperture 532. The groove 526 preferably engages a bend 538 defined by the transition between the short leg 527 and the long leg 529 of the wire retainer 526 to hold the ball end 528 within an annular groove 540 defined by the shaft portion 518 of the handle connector 516.

In FIG. 25, the release collar 524 is in a first, or engaged position such that the ball end 528 being held within the annular groove 540 inhibits removal of the proximal handle 500 from the distal handle 502. The release collar 524 is movable toward the proximal end of the proximal handle 500 into a second, or release position to selectively permit the proximal handle 500 to be removed from the distal handle 502. When the release collar 524 is moved toward the release position, an edge of the groove 536 engages the wire retainer 526 to deflect the short leg 527 and move the ball end 528 out of the groove 540 of the handle connector 516, thereby releasing the proximal handle 500 from the distal handle 502.

Figure 26:
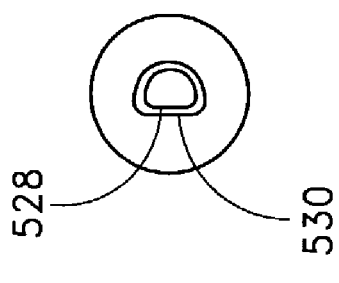
FIG. 26 is a cross section of a portion of the handle assembly of FIG. 25 including a driver holder, taken along the view line 26—26 of FIG. 25.

A driver holder 526 is positioned within the proximal end of the passage 520 to fix the driver 436 for rotation with the proximal handle 500. Thus, the driver holder 526 is fixed for rotation with the proximal handle 500, preferably by having a flat 528 which is engaged by a flat portion 530 of the proximal end of the passage 520 (FIG. 26). Desirably, a set screw arrangement 532, similar to those described above, secures the driver holder 526 axially with respect to the proximal handle 500. A pair of set screws 534, 536 secure the driver 436 axially and rotationally with respect to the proximal handle 500. Thus, rotation of the proximal handle 500 results in rotation of the driver 436. Desirably, and end cap 538 is press fit over the proximal end of the proximal handle 500 to further secure the driver holder 526. The end cap 538 may include an aperture 540 extending axially therethrough. Desirably, the aperture 540 is substantially aligned with the driver 436.

Figure 27:
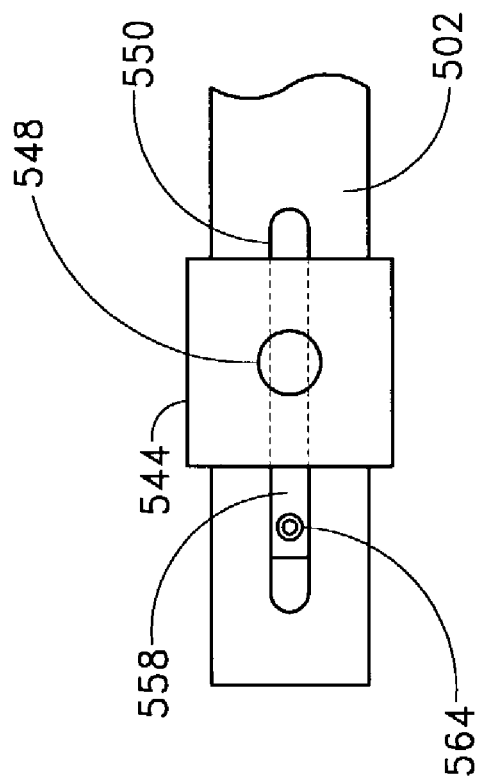
FIG. 27 is a plan view of the handle assembly of FIG. 25 taken along the view line 27—27 of FIG. 25.

With reference to FIGS. 25 and 27, the distal handle 502 includes a detach arrangement 542 which allows the delivery assembly 401 to be detached from the implant 402 once it has been properly positioned and moved from its delivery position into its remodeling position. The detach arrangement 542 includes an annular detach collar 544 surrounding the distal handle 502. The detach collar 544 is desirably concentric with the distal handle 502 and capable of sliding axially thereon. A handle pin 546 is positioned concentrically within the cavity 504 of the distal handle 502. A fastener, such as a screw 548, passes through a slot 550 in the distal handle 502 to connect the handle pin 546 to the detach collar 544. Preferably, external threads of the fastener 548 mate with internal threads of apertures 552, 554 of the detach collar 544 and handle pin 546, respectively, to provide a secure connection therebetween.

The handle pin 546 is desirably substantially cylindrical in shape and defines an internal cavity 556 extending from an open proximal end to a closed distal end of the handle pin 546. The closed distal end of the handle pin 546 includes a pair of apertures 558, 560 extending axially therethrough, opening into the cavity 556. The aperture 558 is sized and positioned to permit the driver 436 to pass there through. The aperture 560 is sized to receive a proximal end of a detach wire 562. The detach wire 562 extends from the handle pin 546 to the cover 474 (FIG. 22) through one of the apertures 408, 410, 412 of the shaft 406. The detach wire 562 is secured to the cover 474 by any suitable method, such as thermal welding, adhesives, or mechanical fasteners, for example. A set screw arrangement 564, similar to those described above, is utilized to secure the detach wire 562 within the aperture 560 for axial movement with the handle pin 546. Thus, when the detach collar 544 is moved toward the proximal end of the handle assembly 404, the detach wire 562 pulls the cover 474 to uncover the finger portions 468 of the female connector 466. When the cover 474 is in this position, the female connector 466 is able to be disconnected from the male connector 440 and, thus, the delivery assembly 401 is able to be disconnected from the implant 402, as described above.

The handle assembly 404 also desirably includes a detach collar lock arrangement 566 to substantially prevent undesired movement of the detach collar 544. The lock arrangement 566 preferably includes a threaded aperture 568 passing radially through the distal handle 502. A lock screw 570 is provided for threaded engagement with the threaded aperture 568. The lock screw 570 includes a head portion 572, which interferes with movement of the detach collar 544 toward a proximal end of the handle assembly 404 when the lock screw 570 is screwed substantially fully into the aperture 568. The lock screw 570 may be backed partially, or fully, out of the aperture 568 to permit desired movement of the detach collar 544 toward the proximal end of the handle assembly 404.

Operation of the medical device 400 is substantially similar to the embodiments described above. Preferably, before the procedure is initiated, the lock screw 570 is positioned to prevent undesired movement of the detach collar 544, which could result in premature detachment of the delivery assembly 401 from the implant 402. Once the implant 402 has been desirably positioned within the coronary sinus by a suitable method, such as described above, the proximal handle 500 is rotated with respect to the distal handle 502 to cause rotation of the driver 436. Rotation of the driver 436 results in corresponding rotation of the screw 426 which, in turn, causes the implant 402 to move from a delivery configuration to a remodeling configuration, as described in detail above. The direction of rotation of the proximal handle 500 will vary depending on the orientation of the threaded connection between the screw 428 and the nut 422. However, if a right hand thread orientation is used, the proximal handle 500 will be rotated counter-clockwise to move the implant 402 from a delivery configuration to a remodeling configuration.

When the implant 402 has achieved a desired remodeling configuration, the lock screw 570 is backed off from its locked position to permit movement of the detach collar 544. The detach collar 544 may then be moved toward the proximal end of the handle assembly 404, thereby retracting the cover 474 and exposing the finger portions 468 of the female connector 466. The handle assembly 404 may then be pulled with a sufficient force to cause the finger portions 468 of the female connector 466 to deflect radially outwardly such that the female connector 466 may be disconnected from the male connector 440, thus disconnecting the delivery assembly 401 from the implant 402. The delivery assembly 401 is then removed from the patient, leaving the implant 402 in place.

Figure 28:
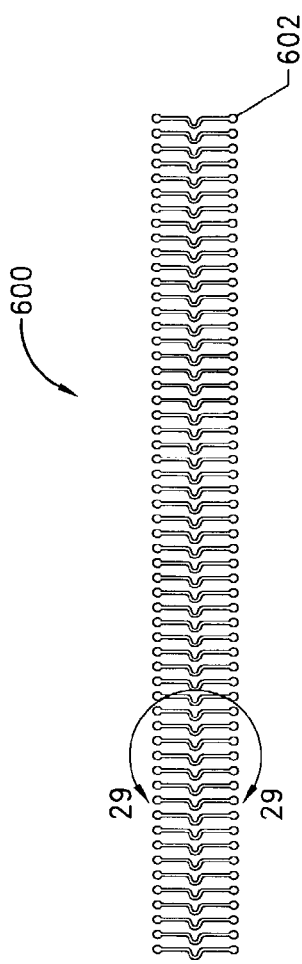
FIG. 28 is a plan view of a slot pattern of the implant of FIG. 19.
Figure 29:
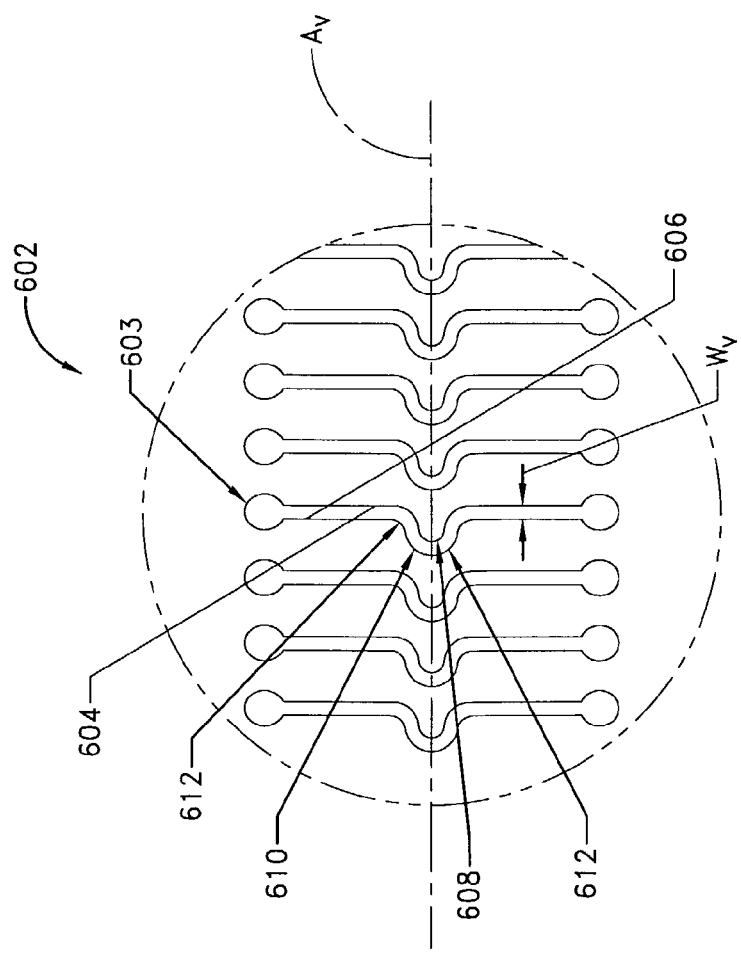
FIG. 29 is an enlarged view of a single slot of the slot arrangement of FIG. 28.

FIGS. 28 and 29 illustrate the slot pattern on an alternative implant 600, similar to those described above in relation to FIGS. 14–18, incorporating voids 602 to influence the movement of the implant 402 from a delivery configuration to a remodeling configuration. FIG. 28 illustrates a plan view of a preferred void 602 arrangement, wherein 57 individual voids 602 are provided. In general, a first side of the implant is generally noncompressible, such as is achieved by the use of a tubular wall. The first side of the implant is radially opposite a second side of the implant, which is provided with the plurality of voids 602. The voids permit the second side of the implant to be axially expanded or contracted, thereby curving the implant as will be apparent to those of skill in the art. The number and configuration of the voids 602 will influence the bending characteristics of the implant. In general, voids which are transverse to the longitudinal axis of the implant can assist in plane bending of the implant. For most implants intended for positioning within the coronary sinus, and therefore having an axial length of within the range of from about 5 to about 16 cm, at least about 10 and often at least about 20 voids are provided. Thirty or forty or more voids may also be provided, depending upon the desired finished curvature of the implanted device as well as the dimensions of the voids and intervening solid wall material.

FIG. 29 is an enlarged view of a single void 602. As in the embodiments described above, a plurality of voids 602 are arranged axially along the implant 402 and are positioned substantially transverse to the longitudinal axis of the implant 402. Desirably, the voids 602 extend around at least about 180° of the circumference of the implant 402 and, preferably, around at least approximately 300° of the circumference. In some embodiments, the voids 602 extend around between approximately 300° and 315° of the circumference of the implant 402. Alternatively the tubular body of the implant may comprise a spring coil in which adjacent windings are slightly spaced apart. Axial column strength on the first side of the implant is provided by an axially extending support such as a flexible ribbon or core wire which may be soldered or otherwise attached to the spring coil to inhibit axial compression along the side which carries the support. The opposing side of the coil may be compressed or expanded, to impart a curve. The coil may be provided with an outer polymeric sleeve.

Desirably, both ends of each void 602 terminate in a circular void portion 603. Advantageously, the circular portions 603 of the void 602 reduce stress concentrations at the ends of the voids 602 that result from bending of the implant 402 from a delivery configuration to a remodeling configuration. Preferably, the circular portions 603 have a diameter of approximately 0.03 inches and a circumferential distance between the centers of the circular portions 603 of a single void 602 is approximately 0.027 inches. This feature decreases the likelihood of cracks originating in material of the implant 402 at the ends of the voids 602.

Each void 602 is defined by opposing edge surfaces 604, 606 of the body of the implant 402. Surface 604 includes a substantially "U-shaped" projection 608 positioned within a complementary, substantially "U-shaped" recess 610 of surface 606. Alternative complementary configurations such as a chevron may also be used. An axis $A_V$ of both the projection 608 and the recess 610 is substantially parallel to the longitudinal axis of the implant 402.

An axial distance between the substantially transverse portions of the surfaces 604, 606 defines a width $W_V$ of the void 602. The $W_V$ of the void 602 may be varied, depending upon the desired performance. In general, widths within the range of from about 0.010 to bout 0.040 inches are often used. In the illustrated embodiment, the width $W_V$ is approximately 0.015 inches. Desirably, a distance between at least a portion of both sides of the projection 608 and recess 610 is less than the void width $W_V$ and defines a pair of interference portions 612 between the surface 604 and the surface 606.

The interference portions 612 inhibit the implant 402 from moving out of a plane defined by the longitudinal axis of the implant 402 as it moves from a delivery configuration to a remodeling configuration. Advantageously, the surfaces 604, 606 contact one another in the interference portions 612 of the void 602 in response to a force urging the implant 402 to curve out of plane. Thus, with the illustrated arrangement, the implant 402 is maintained within the desired plane while moving from a delivery configuration to a remodeling configuration. Alternatively, the void 602 may be configured to permit out of plane movement of the implant 402 if such is desirable, as will be appreciated by one of skill in the art. For example, only one interference portion 612 may be provided or the distance between the surfaces 604, 606 may be increased in the interference portion 612.

Although the present invention has been described in terms of certain preferred embodiments, it may be incorporated into other embodiments or performed through other steps by persons of skill in the art in view of the disclosure herein. In addition, features from any one of the embodiments disclosed herein may be incorporated into other embodiments as will be apparent to those of skill in the art. The scope of the invention is therefore not intended to be limited by the specific embodiments disclosed herein, but is intended to be defined by the full scope of the following claims.

What is claimed is:

1. A medical apparatus for remodeling a mitral valve annulus adjacent to the coronary sinus, comprising:
   an elongate body, having a proximal end region and a distal end region, each of the proximal and distal end regions dimensioned to reside completely within the vascular system, the elongate body being movable from a first configuration for transluminal delivery to at least a portion of the coronary sinus to a second configuration for remodeling the mitral valve annulus proximate the coronary sinus;
   a forming element attached to the elongate body for manipulating the elongate body from the first transluminal configuration to the second remodeling configuration; and
   a lock for retaining the body in the second configuration;
   wherein the elongate body comprises a tube having a plurality of transverse slots therein and wherein the forming element includes a distal end portion fixed to the tube.

2. A medical apparatus as in claim 1, wherein the elongate body forms an arc when in the remodeling configuration, by changing the shape of the slots.

3. A medical apparatus as in claim 2, wherein a best fit constant radius curve corresponding to the arc has a radius within the range of from about 10 mm to about 20 mm.

4. A medical apparatus as in claim 1, wherein the lock comprises an interference fit.

5. A medical apparatus as in claim 1, wherein the lock comprises a compression fit.

6. A medical apparatus as in claim 1, wherein the lock comprises a ratchet.

7. A medical apparatus as in claim 1, wherein the lock comprises an engagement surface, which is movable between a first, disengaged configuration and a second, engaged configuration.

8. A medical apparatus as in claim 1, wherein the lock is biased in a locked direction.

9. A medical apparatus as in claim 1, wherein the lock is biased in an unlocked direction.

10. A medical apparatus as in claim 1, further comprising a coating on the body.

11. A medical apparatus as in claim 1, wherein the apparatus is movable from the implantation configuration to the remodeling configuration in response to proximal retraction of the forming element.

12. A medical apparatus as in claim 1, wherein the apparatus is movable from the implantation configuration to the remodeling configuration in response to distal advancement of the forming element.

13. A medical apparatus as in claim 1, further comprising an anchor for retaining the apparatus at a deployment site within a vessel.

14. A medical apparatus as in claim 13, wherein the anchor comprises a distal extension of the apparatus.

15. A medical apparatus as in claim 13, wherein the anchor comprises a friction enhancing surface structure for engaging the wall of the vessel.

16. A medical apparatus as in claim 13, wherein the anchor comprises at least one barb for piercing the wall of the vessel.

17. A medical apparatus as in claim 1, wherein the apparatus has an axial length of no more than about 10 cm.

18. A medical apparatus as in claim 17, wherein the maximum cross sectional dimension through the apparatus is no more than about 10 mm.

19. A medical apparatus as in claim 1, wherein the plurality of transverse slots are located along a side of the tube and wherein the distal end portion of the forming element is fixed to the tube at the side of the tube along which the plurality of transverse slots are located.

20. An implant for positioning within a patient, comprising:
   an elongate flexible body having a proximal end and a distal end, and a longitudinal axis extending therebetween, and first and second opposing sides extending along the implant body at least part way between the proximal end and the distal end, the first side having a fixed axial length, and the second side having an adjustable axial length;
   at least a first forming element extending through the body to a distal point of attachment to the body; and
   a detachable coupling on a proximal portion of the body, for removably attaching the body to a deployment catheter;
   wherein manipulation of the first forming element deflects at least a first portion of the body away from the longitudinal axis.

21. An implant as in claim 20, wherein the body comprises a tubular wall.

22. An implant as in claim 21, wherein the tubular wall is substantially noncompressible along the first side.

23. An implant as in claim 22, comprising a plurality of voids in the wall along the second side, thereby permitting axial shortening of the second side.

24. An implant as in claim 23 wherein at least some of the voids comprise slots through the wall, extending generally transverse to the longitudinal axis.

25. An implant as in claim 24 comprising at least 10 transverse slots in the wall of the second side.

26. An implant as in claim 24 comprising at least 20 transverse slots in the wall of the second side.

27. An implant as in claim 20, wherein the first forming element comprises an axially movable element.

28. An implant as in claim 20, wherein the first forming element comprises a pull wire.

29. An implant as in claim 20, further comprising at least a second forming element.

30. An implant as in claim 29, wherein manipulation of the first forming element introduces a first curve in the body, and manipulation of the second forming element introduces a second curve in the body.

31. An implant as in claim 20, wherein distal movement of the forming element causes axial elongation of the second side thereby bending the implant.

32. An implant as in claim 20, wherein proximal movement of the forming element causes axial compression of the second side thereby bending the implant.

33. A multizone vascular implant, comprising:
   a tubular body having a proximal end region and a distal end region, each of the proximal and distal end regions dimensioned to reside completely within the vascular system, the tubular body being movable from a first configuration for transluminal delivery to at least a portion of the coronary sinus to a second configuration for remodeling the mitral valve annulus proximate the coronary sinus;
   a plurality of transverse voids on the tubular body to permit flexing in at least one plane;
   at least a first, proximal zone and a second, distal zone on the body;
   a first control wire for imparting curvature in the first zone; and
   a second control wire for imparting curvature in the second zone.

34. A multizone vascular implant as in claim 33, further comprising a third control wire for imparting curvature in a third zone.

35. A medical apparatus for remodeling a mitral valve annulus adjacent to the coronary sinus, comprising:
   an elongate body, having a proximal end region and a distal end region, each of the proximal and distal end regions dimensioned to reside completely within the vascular system, the elongate body being movable from a first configuration for transluminal delivery to at least a portion of the coronary sinus to a second configuration for remodeling the mitral valve annulus proximate the coronary sinus;
   a forming element attached to the elongate body for manipulating the elongate body from the first transluminal configuration to the second remodeling configuration; and
   a lock for retaining the body in the second configuration;
   wherein the elongate body comprises a tube having a plurality of transverse slots therein; and,
   wherein the forming element extends through the elongate body from the proximal end region to the distal end region.

* * * * *